US011149285B2

(12) United States Patent
Bosch Tubert et al.

(10) Patent No.: US 11,149,285 B2
(45) Date of Patent: Oct. 19, 2021

(54) ADENOASSOCIATED VIRUS VECTORS FOR THE TREATMENT OF LYSOSOMAL STORAGE DISORDERS

(71) Applicants: UNIVERSITAT AUTÓNOMA DE BARCELONA, Cerdanyola del Valles (ES); ESTEVE PHARMACEUTICALS, S.A., Barcelona (ES)

(72) Inventors: M Fàtima Bosch Tubert, Cerdanyola del Valles (ES); M Virginia Haurigot Mendoça, Barcelona (ES); Albert Ribera Sanchez, Santa Eulàlia de Ronçana (ES)

(73) Assignees: UNIVERSITAT AUTÓNOMA DE BARCELONA, Cerdanyola del Valles (ES); ESTEVE PHARMACEUTICALS, S.A., Barcelona (ES)

( * ) Notice: Subject to any disclaimer, the term of this patent is extended or adjusted under 35 U.S.C. 154(b) by 8 days.

(21) Appl. No.: 15/310,524

(22) PCT Filed: May 13, 2015

(86) PCT No.: PCT/EP2015/060604
§ 371 (c)(1),
(2) Date: Nov. 11, 2016

(87) PCT Pub. No.: WO2015/173308
PCT Pub. Date: Nov. 19, 2015

(65) Prior Publication Data

US 2017/0088859 A1 Mar. 30, 2017

(30) Foreign Application Priority Data

May 14, 2014 (EP) .................................... 14382171

(51) Int. Cl.
*A01N 63/00* (2020.01)
*C12N 15/86* (2006.01)
*C12N 9/26* (2006.01)
*A61K 48/00* (2006.01)
*A61K 38/47* (2006.01)

(52) U.S. Cl.
CPC .............. *C12N 15/86* (2013.01); *A61K 38/47* (2013.01); *A61K 48/005* (2013.01); *C12N 9/2474* (2013.01); *C12Y 302/0105* (2013.01); *A61K 48/00* (2013.01); *A61K 48/0075* (2013.01); *C12N 2750/14143* (2013.01); *C12N 2800/22* (2013.01); *C12N 2830/008* (2013.01); *C12N 2840/105* (2013.01)

(58) Field of Classification Search
CPC ....... A61K 38/47; C12N 15/86; C12N 9/2474
See application file for complete search history.

(56) References Cited

U.S. PATENT DOCUMENTS

2013/0039888 A1 2/2013 McCarty et al.
2014/0249208 A1* 9/2014 Bancel .................. A61K 38/00
2014/0255383 A1* 9/2014 Quinn ................... A61K 38/47

FOREIGN PATENT DOCUMENTS

| | | | |
|---|---|---|---|
| EP | 2 394 667 | | 12/2011 |
| JP | 2013-531490 | | 8/2013 |
| WO | WO2008044869 | * | 4/2008 |
| WO | WO2011154520 | | 12/2011 |
| WO | WO2012012742 | | 1/2012 |
| WO | WO2013055888 | | 4/2013 |

OTHER PUBLICATIONS

Hocquemiller et al, (Human Gene Therapy, 27(7): 478-496, 2008) (Year: 2008).*
Gilkes et al (Gene Therapy (2016) 23, 263-271) (Year: 2016).*
Chen et al, (Molecular Therapy, 26(4): 1118-1126, 2918) (Year: 2018).*
Jamil (Thesis, pp. 1-69, 2016) (Year: 2016).*
Gaffke (Metab Brain Dis (2018) 33:1-10) (Year: 2018).*
Sawamoto (Mol Genet Metab. 123(2): 59-68, 2018) (Year: 2018).*
Bainbridge, James W.B et al., "Effect of gene therapy on visual function in Leber's Congenital Anaurosis", The New England Journal of Medicine, 2008, 358: 2231-2239.
Boelens, Jaap J. et al., "Current international perspectives on hematopoietic stem cell transplantation for inherited metabolic disorders", Pediatr. Clin. N. Am., 2010, 57: 123-145.
Buchlis, George et al., "Factor IX expression in skeletal muscle of a severe hemophilia B patient 10 years after AAV-mediated gene transfer", Blood, 2012, 119: 3038-3041.
Cleary, M A, et al., "Management of mucopolysaccharidosis type III", Archives of Disease in Childhood, 1993, 69: 403-406.
Cressant, Arnaud et al. "Improved behavior and neuropathology in the mouse model of Sanfilippo type IIIB disease after adeno-associated virus-mediated gene transfer in the striatum", The Journal of Neuroscience, Nov. 10, 2004, 24(45): 10229-10239.
De Ruijter, J. et al., "Mucopolysaccharidiosis type III (Sanfilippo syndrome): emerging treatment strategies", Current Pharmaceutical Biotechnology, 2011, 12: 923-930.
De Ruijter, Jessica et al., "Genistein in Sanfilippo disease: a randomized controlled crossover trial", Ann. Neurol., 2012, 71: 110-120.
Delgadillo, Verónica et al., "Genistein supplementation in patients affected by Sanfilippo disease", J. Inherit. Metab. Dis., 2011, 34:1039-1044.
Di Domenico, Carmela et al., "Intracranial gene delivery of LV-NAGLU vector corrects neuropathology in murine MPS IIIB", Am. J. Med. Genet. Part A, 2009, 149A: 1209-1218.
Di Natale, Paola et al., "Treatment of the mouse model of mucopolysaccharidosis type IIIB with lentiviral-NAGLU vector", Biochem. J., 2005 388: 639-646.

(Continued)

*Primary Examiner* — Michael C Wilson
(74) *Attorney, Agent, or Firm* — Hueschen and Sage

(57) ABSTRACT

The present invention provides new adenoassociated virus vectors and pharmaceutical compositions containing the same for the treatment of lysosomal storage disorders and specially, for the treatment of mucopolysaccharidoses Type IIIB.

16 Claims, 24 Drawing Sheets

Specification includes a Sequence Listing.

(56) References Cited

OTHER PUBLICATIONS

Duque, Sandra et al., "Intravenous administration of self-complementary AAV9 enables transgene delivery to adult motor neurons", Molecular Therapy, Jul. 2009, vol. 17, No. 7: 1187-1196.
Ellinwood, Matthew N, et al. "Safe, efficient, and reproducible gene therapy of the brain in the dog models of Sanfilippo and Hurler syndromes", Molecular Therapy, Feb. 2011, vol. 19, No. 2: 251-259.
Foust, Kevin D. et al. "Intravascular AAV9 preferentially targets neonatal neurons and adult astrocytes in CNS", Nat Biotechnol., Jan. 2009; 27(1): 59-65.
Fraser, J., et al., "Sleep disturbance in Sanfilippo syndrome: a parental questionnaire study", Arch Dis Child, 2005, 90:1239-1242.
Fu, H., et al., "Significantly increased lifespan and improved behavioral performances by rAAV gene delivery in adult mucopolysaccharidoses IIIB mice", Gene Therapy, 2007, 14: 1065-1077.
Fu, Haiyan et al., "Neurological correction of lysosomal storage in a mucopolysaccharidosis IIIB mouse model by adeno-associated virus-mediated gene delivery", Molecular Therapy, Jan. 2002, vol. 5, No. 1: 42-49.
Fu, Haiyan, et al., "Correction of Neurological Disease of Mucopolysaccharidosis IIIB in Adult Mice by rAAV9 Trans-Blood-Brain Barrier Gene Delivery", Molecular Therapy, 2011, 1-9.
Fu, Haiyan, et al., "Restoration of central nervous system α-N-acetylglucosaminidase activity and therapeutic benefits in mucopolysaccharidosis IIIB mice by a single intracisternal recombinant adeno-associated viral type 2 vector delivery", J Gene Med, 2010; 12: 624-633.
Gungor, N. et al., "Sanfilippo disease type B: a case report and review of the literature on recent advances in bone marrow transplantation", The Turkish Journal of Pediatrics, 1995, 37: 157-163.
Haurigot Virginia et al., "Toward a gene threapy for neurological and somatic MPSIIIA" Rare Diseases, 2013, le27209: 1-6.
Hauswirth, William W. et al., "Treatment of Leber Congenital Amaurosis due to RPE65 mutations by ocular subretinal injection of adeno-associated virus gene vector: short-term results of a phase I trial", Human Gene Therapy, Oct. 2008, 19: 979-990.
Heldermon, Coy D et al., "Therapeutic efficacy of bone marrow transplant, intracranial AAV-mediated gene therapy, or both in the mouse mmodel of MPS IIIB", Molecular Therapy, May 2010, vol. 18, No. 5: 873-880.
Hemsley, K.M. et al., "Effect of high dose repeated intra-cerebrospinal fluid injection of sulphamidase on neuropathology in mucopolysaccharidosis type IIIA mice", Genes, Brain and Behavior, 2008, 7: 740-753.
Hendriksz, C. et al., "Guidelines for the investigation and management of mucopolysaccharidosis type III", MPS Society, www.mpssociety.co.uk, document uploaded Jan. 2012: 1-13.
Hoogerbrugge,P.M. et al., "Allogenic bone marrow transplantation for lysosomal storage diseases", The Lancet, 1995; 345: 1398-1402.
International Search Report for PCT/EP2015/060604; dated Sep. 24, 2015.
Jakobkiewicz-Banecka, Joanna et al., "Genistein-mediated inhibition of glycosaminoglycan synthesis, which corrects storage in cells of patients suffering from mucopolysaccharidoses, acts by influencing an epidermal growth factor-dependent pathway", Journal of Biomedical Science, 2009, 16: 26-34.
Lange, Marcos C. et al., "Bone marrow transplantation in patients with storage diseases", Arq. Neuropsiquiatr., 2006, 64(1): 1-4.
Löser, Peter, et al., "Reactivation of the previously silenced cytomegalovirus major immediate-early promoter in the mouse liver involvement of NFkB", Journal of Virology, Jan. 1998, vol. 72, No. 1: 180-190.
Maguire, Albert M. et al., "Safety and efficacy of gene transfer for Leber's Congenital Amaurosis", N. Engl. J. Med., May 22, 2008, 358(21): 2240-2248.
Malinowska, Marcelina et al., "Genistein improves neuropathology and behavior in a mouse model of neurodegenerative metabolic disease", PLoS ONE, Dec. 2010, 5(12): e14192: 1-9.
Malinowska, Marceline et al., "Genistein reduces lysosomal storage in mucopolysaccharide IIIB mice", Molecular Genetics and Metabolism, 2009, 98: 235-242.
McCarty, D.M. et al., "Mannitol-facilitated CNS entry of rAAV2 vector significantly delayed the neurological disease progression in MPS IIIB mice", Gene Therapy, 2009, 16: 1340-1352.
Meikle, Peter J. et al., "Prevalence of lysosomal storage disorders", JAMA, Jan. 20, 1999, vol. 281, No. 3: 249-254.
Moog, Ute et al., "Is Sanfilippo type B in your mind when you see adults with mental retardation and behavioral problems?", Am. J. Med. Genet Part C Semin Med Genet, 2007, 145C: 293-301.
Muenzer, Joseph et al., "A phase II/III clinical study of enzyme replacement therapy with idursulfase in mucopolysaccharidosis II (Hunter syndrome)", Genetics in Medicine, Aug. 2006, vol. 8, No. 8: 465-473.
Nathwani, Amit C. et al., "Adenovirus-associated virus vector-mediated gene transfer in hemophilia B" N. Engl. J. Med., Dec. 22, 2011, 265(25): 2357-2365.
Neufeld, Elizabeth F. et al., "The mucopolysaccharidoses", The Online Metabolic & Molecular Bases of Inherited Disease (www.ommbid.com) Part 16/Lysosomal Disorders, 2001, 3421-3452.
Niemeyer, Glenn P. et al., "Long-term correction of inhibitor-prone hemophilia B dogs treated with liver-directed AAV2-mediated factor IX gene therapy" Blood, 2009; 113: 797-806.
Peters, C. et al., Hematopoietic cell transplantation for inherited metabolic diseases: an overview of outcomes and practice guidelines Bone Marrow Transplantation, 2003, 31: 229-239.
Peters, Charles et al., "Outcome of unrelated donor bone marrow transplantation in 40 children with Hurler syndrome", Blood, 1998, vol. 87, No. 11: 4894-4902.
Piotrowska, Ewa et al., "Genistein rich soy isoflavone extract in substrate reduction therapy for Sanfilippo syndrome: an open-label, pilot study in 10 pediatric patients", Current Therapeutic Research, Apr. 2008, vol. 69, No. 2: 166-179.
Piotrowska, Ewa et al., "Genistein-rnediated inhibition of glycosaminoglycan synthesis as a basis for gene expression-targeted isoflavone therapy for mucopolysaccharidoses", European Journal of Human Genetics, 2006, 14: 846-852.
Rivera, Victor M. et al., "Long-term pharmacologically regulated expression of erythropoietin in primates following AAV-mediated gene transfer", Blood, Feb. 15, 2005, vol. 105, No. 4: 1424-1430.
Roberts, Ainslie L.K. et al., "Improvement in behaviour after substrate deprivation therapy with rhodamine B in a mouse model of MPS IIIA", Molecular Genetics and Metabolism, 2007, 92: 115-121.
Robertson, S.P. et al., "Cerebrospinal fluid shunts in the management of behavioural problems in Sanfilippo syndrome (MPS III)", Eur. J. Pediatr., 1998, 157: 653-655.
Rovelli, AM, "The controversial and changing role of haematopoietic cell transplantation for lysosomal storage disorders: an update", Bone Marrow Transplantation, 2006, 41: S87-S89.
Savas, Peter S. et al., "Intracerebral injection of sulfamidase delays neuropathology in murine MPS-IIIA", Molecular Genetics and Metabolism, 2004, 82: 273-285.
Sivakumur, P. et al., "Bone marrow transplantation in a mucopolysaccharidosis type IIIA: A comparison of an early treated patient with his untreated sibling", J. Inher. Metab. Dis., 1999, 22: 849-850.
Souweidane, Mark M. et al., "Gene therapy for late infantile neuronal ceroid lipofuscinosis neurosurgical considerations", J. Neurosur. Pediatr., Aug. 2010, 6(2): 115-122.
Valstar, Marlies J. et al., "Mucopolysaccharidosis Type IIIA: Clinical spectrum and genotype-phenotype correlations", Ann. Neurol., 2010, 68: 876-887.
Van De Kamp, J.J.P. et al., "Genetic heterogeneity and clinical variability in the Sanfilippo syndrome (types A, B, and C)", Clinical Genetics, 1981, 20: 152-160.
Vellodi, A. et al., "Bone marrow transplantation for Sanfilippo disease type B", J. Inher. Metab. Dis., 1992, 15: 911-918.
Willing, Alison E. et al., "Repeated administrations of human umbilical cord blood cells improve disease outcomes in a mouse model of Sanfilippo syndrome type III B", Cell Transplantation, 2014, vol. 23: 1613-1630.

(56) References Cited

OTHER PUBLICATIONS

Yamada, Y. et al., "Treatment of MPS VII (Sly disease) by allogeneic BMT in a female with homozygous A619V mutation", Bone Marrow Transplantation, 1998, 21: 629-634.
Yu, Wei-Hong et al., "Short-term enzyme replacement in the murine model of Sanfilippo syndrome type B", Molecular Genetics and Metabolism, 2000, 71: 573-580.
Hale, et al. Protein Expression and Purification, vol. 12:185-188, 1998.

* cited by examiner

HDTV – Human NAGLU

HDTV – Codon-optimized human NAGLU version2

HDTV – Codon-optimized human NAGLU version3

Figure 12

IC – Codon-optimized murine NAGLU

A

| Brain Section (I, II, III, IV, V) | Vector genomes /diploid genome | |
|---|---|---|
| | *Males* | *Females* |
| I | 0.14 ± 0.04 | 0.13 ± 0.03 |
| II | 0.09 ± 0.01 | 0.12 ± 0.04 |
| III | 0.13 ± 0.04 | 0.19 ± 0.10 |
| IV | 1.61 ± 0.73 | 0.80 ± 0.55 |
| V | 0.94 ± 0.15 | 1.35 ± 0.74 |
| Spinal cord | 0.14 ± 0.07 | 0.07 ± 0.02 |

B

| Tissue | Vector genomes /diploid genome | |
|---|---|---|
| | *Males* | *Females* |
| Liver | 0.78 ± 0.33 | 0.72 ± 0.33 |
| Spleen | 0.03 ± 0.02 | 0.02 ± 0.01 |
| Heart | 0.01 ± 0.00 | 0.01 ± 0.01 |
| Kidney | 0.01 ± 0.00 | 0.01 ± 0.00 |
| Lung | 0.01 ± 0.00 | 0.01 ± 0.00 |
| Adrenal gland | 0.04 ± 0.01 | 0.10 ± 0.01 |
| Mandibular lymph node | 0.12 ± 0.02 | 0.12 ± 0.02 |
| Inguinal lymph node | 0.01 ± 0.00 | 0.02 ± 0.01 |
| White adipose tissue | 0.02 ± 0.00 | 0.03 ± 0.01 |
| Bone marrow | *ND* | *ND* |
| Skin | 0.01 ± 0.00 | *ND* |
| Thymus | *ND* | *ND* |
| Skeletal muscle | *ND* | *ND* |
| Intestine | *ND* | *ND* |
| Pancreas | *ND* | *ND* |
| Urinary bladder | *ND* | *ND* |
| Epidydimus | *ND* | *ND* |
| Testicle | *ND* | *ND* |
| Oviduct | *ND* | *ND* |

Figure 14
IC – Codon-optimized murine NAGLU
A
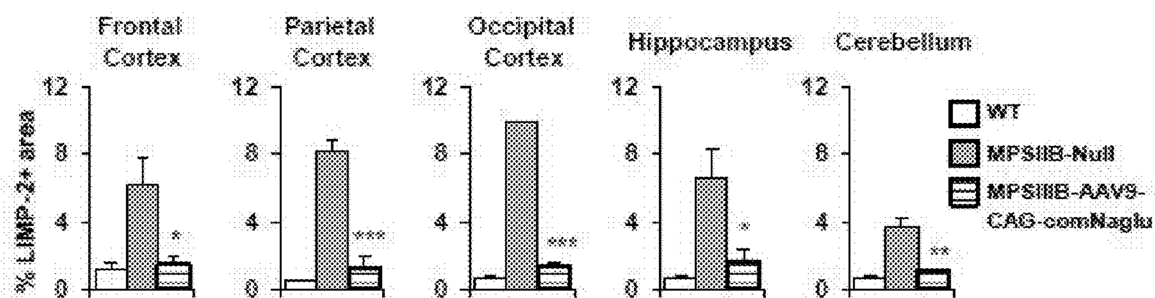
B
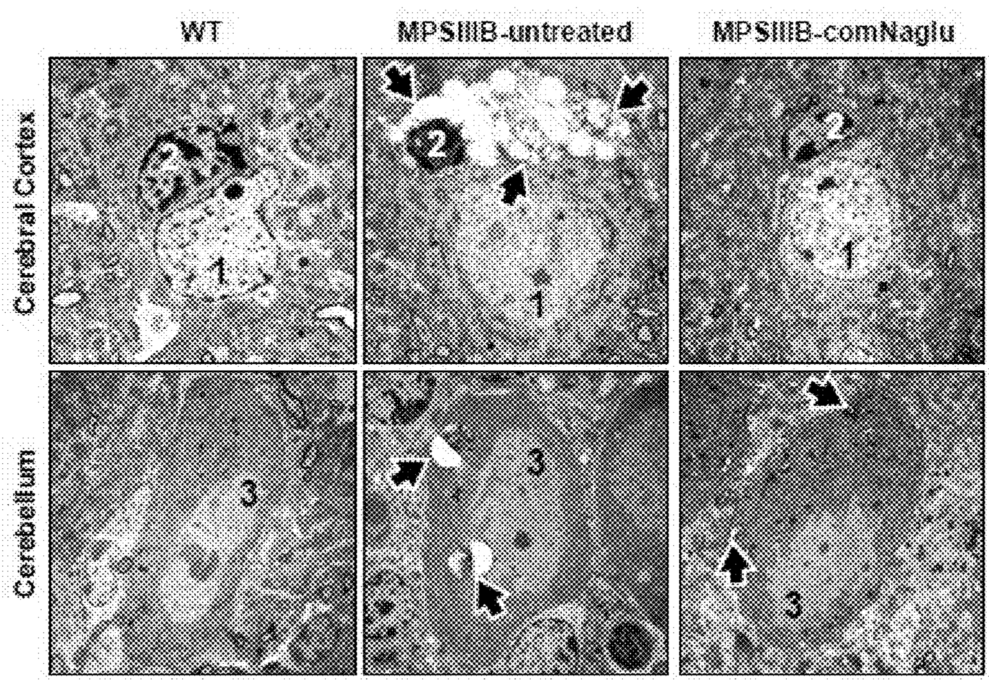
C
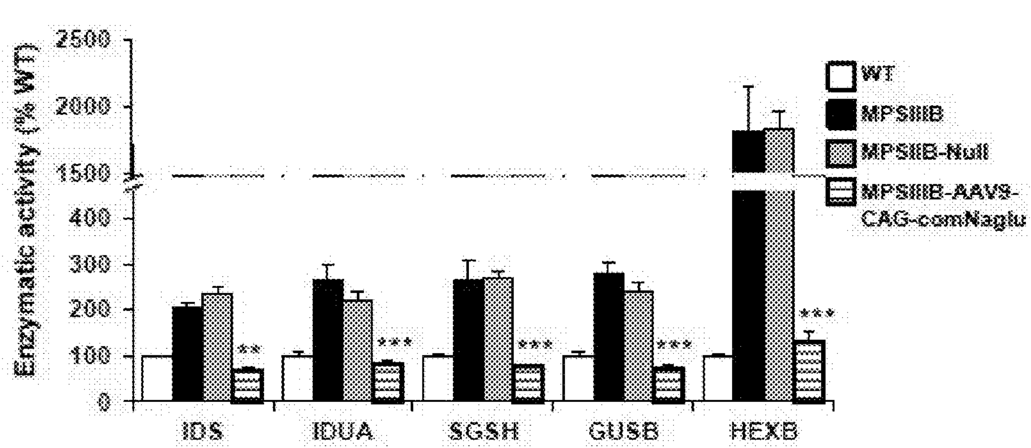

Figure 15
IC – Codon-optimized murine NAGLU
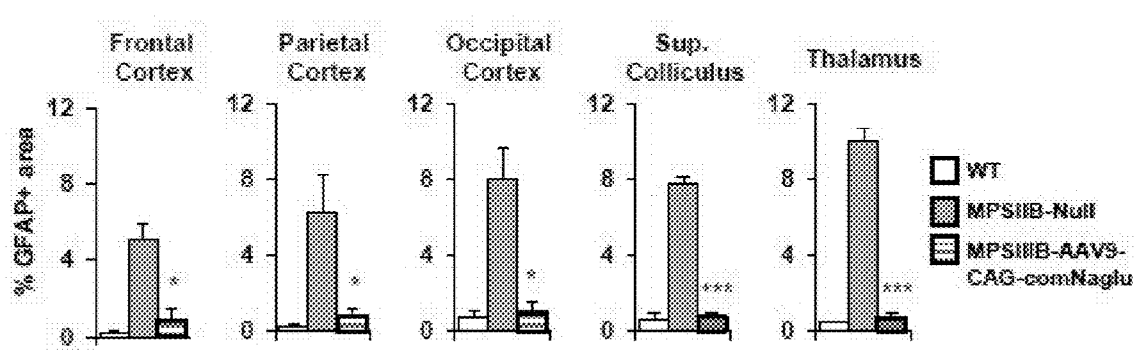
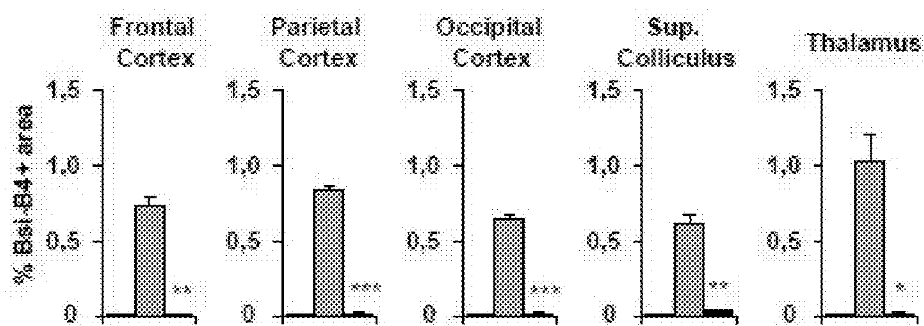
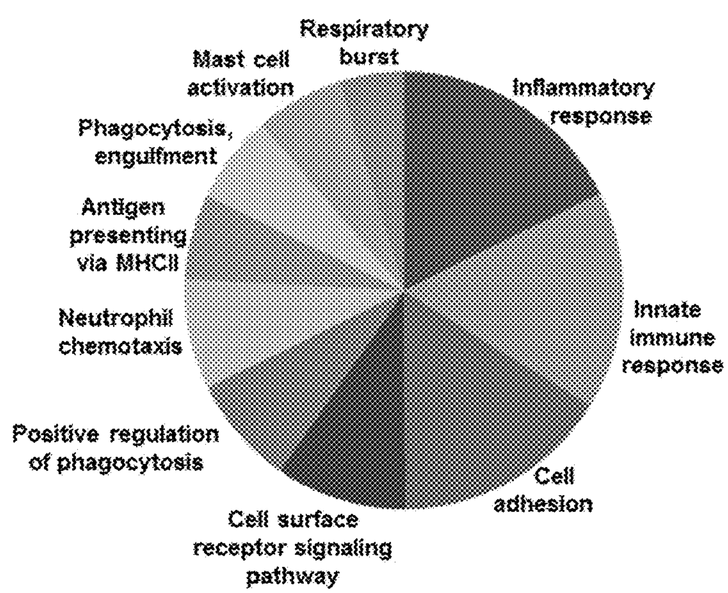

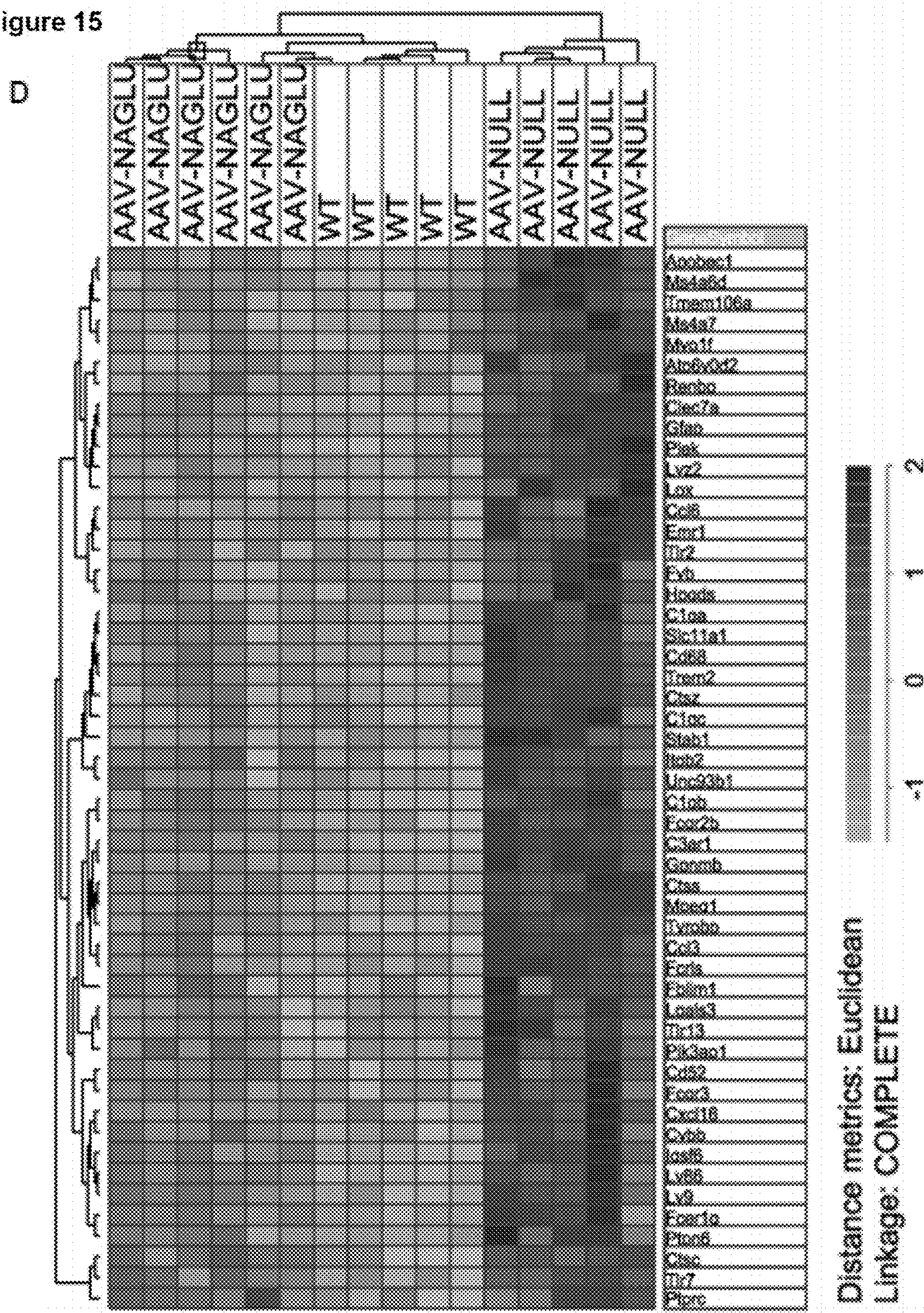
Figure 15
D
AAV-NAGLU
AAV-NAGLU
AAV-NAGLU
AAV-NAGLU
AAV-NAGLU
AAV-NAGLU
WT
WT
WT
WT
WT
AAV-NULL
AAV-NULL
AAV-NULL
AAV-NULL
AAV-NULL
Apobec1
Ms4a6d
Tmem106a
Ms4a7
Myo1f
Atp6v0d2
Renbp
Clec7a
Gfap
Plek
Lyz2
Lox
Ccl6
Emr1
Tlr2
Fyb
Hcods
C1qa
Slc11a1
Cd68
Trem2
Ctsz
C1qc
Stab1
Itgb2
Unc93b1
C1qb
Fcgr2b
C3ar1
Gpnmb
Ctss
Mpeg1
Tyrobp
Ccl3
Fcrls
Fblim1
Lgals3
Tlr13
Pik3ap1
Cd52
Fcgr3
Cxcl16
Cybb
Igsf6
Ly86
Ly9
Fcgr1a
Ptpn6
Ctsc
Tlr7
Ptprc
2
1
0
-1
Distance metrics: Euclidean
Linkage: COMPLETE IC – Codon-optimized murine NAGLU
A
Liver
Naglu Activity (% WT)
1200
1000
800
600
400
200
0
nd
nd
***
B
Serum
Naglu Activity (% WT)
***
WT
MPSIIIB
MPSIIB-Null
MPSIIIB-AAV9-CAG-comNaglu
C
Liver
Spleen
Heart
Lung
Kidney
µg GAG/mg of tissue
***
**
$
D
WT
MPSIIIB-Null
MPSIIIB-comNaglu
Liver
E
Lysosomal enzymatic activities in liver
Enzymatic activity (% WT)
2500
2000
1500
400
300
200
100
0
IDS
IDUA
SGSH
GUSB
GALNS
HEXB IC – Codon-optimized murine NAGLU IC – Codon-optimized canine NAGLU

A

| Anti-AAV9 Neutralizing antibodies | | | | | | | | |
|---|---|---|---|---|---|---|---|---|
| | Non-immunized dogs | | | | Immunized dogs | | | |
| | Dog 1 | | Dog 2 | | Dog 3 | | Dog 4 | |
| Week | Serum | CSF | Serum | CSF | Serum | CSF | Serum | CSF |
| W -6 | - | - | - | - | 1:1 | - | 1:1 | - |
| W -5 | - | - | - | - | >1:316 | - | >1:316 | - |
| W -1 | - | - | - | - | 1:100 | - | 1:100 | - |
| W 0 | <1:1 | 1:1 | <1:1 | 1:1 | 1:100 | 1:1 | 1:1000 | 1:1 |
| W 1 | >1:31,6 | 1:1 | >1:31,6 | 1:1 | 1:10000 | 1:1 | 1:1000 | 1:1 |

B

Human Naglu

Codon-optimized human Naglu

A

B

Codon-optimized human Naglu version2

Figure 22
Codon-optimized human Naglu version3
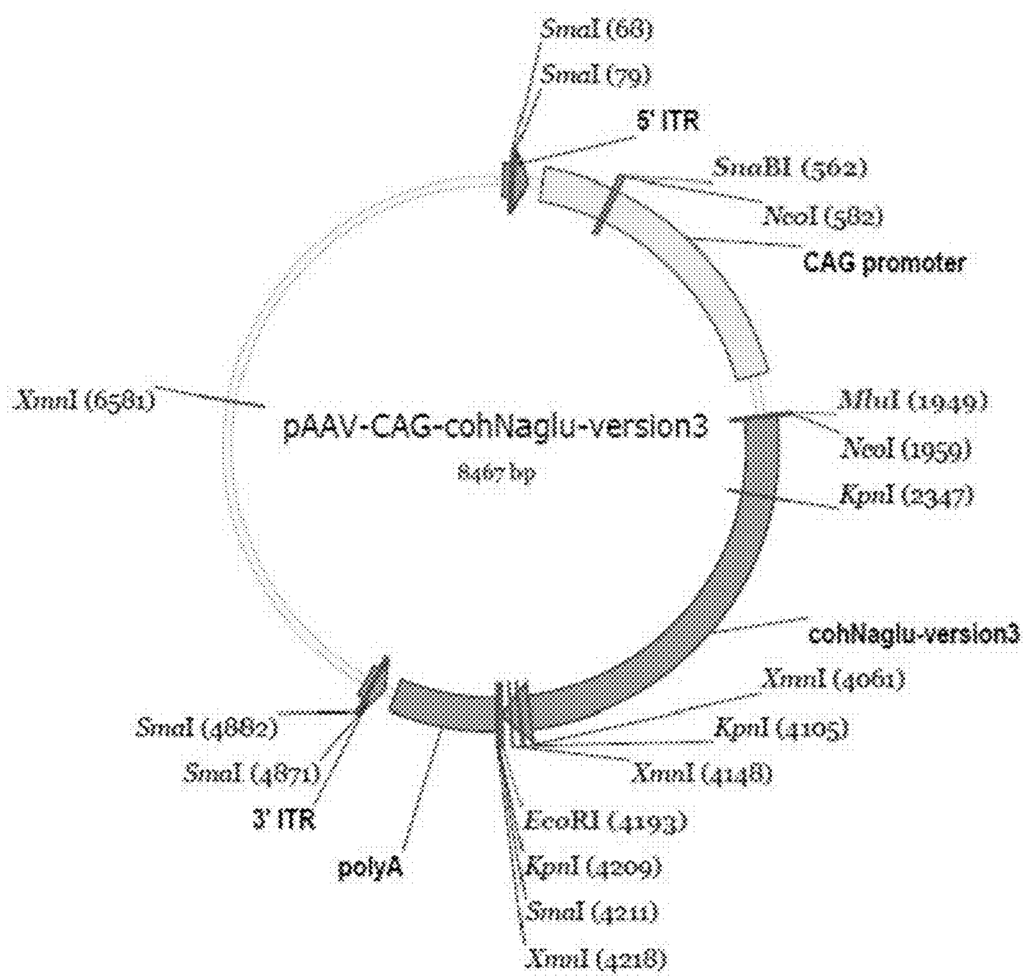
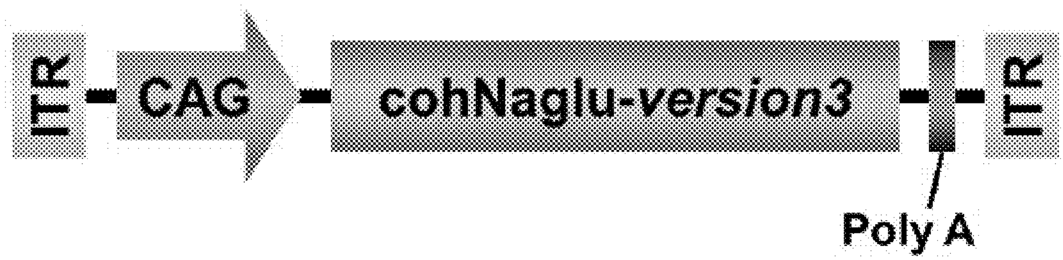

Codon-optimized murine Naglu

A

B

Codon-optimized canine Naglu

A

B

ITR — CAG — cocNaglu — Poly A — ITR

ADENOASSOCIATED VIRUS VECTORS FOR THE TREATMENT OF LYSOSOMAL STORAGE DISORDERS

FIELD OF THE INVENTION

The present invention relates to vectors useful for the expression of proteins of interest and their utilization in gene therapy. The present invention also relates to vectors and nucleic acid sequences helpful for the treatment of mucopolysaccharidoses (MPS), and in particular, for the treatment of mucopolysaccharidoses type III-B or Sanfilippo B syndrome.

BACKGROUND OF THE INVENTION

The lysosome is an organelle found in the cytoplasm of animal cells that contains more than 50 hydrolases that break down biomolecules during the recycling of worn-out cellular components or after the engulfment of viruses and bacteria. This organelle contains several types of hydrolytic enzymes, including proteases, nucleases, glycosidases, lipases, phospholipases, phosphatases and sulfatases. All enzymes are acid hydrolases.

Lysosomal storage diseases (LSDs) are caused by genetic defects that affect one or more lysosomal enzymes. These genetic diseases result generally from a deficiency in a particular enzyme activity present in the lysosome. To a lesser extent, these diseases may be due to deficiencies in proteins involved in lysosomal biogenesis.

LSDs are individually rare, although as a group these disorders are relatively common in the general population. The combined prevalence of LSDs is approximately 1 per 5,000 live births. See Meikle P, et al., JAMA 1999; 281: 249-254. However, some groups within the general population are particularly afflicted by a high occurrence of LSDs. For instance, the prevalence of Gaucher and Tay-Sachs diseases in descendants from Jewish Central and Eastern European (Ashkenazi) individuals is 1 per 600 and 1 per 3,900 births, respectively.

Type III mucopolysaccharidoses (MPSIII), known collectively as Sanfilippo syndrome, are LSDs caused by deficiency in one of the enzymes involved in the stepwise degradation of the glycosaminoglycan (GAG) heparan sulfate (HS), leading to its pathological accumulation. MPSIII is classified into four subtypes depending on the enzyme deficiency. Loss of N-acetylglucosaminidase, alpha enzymatic activity causes subtype IIIB The resulting disease is characterized clinically as a childhood-onset progressive neuropathy of the CNS. The clinical course can generally be divided into three phases. In the first phase of the disease, after a symptom-free period that spans the first months of life, a slowing of mental development becomes apparent. This is followed by severe behavioral problems and progressive intellectual decline during the second phase of the disease. Finally, with the onset of severe dementia, the behavioral problems slowly disappear, and all motor functions start to decline, eventually resulting in dysphagia, complete loss of locomotion and pyramidal tract lesions. In addition to the neurological symptoms, MPSIIIB patients suffer non-neurological alterations, including recurrent ear, nose, throat and chest infections, frequent diarrhea and constipation, progressive joint degeneration and skeletal abnormalities which affect mobility, as well as hepato and splenomegaly. See Cleary and Wraith, Arch Dis Child. 1993; 69 (3):403-6, Neufeld and Muenzer, "The Mucopolysaccharidoses" in Scriver C, et al., Eds., "The metabolic and molecular basis of inherited disease", McGraw-Hill Publishing Co., New York, N.Y., US, 2001, pp. 3421-3452, van de Kamp et al., Clin Genet. 1981; 20(2):152-60, Moog et al, Am J Med Genet C Semin Med Genet. 2007; 145C(3):293-301. Patients usually die at the end of the second or beginning of the third decade of life. See Neufeld and Muenzer, supra. A more slowly progressive form of the disease with later onset and longer survival, known as the attenuated phenotype, has been described in a subset of MPSIIIB patients. See Moog et al., supra and Valstar et al., Ann Neurol. 2010; 68(6):876-87.

There is currently no available treatment for MPSIIIB Therefore, the control of the disease is symptomatic and aimed at improving the quality of life of patients and their families. This is of special importance for those symptoms arising from CNS alterations. For example, intermittently raised intracranial pressure is a recognized cause of behaviour disturbance and it is not uncommon in MPSs. See Muenzer et al., Genet Med. 2006; 8(8):465-73. The thickening of the meninges due to mucopolysaccharide deposition would be the underlying cause for the raising of cerebrospinal fluid (CSF) pressure. Thus, when behavioural alterations are refractory to conventional medication, the insertion of a cerebrospinal fluid shunt is considered in order to alleviate the pressure. Neurological symptoms improved significantly in six Sanfilippo patients who had cerebrospinal shunts inserted. See Robertson et al., Eur J Pediatr. 1998; 157(8):653-5. On the other hand, melatonin administration is considered to be the best treatment for the sleep disorders characteristic of the disease, although it is not completely effective. See Fraser et al., Arch Dis Child. 2005; 90(12): 1239-42. There is no specific treatment for the somatic pathology either, and only palliative therapies can be applied to each individual symptom.

New therapeutic approaches to MPSIIIB are being tested with different degrees of success. Substrate deprivation therapy (SDT) aims at reducing the rate of GAG synthesis, so that, if any residual enzymatic activity remains, excessive accumulation of GAGs is prevented or at least the rate of accumulation is slowed down. Genistein, a soybean isoflavone, has been suggested to act as an inhibitor of HS production by decreasing the kinase activity of the Epidermal Growth Factor receptor (EGFR). See Jakobkiewicz-Banecka et al., J Biomed Sci. 2009; 16:26, Piotrowska et al., Eur J Hum Genet. 2006; 14(7):846-52. Recent studies indicate that genistein inhibits synthesis of GAGs in fibroblasts of patients suffering from various mucopolysaccharidoses (types I, II, III-A and III-B) See Piotrowska et al., supra. Short-term and long-term oral administration of genistein to a mouse model of MPSIIIB disease resulted in reduction of storage and better performance in motor skills tests. See Malinowska et al., Mol Genet Metab. 2009; 98(3):235-42, Malinowska et al., PLoS One. 2010; 5(12): e14192. When administered intravenously, genistein is expected to be able to cross the blood-brain barrier (BBB), permitting the treatment of the CNS pathology. Supporting this notion, an open label pilot study in which a genistein-enriched soybean extract was administered to 5 MPSIIIA and 5 MPSIIIB patients for 12 months resulted in a significant amelioration of both somatic and neurological parameters. See Piotrowska et al., Current Therapeutic Research. 2008; 69(2):166-179. However, subsequent studies did not show improvement in either the disability scales or the behaviour scores of MPSIIIA, MPSIIIB or MPSIIIC patients treated with genistein for 12 months. See Delgadillo et al., J Inherit Metab Dis. 2011; 34(5):1039-44, study NTR #1826 registered at The Netherlands National Trial Register and de Ruijter et al., Ann Neurol. 2012; 71(1):110-20. Another molecule, rhodamine B, has also proven to be effective in decreasing GAG accumulation in preclinical studies, with an efficacy similar to that observed with genistein. See Hendriksz et al., "Guidelines for the investigation and Management of Mucopolysaccharidosis type III", 2012, available at www.mpssociety.co.uk. Rhodamine B is thought to suppress the synthesis of GAG chains by inhibiting the formation of sugar precursors and/or the activity of glycosyl transferases. See Roberts et al., Mol Genet Metab. 2007; 92(1-2):115-21.

Normal cells secrete significant amounts of mannose-6-phosphate (M6P)-tagged lysosomal enzymes, which can be subsequently taken up by other cells via M6P receptors on the plasma membrane. This opens the possibility of treating LSDs caused by deficiency of soluble hydrolases by infusing the correct version of the missing enzyme. Although enzyme replacement therapy (ERT) is yet not available for Sanfilippo B patients, the intravenous administration of recombinant N-acetylglucosaminidase, alpha to 3-month-old MPSIIIB mice showed that the recombinant enzyme distributed to several organs, mainly to the liver. An insignificant amount of enzyme was detected in the brain, which was attributed to the presence of the BBB that limits the entry of exogenously provided proteins to the brain parenchyma. See Yu et al., Mol Genet Metab. 2000; 71(4):573-80 and Hendriksz et al, supra. There is an early development program for an ERT product for the treatment of neurologic disease in MPSIIIB patients. The HGT-3010 program (Shire) is an ERT based on intrathecal delivery of recombinant enzyme, and is nowadays in preclinical phase. Direct delivery of ERT to the CNS has reduced neurological pathology in MPSIIIA mice and is currently being tested in MPSIIIA patients. See Hemsley K, et al., Genes Brain Behav. 2008; 53(2):161-8, Savas P, et al., Mol Genet Metab. 2004; 82:273-285, NCT01155778 and NCT01299727 at www.clinicaltrials.gov. However, the implantation of the permanent intrathecal delivery device that the therapy requires is associated with substantial risks and shortcomings, and the therapy itself has a very high economic cost per patient/year.

Hematopoietic stem cell transplantation (HSCT) using bone marrow-derived stem cells (Bone marrow transplantation, BMT) has proven efficient in the treatment of both somatic and neurological pathology in patients with other MPSs See Peters et al., Blood 1996; 87(11):4894-902, Peters and Steward, Bone Marrow Transplant 2003; 31(4):229-39 and Yamada et al., Bone Marrow Transplant 1998; 21(6):629-34. Donor-derived myeloid cells are able to cross the BBB, enter the brain parenchyma, and differentiate into microglial cells that secrete the missing lysosomal enzyme, which is then taken up by surrounding cells leading to correction of GAG accumulation in the brain. See Krivit et al., Cell Transplant. 1995; 4(4):385-92. However, no clear benefit has been observed in Sanfilippo A or B patients who have undergone BMT. See Hoogerbrugge et al., Lancet 1995; 345(8962):1398-402, Vellodi et al., J Inherit Metab Dis. 1992; 15(6):911-8, Güngör and Tuncbilek, Turk J Pediatr. 1995; 37(2):157-63, Sivakumur and Wraith, J Inherit Metab Dis. 1999; 22(7):849-50 and Lange et al., Arq Neuropsiquiatr. 2006; 64(1):1-4. The main reason for BMT failure seems to be the slow pace of replacement of the microglial population by the hematopoietic cell progeny compared to the quick progression of the primary disease. See Rovelli, Bone Marrow Transplant 2008; 41 Suppl 2:S87-9. Therefore, HSCT using BMT is currently not considered as a treatment option for MPSIII patients. See Boelens et al., Pediatr Clin North Am. 2010; 57(1):123-145. HSCT using umbilical cord blood-derived stem cells improved the cognitive outcome in MPSIIIB mice but required repeated cell administration. See Willing et al., Cell Transplantation 2013; epub ahead of print. This approach has recently been used to transplant several children with MPSIIIA and MPSIIIB; it is yet unclear whether it results in protection of the CNS from degeneration. See de Ruijter et al., Curr Pharm Biotechnol. 2011; 12(6):923-30.

Given the limitations of current therapeutic options for MPSIII, and particularly for MPSIIIB, alternative approaches are needed. In vivo gene therapy offers the possibility of a one-time treatment for MPS IIIB and other inherited diseases, with the prospect of lifelong beneficial effects. Several gene therapy approaches based on the use of different viral vectors combined with different routes of administration have been tested in animal models of MPSIIIB disease.

Lentiviral vectors coding for the human N-acetylglucosaminidase, alpha gene have been administered intravenously to young MPSIIIB mice, resulting in low levels of transgene expression in liver, spleen, lung and heart, which reduced but did not normalize GAG accumulation in these tissues. See Di Natale et al., Biochem J. 2005; 388(2):639-46. The therapeutic potential of lentiviral vectors has also been tested by direct delivery of vectors to the brain parenchyma via intracranial administration. See Di Domenico et al., Am J Med Genet A. 2009; 149A(6):1209-18. MPSIIIB mice administered at a single brain site showed increased N-acetylglucosaminidase, alpha activity up to 6 months after treatment, which only partially corrected lysosomal storage lesions.

Adenoassociated virus (AAV) vector-mediated gene transfer, in particular, is rapidly emerging as the approach of choice for many in vivo gene therapy applications, due to the high transduction efficiency and the lack of pathogenicity of these vectors. AAV vectors can transduce post-mitotic cells and several pre-clinical and clinical studies have demonstrated the potential of AAV vector-mediated gene transfer to efficiently drive sustained expression of therapeutic transgenes for a variety of diseases. See Bainbridge et al., N Engl J Med. 2008; 358(21):2231-9, Hauswirth et al., Hum Gene Ther. 2008; 19(10):979-90, Maguire et al., N Engl J Med. 2008; 358(21):2240-8, Niemeyer et al., Blood 2009; 113(4):797-806, Rivera et al., Blood 2005; 105(4):1424-30, Nathawani et al., N Engl J Med. 2011; 365(25):2357-65 and Buchlis et al., Blood 2012; 119(13):3038-41.

When AAV vectors of serotype 2 coding for human N-acetylglucosaminidase, alpha were delivered to the brain parenchyma of MPSIIIB mice at a single location, N-acetylglucosaminidase, alpha expression and activity were restricted to the site of injection and only partial amelioration of the disease phenotype was achieved. See Fu et al., Mol Ther. 2002; 5(1):42-9, Cressant et al., J Neurosci. 2004; 24(45):10229-39. AAV2 vectors delivered intravenously to MPSIIIB mice following pre-treatment with mannitol to permeate the BBB, led to significantly extended survival, improved behavioural performance, and reduction of brain lysosomal pathology, although only partial correction of somatic disease was achieved. See McCarty et al., Gene Ther. 2009; 16(11):1340-52. On the other hand, a single administration of AAV2 vectors to the cerebrospinal fluid (CSF) by intracisternal injection led to restoration of N-acetylglucosaminidase, alpha activity and reduction of GAGs in the MPSIIIB mouse brain, although no detectable N-acetylglucosaminidase, alpha activity was observed in somatic tissues. See Fu et al., J Gene Med. 2010; 12(7):624-33. A combined therapy involving intracisternal and intravenous delivery of AAV2 has demonstrated significant long-term therapeutic efficacy in the CNS as well as partial somatic correction. See Fu et al., Gene Ther. 2007; 14(14): 1065-77.

Other studies have taken advantage of the high tropism for neuronal cells shown by serotype 5 AAV vectors following intraparenchymal administration. These vectors have, however, a low distribution within the brain parenchyma, and the approach requires multiple injections. The delivery of AAV5 vectors to multiple sites of the brain of newborn MPSIIIB mice in combination with bone marrow transplantation, showed therapeutic efficacy similar to that obtained with serotype 2 vectors. See Heldermon et al., Mol Ther. 2010; 18(5):873-80. In animal models of larger brain size, the stereotactic administration of AAV5 vectors to four different brain locations in MPSIIIB dogs led to the detection of active N-acetylglucosaminidase, alpha in widespread areas of the brain. However, enzymatic activity remained low or undetectable in the most rostral and most caudal regions, especially in the cerebellum. See Ellinwood et al., Mol Ther. 2011; 19(2):251-9. Lysosomal pathology was improved but not fully corrected in treated MPSIIIB dogs, indicating that the levels of enzymatic activity achieved with this approach were insufficient to cope with GAG storage. Despite this partial efficacy, a clinical trial based on this approach has recently been initiated. See ISRCTN19853672 at ISRCTN register. The larger the brain the more difficult it becomes to cover the whole volume of the organ with intraparenchymal injections, and delivery to humans needs vector administration at several sites, making delivery technically challenging and requiring the development of specific surgical procedures. See Souweidane et al., J Neurosurg Pediatr. 2010; 6(2):115-122.

To date, only one study that uses AAV vectors of serotype 9 for the treatment of MPSIIIB has been reported. The approach takes advantage of the ability of AAV9 vectors to transduce the CNS when systemically administered. See Foust et al., Nat Biotechnol. 2009; 27(1):59-65 and Duque, et al., Mol Ther. 2009; 17(7):1187-1196. The intravenous delivery of AAV9-N-acetylglucosaminidase, alpha vectors to MPSIIIB mice, resulted in correction of lysosomal storage pathology in CNS and somatic organs, improvement of behavioural performance and extension of lifespan. See Fu et al., Mol Ther. 2011; 19(6):1025-33. However, this proposed course of action has several shortcomings. First, the CMV promoter utilized has been reported to silence. See Löser et al., J Virol. 1998 January; 72(1):180-90. Second, therapeutic efficacy was achieved at a very high dose of vector ($\geq 1\times10^{13}$ vg/kg). The use of such high doses would suppose a challenge for clinical translation from the manufacturing and safety points of view.

None of aforementioned approaches has fully restored N-acetylglucosaminidase, alpha activity, achieved full eradication of intracytoplasmic inclusions in the CNS and somatic tissues, or corrected all clinical signs of MPSIIIB Thus, there is a need for novel approaches to the treatment of MPSIIIB that have better efficacy and safety profiles.

SUMMARY OF THE INVENTION

The present invention provides new recombinant vectors for the treatment of diseases, in particular for the treatment of mucopolysaccharidoses type III (MPSIII), especially MPSIIIB A first aspect, the invention relates to adenoassociated virus vectors (AAV) containing a nucleotide sequence coding for N-acetylglucosaminidase, alpha (Naglu) SEQ ID NO: 1. The AAV vectors according to the invention are of serotype 9 (AAV9). These vectors proved to be very efficient to fully revert the pathological GAGs storage in all regions of the brain and somatic tissues.

The AAV9 vectors according to the invention contain a nucleotide sequence coding for Naglu that has at least 80% sequence identity with SEQ ID NO: 2, and preferably at least 84% sequence identity with SEQ ID NO: 2.

The AAV9 vectors of the present invention further contain a promoter linked to the coding nucleotide sequence in order to control the expression of Naglu. A suitable promoter is the CAG promoter, SEQ ID NO: 4.

Another aspect of the invention relates to plasmids containing a nucleotide sequence coding for N-acetylglucosaminidase, alpha (Naglu), and in particular a nucleotide sequence having at least 80% sequence identity with SEQ ID NO: 2 or preferably at least 84% sequence identity with SEQ ID NO: 2.

A further aspect of the present invention relates to a pharmaceutical composition comprising a therapeutically effective amount of the AAV9 vectors of the invention or a plasmid described therein.

The present invention further provides methods useful for delivering polynucletoides, especially Naglu polynucleotides.

Still a further aspect of the invention relates to the AAV9 vectors of the invention or a plasmid described therein for use as a medicament, in particular for the treatment of mucopolysaccharidoses type III (MPSIII), especially MPSIIIB The present invention also provides method for the production of the AAV 9 vectors according to the invention.

In a further aspect the invention relates to isolated cells comprising the nucleotide sequence coding for N-acetylglucosaminidase, alpha (Naglu), and in particular a nucleotide sequence having at least 80% sequence identity with SEQ ID NO: 2 or preferably at least 84% sequence identity with SEQ ID NO: 2.

BRIEF DESCRIPTION OF THE DRAWINGS

FIG. 12. Intracisternal delivery of AAV9 vectors coding for optimized murine N-acetylglucosaminidase, alpha (AAV9-CAG-comNaglu). Biodistribution of vector genomes following the administration to the cisterna magna of MPSIIIB mice of $3\times10^{10}$ vg of AAV9-CAG-comNaglu. Vector genomes were quantified in brain (A) and somatic tissues (B) by quantitative PCR and referred to the quantity of DNA contained in a diploid genome. ND: not detected.

FIG. 14. Intracisternal delivery of AAV9 vectors coding for optimized murine N-acetylglucosaminidase, alpha (AAV9-CAG-comNaglu). (A) Quantification of the signal intensity obtained in different areas of the brain following staining for the lysosomal marker LIMP-2, which gives an indication of the size of the lysosomal compartment, in wild-type (healthy) mice and MPSIIIB mice administered in the cisterna magna with either $3.9\times10^{10}$ vg of control vector (AAV9-Null) or $3\times10^{10}$ vg of AAV9-CAG-comNaglu. Values are means±SEM of 4 mice per group. * P<0.05,  P<0.01, * P<0.001 vs. MPSIIIB-null. (B) Electron microscopy analysis of the cerebral cortex and cerebellum of wild-type (left panels), untreated-MPSIIIB (middle panels) and MPSIIIB mice administered in the cisterna magna with AAV9-CAG-comNaglu (right panels). 1. neurons; 2. perineuronal glial cells; 3. purkinje neurons. (C) Activity of other lysosomal enzymes in brain extracts obtained from wild-type (WT) mice, untreated MPSIIIB mice (MPSIIIB) and MPSIIIB mice administered in the cisterna magna with either $3.9\times10^{10}$ vg of control vector (AAV9-Null) or $3\times10^{10}$ vg of AAV9-CAG-comNaglu. SGSH, N-sulfoglucosamine sulfohydrolase, GUSB, glucuronidase, beta, HEXB, hexosaminidase B. WT enzyme activities were set to 100%. Values are means±SEM of 4 mice per group. *** P<0.001 vs. MPSIIIB-Null.

FIG. 15. Intracisternal delivery of AAV9 vectors coding for optimized murine N-acetylglucosaminidase, alpha (AAV9-CAG-comNaglu). Histograms represent the signal intensity measured following immunostaining for the astrocyte marker GFAP (A) and for the microglial marker BSI-B4 (B) in sections of frontal, parietal, and occipital cortex, superior colliculus, and thalamus from wild-type (healthy) mice, and MPSIIIB mice administered in the cisterna magna with either $3.9\times10^{10}$ μg of control vector (AAV9-Null) or $3\times10^{10}$ vg of AAV9-CAG-comNaglu. Values are means±SEM of 2-3 mice per group. * P<0.05,  P<0.01, * P<0.001 vs. MPSIIIB-null. (C) Functional categorization based on Gene Ontology (GO) annotation. Pie chart indicating the fraction of transcripts associated with each biological process term. Clearly, most of the terms represent inflammation/immunity-related categories. (D) Hierarchical clustering of all experimental groups based on the set of genes that the CTEN software assigned to be representative of microglia. Each column represents a gene and each row represents an animal. The level of expression of each gene is depicted relative to the mean abundance for that gene across all samples in a grey scale shown at the bottom. The dendrogram of samples shown above the matrix represents overall similarities in transcript levels. Clearly, all MPSIIIB mice treated with AAV9-CAG-comNaglu have a gene expression profile close to that of healthy, age-matched WT littermates.

FIG. 22. Schematic representation of the plasmid pAAV-CAG-cohNaglu-version3 (A) and schematic representation of the genome of the recombinant AAV vector AAV9-CAG-cohNaglu-version3 (B).

DEPOSIT OF MICROORGANISMS

Figure 1:
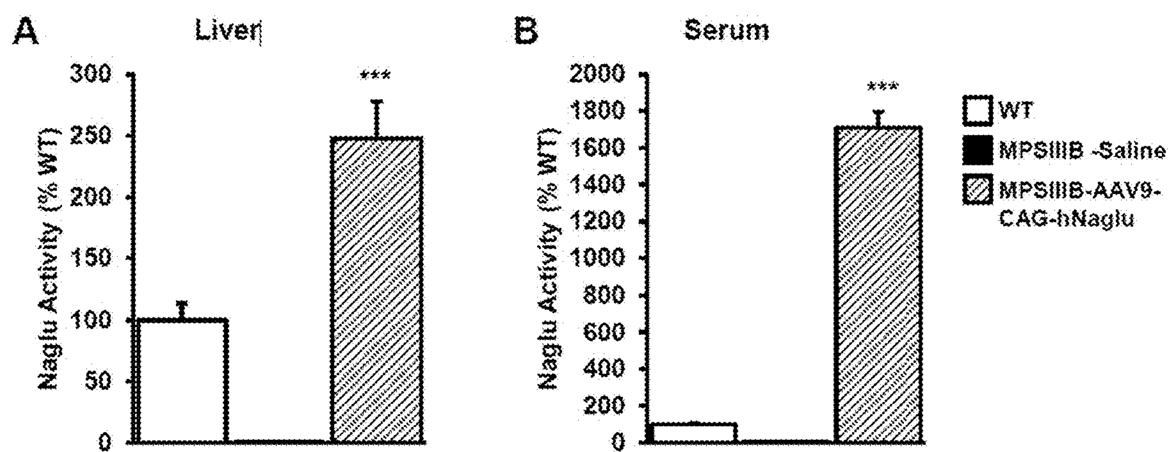
FIG. 1. Hydrodynamic delivery of plasmids encoding for human N-acetylglucosaminidase, alpha (pAAV-CAG-hNaglu). Two month-old MPSIIIB mice were hydrodynamically injected with 50 μg of the plasmid pAAV-CAG-hNaglu. Histograms depict N-acetylglucosaminidase, alpha (NAGLU) activity measured 1 week post plasmid administration in liver (A) and serum (B). NAGLU activity of saline-injected WT mice was set to 100%. Values are means±SEM of 3-4 mice per group. *** P<0.001 vs. WT.

The plasmid pAAV-CAG-cohNaglu (SEQ ID NO: 6) was deposited on Nov. 13, 2012, under access number DSM 26626 at the DSMZ—Deutsche Sammlung von Mikroorganismen und Zellkulturen, Inhoffenstraβe 7 B, D-38124 Braunschweig, Federal Republic of Germany.

The plasmid pAAV-CAG-hNaglu (SEQ ID NO: 5) was deposited on Mar. 13, 2014, under access number DSM 28568 at the DSMZ—Deutsche Sammlung von Mikroorganismen und Zellkulturen, Inhoffenstraβe 7 B, D-38124 Braunschweig, Federal Republic of Germany.

The plasmid pAAV-CAG-cohNaglu-version2 (SEQ ID NO: 20) was deposited on Apr. 29, 2015, under access number DSM 32042 at the DSMZ—Deutsche Sammlung von Mikroorganismen und Zellkulturen, Inhoffenstraβe 7 B, D-38124 Braunschweig, Federal Republic of Germany.

The plasmid pAAV-CAG-cohNaglu-version3 (SEQ ID NO: 23) was deposited on Apr. 29, 2015, under access number DSM 32043 at the DSMZ—Deutsche Sammlung von Mikroorganismen und Zellkulturen, Inhoffenstraβe 7 B, D-38124 Braunschweig, Federal Republic of Germany.

Definitions

The term "nucleotide sequence" refers to a nucleic acid molecule, either DNA or RNA, containing deoxyribonucleotides or ribonucleotides respectively. The nucleic acid may be double stranded, single stranded, or contain portions of both double stranded or single stranded sequence.

The term "% sequence identity" refers to the percentage of nucleotides of a candidate sequence that are identical to the nucleotides in the sequence of reference, after aligning the sequences to achieve the maximum % sequence identity. The % sequence identity can be determined by any methods or algorithms established in the art, such as the ALIGN, BLAST and BLAST 2.0 algorithms. See Altschul S, et al., Nuc Acids Res. 1977; 25:3389-3402 and Altschul S, et al., J Mol Biol. 1990; 215:403-410.

Herein, the % sequence identity is calculated dividing the number of nucleotides that are identical after aligning the sequence of reference and the candidate sequence, by the total number of nucleotides in the sequence of reference and multiplying the result by 100.

The terms "codify" or "coding" refer to the genetic code that determines how a nucleotide sequence is translated into a polypeptide or a protein. The order of the nucleotides in a sequence determines the order of amino acids along a polypeptide or a protein.

The term "protein" refers to a macromolecule composed of one or more linear chains of amino acids or polypeptides. Proteins can suffer post-translational modifications, like the conversion of a cysteine residue to 3-oxoalanine, glycosylation or metal binding. Glycosilation of a protein is the addition of different carbohydrates that are linked covalently to the amino acid chain.

The term "effective amount" refers to an amount of a substance sufficient to achieve the intended purpose. For example, an effective amount of an AAV9 vector to increase N-acetylglucosaminidase, alpha (Naglu) activity is an amount sufficient to reduce glycosaminoglycan accumulation. A "therapeutically effective amount" of an expression vector to treat a disease or disorder is an amount of the expression vector sufficient to reduce or eradicate the signs and symptoms of the disease or disorder. The effective amount of a given substance will vary with factors such as the nature of the substance, the route of administration, the size and species of the animal to receive the substance and the purpose of giving the substance. The effective amount in each individual case may be determined empirically by a skilled artisan according to established methods in the art.

The term "individual" refers to a mammal, preferably human or non-human mammal, more preferably mouse, rat, other rodents, rabbit, dog, cat, pig, cow, horse or primate, further more preferably human.

The term "operably linked" refers to the functional relation and the location of the promoter sequence with respect to the gene of interest (e.g. a promoter or enhancer is operably linked to a coding sequence if it affects the transcription of the sequence). Generally, a promoter operably linked is contiguous to the sequence of interest. However, an enhancer does not have to be contiguous to the sequence of interest to control its expression.

The term "tropism" refers to the way in which different viruses have evolved to preferentially target specific host species, or specific cell types within those species.

The term "gene therapy" refers to the transfer of genetic material (e.g. DNA or RNA) of interest into a host to treat or prevent a genetic or acquired disease or condition. The genetic material of interest encodes a product (e.g. a protein polypeptide, peptide or functional RNA) whose production in vivo is desired. For example, the genetic material of interest can encode an enzyme, hormone, receptor, or polypeptide of therapeutic value.

The terms "recombinant viral vector", "viral vector", "recombinant vector" or "vector" refer to an agent obtained from a naturally-occurring virus through genetic engineering techniques capable of transferring genetic material (e.g. DNA or RNA) of interest to a cell, which results in production of the product encoded by that said genetic material (e.g. a protein polypeptide, peptide or functional RNA) in the target cell. In the context of the present invention, a "recombinant vector" or a "vector" is to be understood as being a capsid protein as well as the genetic material contained within used to transfer said genetic material into a cell. By referring to a "recombinant vector" or to a "vector" through a nucleotide sequence, it means that it refers to a "recombinant vector" or a "vector" whose genome is as set forth in the corresponding sequence listing (SEQ ID).

The term "recombinant plasmid" or "plasmid" refers to a small, circular, double-stranded, self-replicating DNA molecule obtained through genetic engineering techniques capable of transferring genetic material of interest to a cell, which results in production of the product encoded by that said genetic material (e.g. a protein polypeptide, peptide or functional RNA) in the target cell. Furthermore, the term "recombinant plasmid" or "plasmid" also refers to a small, circular, double-stranded, self-replicating DNA molecule obtained through genetic engineering techniques used during the manufacturing of viral vectors as carriers of the recombinant vector genome.

DETAILED DESCRIPTION OF THE INVENTION

The present invention provides new recombinant vectors for the treatment of diseases, in particular for the treatment of mucopolysaccharidoses type III (MPSIII), especially MPSIIIB Apart from the genetic material, the recombinant vector may also contain different functional elements that include control elements for transcription like promoters or operators, transcription factors binding regions or enhancers and control elements for the initiation or termination of translation.

The vectors according to the invention are adenoassociated vectors (AAV) that are used to transfer the gene of interest. They have proved to have a high efficiency in transducing post-mitotic cells in wide range of tissue. In the context of the present invention, the vectors are used to deliver the human N-acetylglucosaminidase, alpha (hNaglu) polynucleotide (SEQ ID NO: 2) or a codon optimized human N-acetylglucosaminidase, alpha (cohNaglu) polynucleotide (SEQ ID NO: 3). An adenoassociated vector is a vector derived from the genome of an adenoassociated virus of the family of parvoviridae. The adenoassociated virus genome is built of single-stranded deoxyribonucleic acid (ssDNA). These vectors infect mammals but are non-pathogenic (i.e. do not cause disease). They can infect dividing or non-dividing cells, and their tropism changes depending on the serotype. The serotype is the classification of the viruses groups, depending on their capsid antigens. The serotype of adenoassciated virus, determined by its capsid protein, defines the virus tropism and allows its entry into a specific cell type. In the context of the present invention, the serotype 9 of the adenoassociated virus vectors (AAV9) shows the best ability to deliver the genetic material to the brain as well as to peripheral organs upon a single administration.

The inventors have surprisingly found that the association, in the same entity, of the AAV9 capsid with a nucleotide sequence coding for the N-acetylglucosaminidase, alpha, together with a specific CAG promoter allows a long-lasting expression of the missing enzyme in all areas of the brain.

As a consequence the lysosomal accumulation of glycosaminoglycan (GAG) is corrected, preventing by that way the neurological alterations characteristic of the MSPIII diseases, and in particular of the MPSIIIB This effect has been obtained even in the olfactory bulb, which is distant form the point of administration of the vectors. Further the AAV9 vectors according to the invention delivered into the cerebrospinal fluid were able to reach the systemic circulation to transduce the liver. The production and secretion of the enzyme by liver cells resulted in an increase of N-acetylglucosaminidase, alpha activity in serum, ultimately leading to the reduction of lysosomal pathology in many somatic tissues. This represents a clear advantage of the vectors according to the invention over the existing approaches that only partially corrected the clinical signs of the disease and usually exert their effect either in the brain or in the systemic circulation, but not in both.

Accordingly the present invention relates to recombinant AAV9 vectors containing a CAG promoter (SEQ ID NO: 4) linked to a nucleotide sequence coding for N-acetylglucosaminidase, alpha SEQ ID NO: 1.

In particular, the recombinant AAV9 vectors of the present invention contain a CAG promoter (SEQ ID NO: 4) linked to a nucleotide sequence coding for N-acetylglucosaminidase, alpha SEQ ID NO: 1 that has at least 80% sequence identity to SEQ ID NO: 2. More preferably, the AAV9 recombinant vectors of the present invention contain a CAG promoter (SEQ ID NO: 4) linked to a nucleotide sequence coding for N-acetylglucosaminidase, alpha SEQ ID NO: 1 that has at least 84% sequence identity to SEQ ID NO: 2. In particular the nucleotide sequence coding for N-acetylglucosaminidase, alpha SEQ ID NO: 1 has a 84%, 87%, 90%, 95%, 98%, or 99% sequence identity to SEQ ID NO: 2.

In another particular embodiment the recombinant AAV9 vectors of the present invention contains a CAG promoter (SEQ ID NO: 4) linked to a nucleotide sequence coding for N-acetylglucosaminidase, alpha SEQ ID NO: 1 that has at least 85% sequence identity to SEQ ID NO: 3. In particular the nucleotide sequence coding for N-acetylglucosaminidase, alpha SEQ ID NO: 1 has a 85%, 87%, 90%, 95%, 98%, or 99% sequence identity to SEQ ID NO: 3.

In a preferred embodiment of the invention, the nucleotide sequence coding for N-acetylglucosaminidase, alpha SEQ ID NO: 1 is SEQ ID NO: 2.

In a further preferred embodiment of the invention, the nucleotide sequence coding for N-acetylglucosaminidase, alpha SEQ ID NO: 1 is SEQ ID NO: 3. The sequence as set forth in SEQ ID NO: 3 presents 84% sequence identity with SEQ ID NO: 2.

In a still further preferred embodiment of the invention, the nucleotide sequence coding for N-acetylglucosaminidase, alpha SEQ ID NO: 1 is SEQ ID NO: 19.

In a still further preferred embodiment of the invention, the nucleotide sequence coding for N-acetylglucosaminidase, alpha SEQ ID NO: 1 is SEQ ID NO: 22.

The AAV9 vectors according to the present invention contain a promoter that control the translation and transcription of the gene of interest. A promoter is a nucleotide sequence operably linked to said gene of interest. The promoter used in the present invention is the CAG promoter which refers to the combination comprising the cytomegalovirus early enhancer element and the chicken β-actin promoter. It further includes a portion of β-globin intron that confers stability to the m RNA derived from the gene of interest, See Alexopoulou A, et al., BMC Cell Biology 2008; 9(2): 1-11. The CAG promoter included in the AAV9 vectors of the present invention has a sequence SEQ ID NO: 4. In particular this CAG promoter proved to be more efficient than the CMV promoter usually used in the art.

In a further preferred embodiment of the invention, the recombinant AAV9 vector is chosen from AAV9-CAG-hNaglu (SEQ ID NO: 9), AAV9-CAG-cohNaglu (SEQ ID NO: 10) and AAV9-CAG-cohNaglu-version2 (SEQ ID NO: 21) and AAV9-CAG-cohNaglu-version3 (SEQ ID NO: 24). Preferably, the recombinant AAV9 vector is chosen from AAV9-CAG-hNaglu (SEQ ID NO: 9), AAV9-CAG-cohNaglu (SEQ ID NO: 10). More specifically, the recombinant AAV9 vectors of the present invention are composed of the viral capsid of the serotype 9 of human adenoassociated virus and a modified genome containing the Inverted Terminal Repeats (ITRs) of human adenoassociated virus serotype 2, the CAG promoter, the Coding Sequence (CDS) of the human alpha N-acetylglucosamidinase (Naglu) gene and the polyA from the rabbit beta-globin gene.

The present invention also related to plasmids that contain the nucleotide sequence coding for N-acetylglucosaminidase, alpha SEQ ID NO: 1. In particular the plasmids according to the present invention contain a nucleotide sequence coding for N-acetylglucosaminidase, alpha SEQ ID NO: 1 that has at least 80% sequence identity to SEQ ID NO: 2. Preferably, the plasmids according to the present invention contain a nucleotide sequence coding for N-acetylglucosaminidase, alpha SEQ ID NO: 1 that has at least 84% sequence identity to SEQ ID NO: 2. In particular the nucleotide sequence coding for N-acetylglucosaminidase, alpha SEQ ID NO: 1 has a 84%, 87%, 90%, 95%, 98%, or 99% sequence identity to SEQ ID NO: 2.

In a preferred embodiment, the plasmids according to the present invention contain a nucleotide sequence coding for N-acetylglucosaminidase, alpha SEQ ID NO: 1 that has at least 85% sequence identity to SEQ ID NO: 3. In particular the nucleotide sequence coding for N-acetylglucosaminidase, alpha SEQ ID NO: 1 has a 85%, 87%, 90%, 95%, 98%, or 99% sequence identity to SEQ ID NO: 3.

These plasmids are useful to produce the recombinant AAV9 vectors of the present invention by transfection of HEK293 cells using methods known in the state of the art.

In a preferred embodiment of the invention, the nucleotide sequence contained in the plasmids of the invention and coding for N-acetylglucosaminidase, alpha SEQ ID NO: 1 is SEQ ID NO: 2.

In another preferred embodiment of the invention, the nucleotide sequence contained in the plasmids of the invention and coding for N-acetylglucosaminidase, alpha SEQ ID NO: 1 is SEQ ID NO: 3.

In another preferred embodiment of the invention, the nucleotide sequence contained in the plasmids of the invention and coding for N-acetylglucosaminidase, alpha SEQ ID NO: 1 is SEQ ID NO: 19.

In another preferred embodiment of the invention, the nucleotide sequence contained in the plasmids of the invention and coding for N-acetylglucosaminidase, alpha SEQ ID NO: 1 is SEQ ID NO: 22.

In a more preferred embodiment, the plasmids of the invention are chosen from pAAV-CAG-hNaglu (SEQ ID NO: 5), pAAV-CAG-cohNaglu (SEQ ID NO: 6), pAAV-CAG-cohNaglu-version2 (SEQ ID NO: 20) and pAAV-CAG-cohNaglu-version3 (SEQ ID NO: 23), and especially chosen from pAAV-CAG-hNaglu (SEQ ID NO: 5) and pAAV-CAG-cohNaglu (SEQ ID NO: 6), and preferably the plasmid is pAAV-CAG-cohNaglu (SEQ ID NO: 6).

The present invention further provides a method for the production of the adenoassociated viral recombinant vectors AAV9 according to the invention. The process comprises the steps of:

i) providing a first vector comprising the sequence coding for the protein of interest interposed between a first AAV terminal repeat and a second AAV terminal repeat, a CAG promoter operably linked to the sequence coding for the protein of interest; a second vector comprising an AAV rep gene and a AAV cap gene from serotype 9; and a third vector comprising the adenovirus helper function gene;

ii) co-transfecting competent cells with the vectors of step i);

iii) culturing the transfected cells of step ii); and iv) purifying the expression vectors from the culture of step iii).

In a preferred embodiment, the AAV first and second terminal repeats of the first vector are ITRs from the AAV serotype 2. In another preferred embodiment, the AAV rep genes of the second vector are from the AAV serotype 2. In another preferred embodiment, the competent cells are HEK293 cells.

The invention also provides a method for the preparation of the plasmids according to the invention, comprising the step of:

i) excising the sequence coding for the protein of interest from the starting plasmid, by digestion, in particular using MIuI/EcoRI, ii) cloning the sequence coding for the protein of interest between two restriction sites of the AAV backbone plasmid pAAV-CAG, hereby obtaining the corresponding plasmid including the sequence coding for the protein of interest.

The present invention contemplates, in an additional aspect, pharmaceutical compositions containing a therapeutically effective amount of the AAV9 vectors described therein, or a therapeutically effective amount of the plasmids described therein.

Pharmaceutical compositions of the invention comprise the recombinant AAV9 vectors in a pharmaceutically acceptable carrier. The composition may also comprise at least one auxiliary substance. The auxiliary substances can be selected among carriers, excipients, solvents, diluents, or adjuvants. Acceptable carriers, diluent or adjuvants are non-toxic and are preferably inert at the dosage and concentrations employed and include buffers such as phosphate, citrate or other organic acids; antioxidants; low molecular weight polypeptides, proteins such as serum albumin, gelatin or immunoglobulins; hydriophilic polymers; aminoacids; monosaccharides, disaccharides and other carbohydrates including glucose, mannose or dextrins; chelating agents; sugar alcohols such as mannitol or sorbitol, salt forming couterions such as sodium; and/or non-ionic surfactants such as polyethylene-polyoxypropylene block copolymer (Pluronic F68®) polyethylene glycol (PEG).

In a preferred embodiment, the pharmaceutical compositions according to the invention are suitable for parenteral administration. Examples of parenteral administration are intravenous, subcutaneous, intracisternal and intramuscular injections. Preferably, the pharmaceutical composition according to the invention is suitable for intravenous or intracisternal administration. Compositions suitable for such parenteral administration include sterile aqueous solutions or dispersions, sterile powders for extemporaneous preparation of sterile solutions or dispersions. Advantageously the pharmaceutical compositions according to the invention are preserved from contaminating action of bacteria and fungi.

The daily dosage for humans and animals may vary depending on factors that have their basis in the respective species or other factors, such as age, sex, weight or degree of illness and so forth.

Another aspect of the present invention relates to the therapeutical use of the AAV9 vectors described hereinbefore, or the plasmids described hereinbefore. As mentioned above the recombinant AAV9 vectors according to the invention achieve an expression of the missing Naglu enzyme, thus correcting the lysosomal accumulation of GAGs. This allows correcting all clinical signs of the mucopolysaccharidoses type III (MPSIII) and especially MPSIIIB In this respect the present invention also concern the recombinant AAV9 vectors described hereinbefore, or the plasmids described hereinbefore for use as a medicament.

In particular, the invention relates to the recombinant AAV9 vectors described hereinbefore, or the plasmids described hereinbefore for increasing the alpha N-glucosaminidase activity in the body.

In a further preferred aspect, the present invention relates to the recombinant AAV9 vectors described hereinbefore, or the plasmids described hereinbefore for treatment of mucopolysaccharidoses type III (MPSIII) and especially MPSIIIB In a still further embodiment, the present invention relates to the use of the recombinant AAV9 vectors described hereinbefore, or the plasmids described hereinbefore for the manufacture of a medicament useful for the treatment of mucopolysaccharidoses type III (MPSIII) and especially MPSIIIB Another embodiment of the present invention is directed to the method of treatment of mucopolysaccharidoses type III (MPSIII) and especially MPSIIIB, comprising the step of administering at least a recombinant AAV9 vector described hereinbefore, or at least a plasmid described hereinbefore to a subject in need thereof.

The present invention further provides an isolated cell comprising the nucleotide sequence coding for N-acetylglucosaminidase, alpha SEQ ID NO: 1. In particular the cell according to the invention comprises a nucleotide sequence coding for N-acetylglucosaminidase, alpha SEQ ID NO: 1 that has at least 80% sequence identity to SEQ ID NO: 2. Preferably, the nucleotide sequence coding for N-acetylglucosaminidase, alpha SEQ ID NO: 1 that has at least 84% sequence identity to SEQ ID NO: 2. In particular the nucleotide sequence coding for N-acetylglucosaminidase, alpha SEQ ID NO: 1 has a 84%, 87%, 90%, 95%, 98%, or 99% sequence identity to SEQ ID NO: 2. In a further particular aspect, the nucleotide sequence coding for N-acetylglucosaminidase, alpha SEQ ID NO: 1 has at least 85% sequence identity to SEQ ID NO: 3, and preferably 85%, 87%, 90%, 95%, 98%, or 99% sequence identity to SEQ ID NO: 3.

In a preferred embodiment the cells of the invention comprise the nucleotide sequence SEQ ID NO: 2 coding for N-acetylglucosaminidase, alpha SEQ ID NO: 1.

In another preferred embodiment the cells of the invention comprise the nucleotide sequence SEQ ID NO: 3 coding for N-acetylglucosaminidase, alpha SEQ ID NO: 1.

In another preferred embodiment the cells of the invention comprise the nucleotide sequence SEQ ID NO: 19 coding for N-acetylglucosaminidase, alpha SEQ ID NO: 1.

In another preferred embodiment the cells of the invention comprise the nucleotide sequence SEQ ID NO: 22 coding for N-acetylglucosaminidase, alpha SEQ ID NO: 1.

The following examples are merely illustrative of certain embodiments of the invention and cannot be considered as restricting it in any way.

General Procedures

1. Recombinant AAV Vectors

The AAV vectors described herein were obtained by triple transfection. The materials required for making the vectors were: HEK293 cells (expressing E1 genes), helper plasmid providing adenovirus function, plasmid providing AAV rep genes from serotype 2 and cap genes from the serotype 9 (AAV9) and, finally, the backbone plasmid with AAV2 ITRs and the construct of interest.

To generate N-acetylglucosaminidase, alpha-expressing AAV vectors, the non-optimized or optimized CDS of human, murine or canine N-acetylglucosaminidase, alpha were cloned into an AAV backbone plasmid under the control of the ubiquitous hybrid CAG promoter.

Vectors were generated by helper virus-free transfection of HEK293 cells using three plasmids with modifications. See Matsushita T, et al., Gene Ther. 1998; 5:938-945 and Wright J, et al., Mol. Ther. 2005; 12:171-178. Cells were cultured to 70% confluence in roller bottles (RB) (Corning, Corning, N.Y., US) in DMEM supplemented with 10% FBS and then co-transfected with: 1) a plasmid carrying the expression cassette flanked by the viral ITRs of serotype 2 AAV (described above); 2) a plasmid carrying the AAV rep2 and the cap9 genes; and 3) a plasmid carrying the adenovirus helper functions. Vectors were purified by two consecutives cesium chloride gradients using an optimized protocol as previously described. See Ayuso E, et al., Gene Ther. 2010; 17:503-510. Vectors were dialyzed against PBS, filtered, titred by qPCR and stored at −80° C. until use.

The vectors of the present invention were constructed according to molecular biology techniques well known in the art.

2. Animals

A congenic mutant C57Bl/6J N-acetylglucosaminidase, alpha-deficient mouse (MPSIIIB) model was purchased from The Jackson Laboratory (Bar Harbor, Me., USA. Stock 003827). See Li et al., Proc Natl Acad Sci. 1999; 96(25): 14505-10. Affected MPSIIIB and healthy control mice were inbred from heterozygous founders. Genotype was determined on genomic DNA from tail-clipped samples with a PCR analysis that amplifies a sequence encompassing the targeted mutation. The sequences of the respective sense and antisense primers were: Forward Primer: 5'-GTC GTC TCC TGG TTC TGG AC-3' (SEQ ID NO: 13), Reverse Primer: 5'-ACC ACT TCA TTC TGG CCA AT-3' (SEQ ID NO: 14), Reverse Primer Mutation: 5'-CGC TTT CTG GGC TCA GAG-3' (SEQ ID NO: 15). Mice were fed ad libitum with a standard diet (Harlan, Tekland)) and maintained under a light-dark cycle of 12 h (lights on at 9:00 A.M.).

3. Hydrodynamic Delivery of hNAGLU-Encoding Plasmids to Mice

For hydrodynamic delivery of pAAV-CAG-hNaglu, pAAV-CAG-cohNaglu-version2 and pAAV-CAG-cohNaglu-version3 plasmids, 2-month-old MPSIIIB and wild-type animals received through tail vein injection in <5 seconds a total dose of 50 μg of plasmid in a volume equal to 10% of the body weight of the animal. This technique results in expression of plasmid-encoded transgenes mainly in the liver. See Liu et al., Gene Ther. 1990; 6(7):1258-66. As control, a cohort of mice received and equal volume of saline solution. Mice were sacrificed either at 1 week after hydrodynamic injection of the plasmids. Organs were harvested as described in the following section.

4. Vector Administration and Sample Collection

For intracisternal delivery of AAV9-CAG-comNaglu vectors to mice, a total dose of $3\times10^{10}$ vg were injected to the cisterna magna of 2-month-old MPSIIIB animals. A similar cohort of animals was injected with $3.9\times10^{10}$ vg control non-coding (AAV9-null) vector. At 5 months of age, i.e. 3 months post vector administration, mice were anesthetized and then transcardially perfused with 10 ml of PBS to completely clear blood from tissues. The entire brain and multiple somatic tissues (including liver, spleen, pancreas, kidney, lung, heart, skeletal muscle and testicles) were collected and either frozen in liquid nitrogen and stored at −80° C. or immersed in formalin for subsequent histological analyses.

For intravenous delivery of AAV9-CAG-hNaglu and AAV9-CAG-cohNaglu vectors, 2-month-old MPSIIIB animals received a total dose of $5\times10^{11}$ vg through tail vein injection. At 4 months of age, i.e. 2 months post vector administration, mice were sacrificed and organs were harvested as described in the previous paragraph.

For intracisternal delivery of AAV9-CAG-hNaglu and AAV9-CAG-cohNaglu vectors, a total dose of $9.3\times10^{9}$ vg were injected in the cisterna magna of 2-month-old MPSIIIB animals. At 4 months of age, i.e. 2 months post vector administration, mice were sacrificed and organs were harvested as described in the previous paragraph.

For intracisternal delivery of AAV9-CAG-cocNaglu vectors to dogs, a total dose of $6.5\times10^{12}$ vg was administered to healthy adult Beagle dogs via cisterna magna injection. Two of the animals received an intravenous injection of $1\times10^{11}$ vg/kg of AAV9-null vectors 6 weeks prior to administration of Naglu vectors to pre-immunize them against AAV9. First weekly, and then monthly, CSF and serum samples were collected and stored at −80° C.

5. Quantification of Vector Genome Copy Number

Tissues (≈100 mg) were digested overnight (ON) at 56° C. in 400 μl of Proteinase K solution (0.2 mg/ml). Total DNA was isolated from supernatants by extraction using standard techniques. DNA was resuspended in distilled water and quantified using a NanoDrop ND-1000 (NanoDrop, Wilmington, Del., USA). Vector genome copy number in 20 ng of total DNA was determined by quantitative real time PCR with primers and probe specifics for the murine N-acetylgluosaminidase, alpha transgene that do not amplify the endogenous genomic locus. Forward primer: 5'-GCC GAG GCC CAG TTC TAC-3' (SEQ ID NO: 16); Reverse primer: 5'-TTG GCG TAG TCC AGG ATG TTG-3' (SEQ ID NO: 17); Probe: 5'-AGC AGA ACA GCA GAT ACC AGA TCA CCC-3' (SEQ ID NO: 18). The final values were determined by comparing to a reference standard curve, built from serial dilutions of the linearized plasmid used for AAV vector production spiked into 20 ng non-transduced genomic DNA.

6. N-Acetylglucosaminidase, Alpha Activity and Glycosaminoglycan Quantification

Liver and brain samples were sonicated in Mili-Q water. Serum was analysed unprocessed. N-acetylglucosaminidase, alpha activity was determined with a 4-methylumbelliferone-derived fluorogenic substrate (Moscerdam Substrates, Oegstgeest, NL), as described previously. See Marsh and Fensom, Clin Genet. 1985; 27(3):258-262. Brain and liver activity levels were normalized against the total amount of protein, quantified using Bradford protein assay (Bio-Rad, Hercules, Calif., US). Serum activity was normalized against volume.

For glycosaminoglycan (GAG) quantification, tissue samples were weighted and then digested with proteinase K and extracts were clarified by centrifugation and filtration. GAG levels were determined in tissue extracts with the Blyscan sulfated glycosaminoglycan kit (Biocolor, Carrickfergus, County Antrim, GB), using chondroitin 4-sulfate as standard. The levels of GAG were normalized to wet tissue weight.

7. Activity of Other Lysosomal Enzymes

IDUA activity was measured in 15 μg of protein incubated for 1 h at 37° C. with 4-methylumbelliferyl α-N-iduronide (Glycosynth). For IDS activity, 15 μg of protein were first incubated with 4-methylumbelliferyl-α-L-iduronide-2-sulphate (Moscerdam Substrates) for 4 h at 37° C., followed by a second 24 h incubation at 37° C. with a pool of lysosomal enzymes from bovine testis (LEBT-M2, Moscerdam Substrates). SGSH activity was measured as previously described. See Haurigot et al., J Clin Invest 2013; 123(8): 3254-71. For GUSB activity, 10 μg of protein were incubated with 4-methylumbelliferyl-β-D-glucuronide (Sigma) at 37° C. for 1 h. HEXB activity was assayed by incubation of 0.1 μg of protein with 4-methylumbelliferyl N-acetyl-β-D-glucoaminide (Sigma) for 1 h at 37° C. After stopping reactions by increasing the pH, released fluorescence was measured with FLx800 fluorimeter (BioTek Instruments). All enzyme activities were normalized against total protein content quantified by Bradford (Bio-Rad).

8. Histological Analyses

Tissues were fixed for 12-24 h in formalin, embedded in paraffin and sectioned. For immunohistochemical detection of LAMP1 in somatic tissues, paraffin sections were subjected to heat-induced epitope retrieval in citrate buffer, pH 6, and then incubated overnight at 4° C. with rat anti-LAMP1 antibody (1D4B; Santa Cruz Biotechnology, Santa Cruz, Calif., US) diluted at 1:100 and subsequently incubated with biotinylated rabbit anti-rat antibody (Dako, Glostrup, DK) at 1:300. For immunohistochemical detection of LIMP2 in the brain, paraffin sections were incubated overnight at 4° C. with rabbit anti-LIMP2 antibody (NB400; Novus Biologicals, Littleton, Colo., USA) diluted at 1:100 and subsequently incubated with biotinylated goat anti-rabbit antibody (31820; Vector Laboratories, Burlingame, Calif., USA) at 1:300. For GFAP immunostaining in brain samples, paraffin sections were incubated overnight at 4° C. with rabbit anti-GFAP antibody (Ab6673; Abcam, Cambridge, UK) diluted at 1:1000 and subsequently incubated with biotinylated goat anti-rabbit antibody (31820; Vector Laboratories, Burlingame, Calif., USA) at 1:300. LAMP1, LIMP2 and GFAP signals were amplified by incubating sections with ABC-Peroxidase staining kit (Thermo Scientific, Waltham, Mass., US) at 1:100 dilution and visualized using 3,3-diaminobenzidine (Sigma-Aldrich, St. Louis, Mo., US) as a chromogen. Brightfield images were obtained with an optical microscope (Eclipse 90i; Nikon, Tokyo, JP).

To stain microglial cells in brain samples, paraffin sections were incubated overnight at 4° C. with Bsi-B4 lectin (L5391; Sigma-Aldrich, St. Louis, Mo., USA) diluted at 1:100. Bsi-B4 signal was visualized using 3,3-diaminobenzidine (Sigma-Aldrich, St. Louis, Mo., US) as a chromogen. Brightfield images were obtained with an optical microscope (Eclipse 90i; Nikon, Tokyo, JP).

The NIS Elements Advanced Research 2.20 software was used to quantify LIMP2, GFAP, and Bsi-B4 signals in 3-5 images of each brain region (original magnification, ×20) per animal, using the same signal threshold settings for all animals. Then, the percentage of positive area was calculated, i.e., the area, in pixels, with a positive signal over the total tissue area in the image.

9. Transmission Electron Microscopic Analysis

Mice were sacrificed by an overdose of isofluorane (Isofluo, Labs. Esteve, Barcelona, ES) and perfused via inferior vena cava with 1 ml of 2.5% glutaraldehyde and 2% paraformaldehyde. A small portion (approximately 1 $mm^3$) of the lateral lobe of the liver and of the cerebral cortex were sectioned and incubated for 2 hours at 4° C. in the same fixative. After washing in cold cacodylate buffer, the specimens were postfixed in 1% osmium tetroxide, stained in aqueous uranyl acetate, and then dehydrated through a graded ethanol series and embedded in epoxy resin. Ultrathin sections (600-800 Å) from the resin blocks were stained using lead citrate and examined in a transmission electron microscope (H-7000; Hitachi, Tokyo, JP).

10. Transcriptomic Analysis

Half mouse brain (~250 mg) was mechanically homogenized and total RNA was isolated with mirVana™ (Ambion, Life Technolo-gies). cDNA was synthesized and subsequently hybridized in the GeneChip Mouse Gene 2.1 ST 16 array plate (Affymetrix) by Progenika Biopharma (Spain); sample processing, hybridization and scanning were carried out following Affymetrix recommended protocols and equipment. Data normalization was done by RMA (Robust™ Multiarray averaging) method using Affymetrix® Expression Console tool, obtaining log 2 transformed normalized values. Data were filtered to focus the analysis on known coding sequences, obtaining an initial list of 26688 altered genes, which were subsequently refiltered to remove genes with variance below the 75th percentile. This process generated a working list of 6672 genes. For differentially expressed genes, FDR (False Discovery Rate) criteria <0.1 with 80% confidence was established. For clustering analysis, data were standardized and represented as heatmap using the J-Express Pro software (jexpress.bioinfo.no). Functional analysis was performed using Genecodis Tool 2.0 (genecodis2.dacya.ucm.es). Array data have been submitted to ArrayExpress database (http://www.ebi.ac.uk/arrayexpress/; accession code: E-MTAB-2984).

11. Behavioural Assessment

Behavioural changes were assessed through the Open-field test. Animals were placed in the lower left corner of a brightly lit chamber (41×41×30 cm). The surface of the arena was divided in three concentric squares: centre (14×14 cm), periphery (27×27 cm) and border (41×41 cm). Exploratory behaviour and general activity were recorded during the first two minutes using a video-tracking system (Smart Junior, Panlab). The test was always performed at the same time of day (9:00 am to 1:00 pm) to minimize influence of circadian cycles.

12. Statistical Analysis

All results are expressed as mean±SEM. Statistical comparisons were made using one-way ANOVA, and multiple comparisons between control and treatment groups will be made using Dunnett's post test. Statistical significance was considered if P<0.05. The Kaplan-Meier method will be used to analyze survival, and the log-rank test for comparisons.

EXAMPLES

Example 1: Construction of pAAV-CAG-hNaglu

Figure 19:
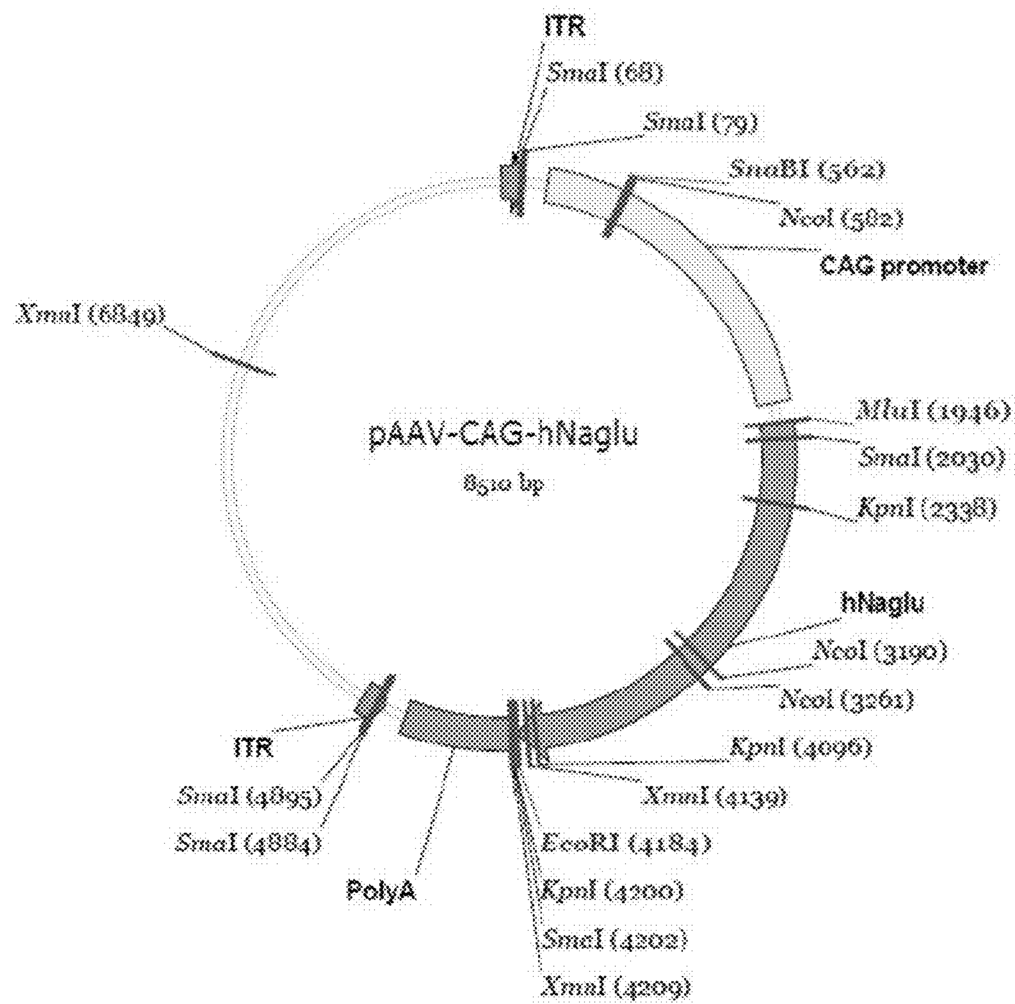
FIG. 19. Schematic representation of the plasmid pAAV-CAG-hNaglu (A) and schematic representation of the genome of the recombinant AAV vector AAV9-CAG-hNaglu (B).

The human N-acetylglucosaminidase, alpha coding sequence (CDS) was utilized as starting material (NCBI Reference Sequence: NM_000263) and chemically synthesized for this purpose (GeneArt; Life Technologies). The CDS was received cloned inside the plasmid pMA (AmpR) flanked by MluI and EcoRI restriction sites at 5' and 3' ends, respectively. N-acetylglucosaminidase, alpha CDS was excised by MluI/EcoRI digestion and then cloned between the MluI and EcoRI restrictions sites of the AAV backbone plasmid pAAV-CAG (AmpR). The resulting plasmid was named pAAV-CAG-hNaglu (accession number DSM 28568). See SEQ ID NO: 5, and FIG. 19 A.

The pAAV-CAG plasmid had been previously generated and contained the ITRs from the AAV2 genome, the CAG promoter, and the polyA signal from rabbit β-globin, as well as a multicloning site for cloning of CDSs of interest. The CAG promoter is a hybrid promoter composed of the CMV early/intermediate enhancer and the chicken β-actin promoter. This promoter is able to drive a potent expression ubiquitously. See Sawicki J et al., Exper Cell Res. 1998; 244:367-369, Huang J et al., J Gene Med. 2003; 5:900-908, Liu Y et al., Exp Mol Med. 2007; 39(2):170-175.

Example 2: Production of AAV9-CAG-hNaglu

Vectors AAV9-CAG-hNaglu (SEQ ID NO: 9 and FIG. 19 B)) were generated by helper virus-free transfection of HEK293 cells using three plasmids with modifications. See Matsushita, 1998, supra and Wright, 2005, supra. Cells were cultured to 70% confluence in roller bottles (RB) (Corning, Corning, N.Y., US) in DMEM supplemented with 10% FBS and then co-transfected with: 1) a plasmid carrying the expression cassette flanked by AAV2 ITRs (pAAV-CAG-hNaglu); 2) a plasmid carrying the AAV2 rep and the AAV9 cap genes (pREP2CAP9); and 3) a plasmid carrying the adenovirus helper functions. Vectors were purified by two consecutives cesium chloride gradients using either a standard protocol or an optimized protocol as previously described. See Ayuso, 2010, supra. Vectors were dialyzed against PBS, filtered, titred by qPCR and stored at −80° C. until use.

Example 3: Construction of pAAV-CAG-cohNaglu

Expression cassettes including an optimized version of the human N-acetylglucosaminidase, alpha CDS (cohNaglu) were designed and obtained. The sequence optimization (GeneArt®) was performed to maximize the efficiency of N-acetylglucosaminidase, alpha protein production in human beings through elimination of cryptic splice sites and RNA destabilizing sequence elements for increased RNA stability, addition of RNA stabilizing sequence elements, codon optimization and G/C content adaptation, avoidance of stable RNA secondary structures amongst others changes. The optimized CDS was received cloned in the plasmid pMA-RQ (AmpR) flanked by MluI and EcoRI restriction sites at 5' and 3', respectively.

Figure 20:
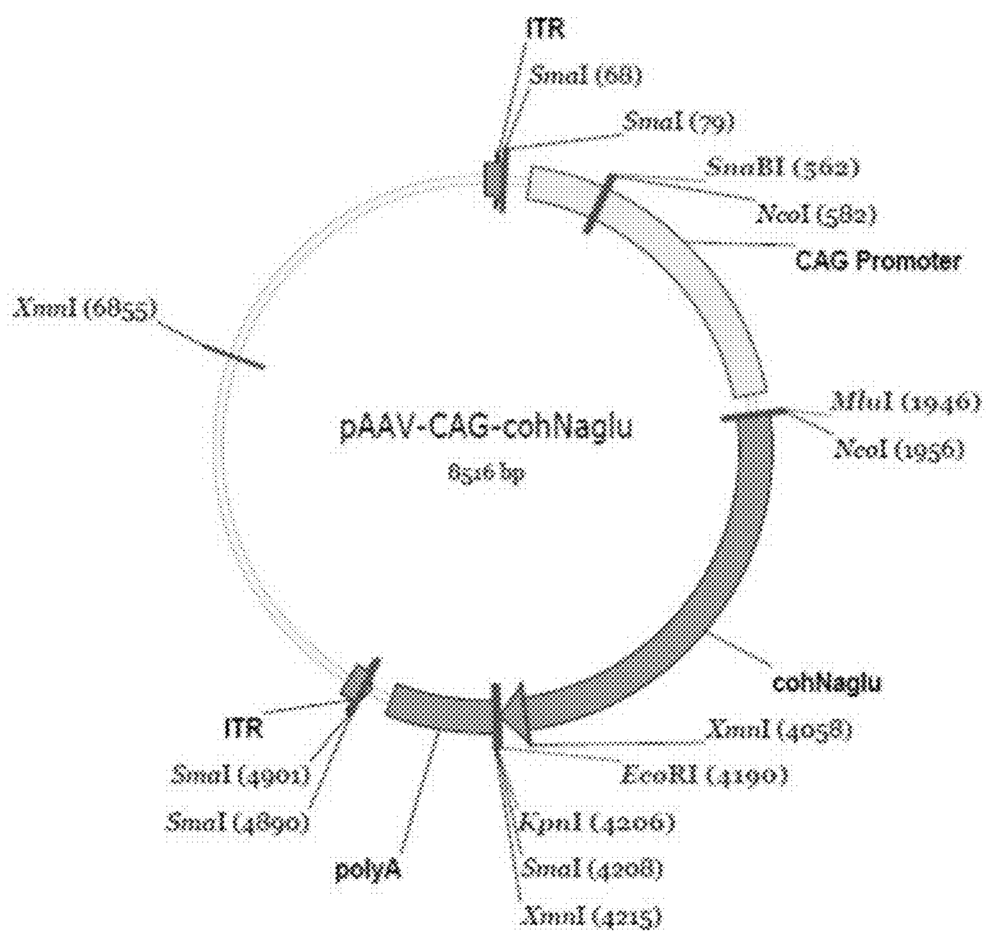
FIG. 20. Schematic representation of the plasmid pAAV-CAG-cohNaglu (A) and schematic representation of the genome of the recombinant AAV vector AAV9-CAG-cohNaglu (B).

The pMA-RQ-cohNaglu plasmid was digested with MluI and EcoRI to excise the optimized N-acetylglucosaminidase, alpha CDS. Subsequently, this fragment was cloned between the same restriction sites of the pAAV-CAG backbone plasmid to generate the pAAV-CAG-cohNaglu plasmid (accession number DSM 26626). See SEQ ID NO:6 and FIG. 20 A.

Example 4: Production of AAV9-CAG-cohNaglu

Vectors AAV9-CAG-cohNaglu (SEQ ID NO: 10 and FIG. 20 B) were generated by helper virus-free transfection of HEK293 cells using three plasmids with modifications. See Matsushita, 1998, supra and Wright, 2005, supra. Cells were cultured to 70% confluence in roller bottles (RB) (Corning, Corning, N.Y., US) in DMEM supplemented with 10% FBS and then co-transfected with: 1) a plasmid carrying the expression cassette flanked by AAV2 ITRs (pAAV-CAG-cohNaglu); 2) a plasmid carrying the AAV2 rep and the AAV9 cap genes (pREP2CAP9); and 3) a plasmid carrying the adenovirus helper functions. Vectors were purified by two consecutives cesium chloride gradients using either a standard protocol or an optimized protocol as previously described. See Ayuso, 2010, supra. Vectors were dialyzed against PBS, filtered, titred by qPCR and stored at −80° C. until use.

Example 5: Construction of pAAV-CAG-cohNaglu-Version2

Expression cassettes including a second optimized version of the human N-acetylglucosaminidase, alpha CDS (cohNaglu-version2) were designed and obtained. The optimized CDS (DNA 2.0®) was received cloned in the plasmid pJ208 (AmpR) flanked by MluI and EcoRI restriction sites at 5' and 3', respectively.

Figure 21:
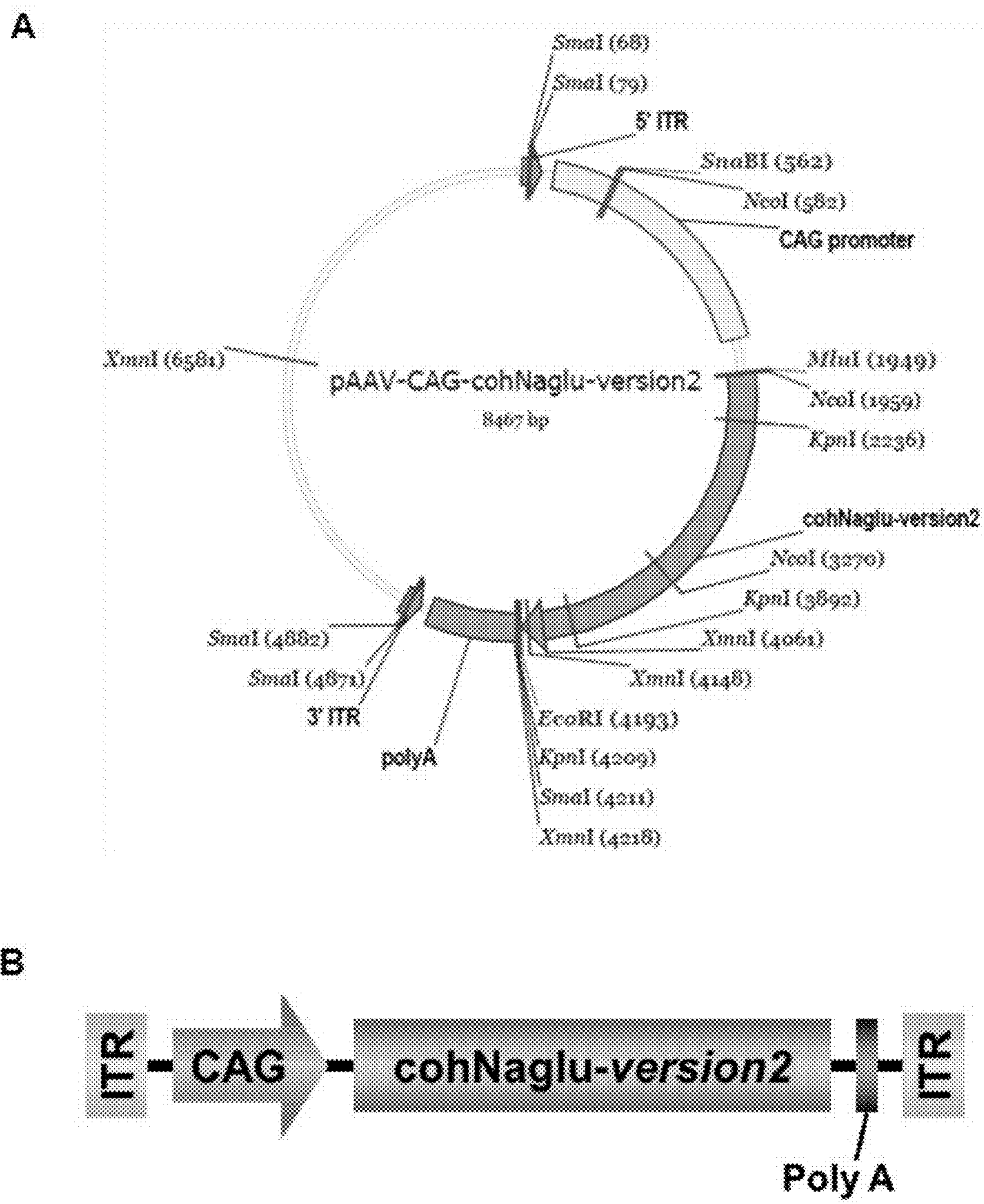
FIG. 21. Schematic representation of the plasmid pAAV-CAG-cohNaglu-version2 (A) and schematic representation of the genome of the recombinant AAV vector AAV9-CAG-cohNaglu-version2 (B).

The pJ208-cohNaglu-version2 plasmid was digested with MluI and EcoRI to excise the optimized N-acetylglucosaminidase, alpha-version2 CDS. Subsequently, this fragment was cloned between the same restriction sites of the pAAV-CAG backbone plasmid to generate the pAAV-CAG-cohNaglu-version2 plasmid (accession number DSM 32042). See SEQ ID NO:20 and FIG. 21 A.

Example 6: Production of AAV9-CAG-cohNaglu-version2

Vectors AAV9-CAG-cohNaglu-version2 (SEQ ID NO: 21 and FIG. 21 B) were generated by helper virus-free transfection of HEK293 cells using three plasmids with modifications. See Matsushita, 1998, supra and Wright, 2005, supra. Cells were cultured to 70% confluence in roller bottles (RB) (Corning, Corning, N.Y., US) in DMEM supplemented with 10% FBS and then co-transfected with: 1) a plasmid carrying the expression cassette flanked by AAV2 ITRs (pAAV-CAG-cohNaglu-version2); 2) a plasmid carrying the AAV2 rep and the AAV9 cap genes (pREP2CAP9); and 3) a plasmid carrying the adenovirus helper functions. Vectors were purified by two consecutives cesium chloride gradients using either a standard protocol or an optimized protocol as previously described. See Ayuso, 2010, supra. Vectors were dialyzed against PBS, filtered, titred by qPCR and stored at −80° C. until use.

Example 7: Construction of pAAV-CAG-cohNaglu-version3

Expression cassettes including a third optimized version of the human N-acetylglucosaminidase, alpha CDS (cohNaglu-version3) were designed and obtained. The optimized CDS (GenScript, Inc) was received cloned in the plasmid pUC57 (AmpR) flanked by MluI and EcoRI restriction sites at 5' and 3', respectively.

The pUC57-cohNaglu-version3 plasmid was digested with MluI and EcoRI to excise the optimized N-acetylglucosaminidase, alpha-version3 CDS. Subsequently, this fragment was cloned between the same restriction sites of the pAAV-CAG backbone plasmid to generate the pAAV-CAG-cohNaglu-version3 plasmid (accession number DSM 32043). See SEQ ID NO:23 and FIG. 22 A.

Example 8: Production of AAV9-CAG-cohNaglu-version3

Vectors AAV9-CAG-cohNaglu-version3 (SEQ ID NO: 24 and FIG. 22 B) were generated by helper virus-free transfection of HEK293 cells using three plasmids with modifications. See Matsushita, 1998, supra and Wright, 2005, supra. Cells were cultured to 70% confluence in roller bottles (RB) (Corning, Corning, N.Y., US) in DMEM supplemented with 10% FBS and then co-transfected with: 1) a plasmid carrying the expression cassette flanked by AAV2 ITRs (pAAV-CAG-cohNaglu-version3); 2) a plasmid carrying the AAV2 rep and the AAV9 cap genes (pREP2CAP9); and 3) a plasmid carrying the adenovirus helper functions. Vectors were purified by two consecutives cesium chloride gradients using either a standard protocol or an optimized protocol as previously described. See Ayuso, 2010, supra. Vectors were dialyzed against PBS, filtered, titred by qPCR and stored at −80° C. until use.

Example 9: Construction of pAAV-CAG-comNaglu

The CDS for murine N-acetylglucosaminidase, alpha (NCBI Reference Sequence: NM_013792) was subjected to sequence optimization (GeneArt; Life Technologies). The optimized CDS was received cloned inside the plasmid pMA-RQ (AmpR) flanked by MluI and EcoRI restriction sites at 5' and 3', respectively.

Figure 23:
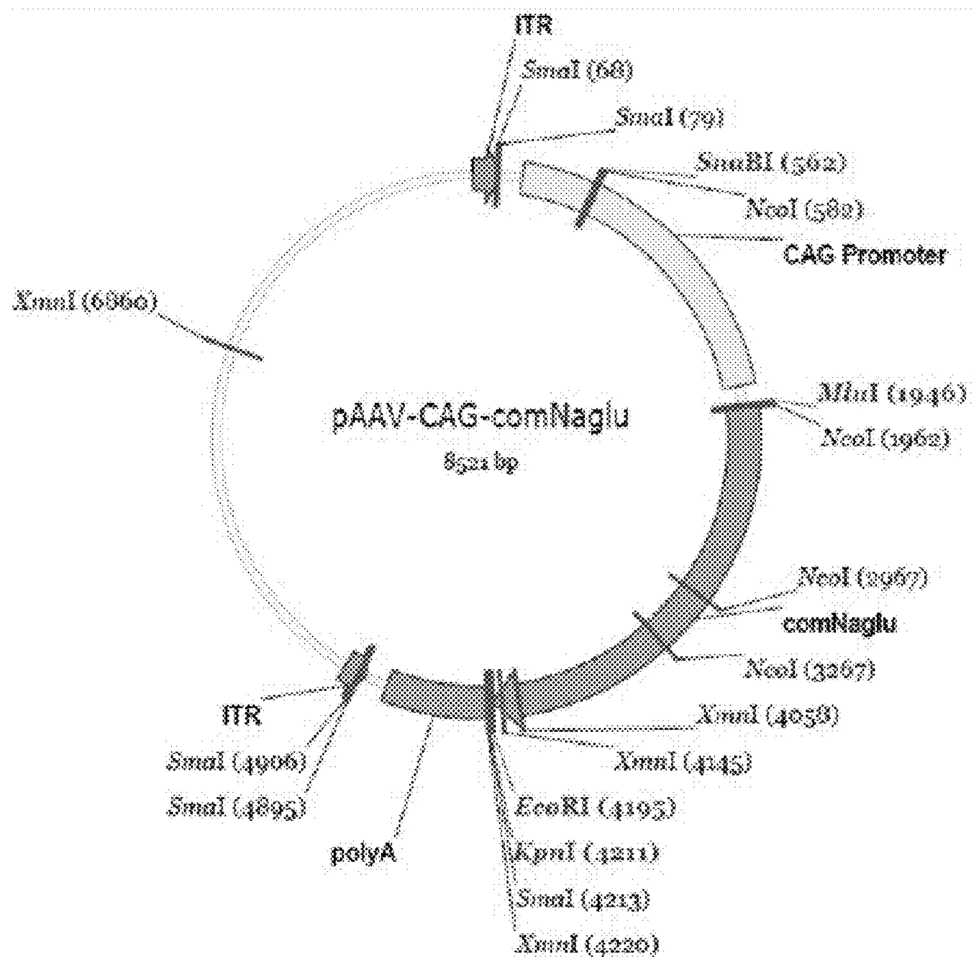
FIG. 23. Schematic representation of the plasmid pAAV-CAG-comNaglu (A) and schematic representation of the genome of the recombinant AAV vector AAV9-CAG-comNaglu (B).

The MluI/EcoRI optimized murine N-acetylglucosaminidase, alpha CDS fragment was excised from the pMA-RQ plasmid and subsequently cloned between the MluI and EcoRI restrictions sites of the AAV backbone plasmid pAAV-CAG. The resulting plasmid was named pAAV-CAG-comNaglu. See SEQ ID NO: 7 and FIG. 23 A.

Example 10: Production of AAV9-CAG-comNaglu

Vectors AAV9-CAG-comNaglu (SEQ ID NO: 11 and FIG. 23 B) were generated by helper virus-free transfection of HEK293 cells using three plasmids with modifications. See Matsushita, 1998, supra and Wright, 2005, supra. Cells were cultured to 70% confluence in roller bottles (RB) (Corning, Corning, N.Y., US) in DMEM supplemented with 10% FBS and then co-transfected with: 1) a plasmid carrying the expression cassette flanked by AAV2 ITRs (pAAV-CAG-comNaglu); 2) a plasmid carrying the AAV2 rep and the AAV9 cap genes (pREP2CAP9); and 3) a plasmid carrying the adenovirus helper functions. Vectors were purified by two consecutives cesium chloride gradients using either a standard protocol or an optimized protocol as previously described. See Ayuso, 2010, supra. Vectors were dialyzed against PBS, filtered, titred by qPCR and stored at −80° C. until use.

Example 11: Construction of pAAV-CAG-cocNaglu

The CDS for canine N-acetylglucosaminidase, alpha (NCBI Reference Sequence: XM_548088.4) was subjected to sequence optimization (GeneArt; Life Technologies). The optimized CDS was received cloned inside the plasmid pMA-RQ (AmpR) flanked by MluI and EcoRI restriction sites at 5' and 3', respectively.

Figure 24:
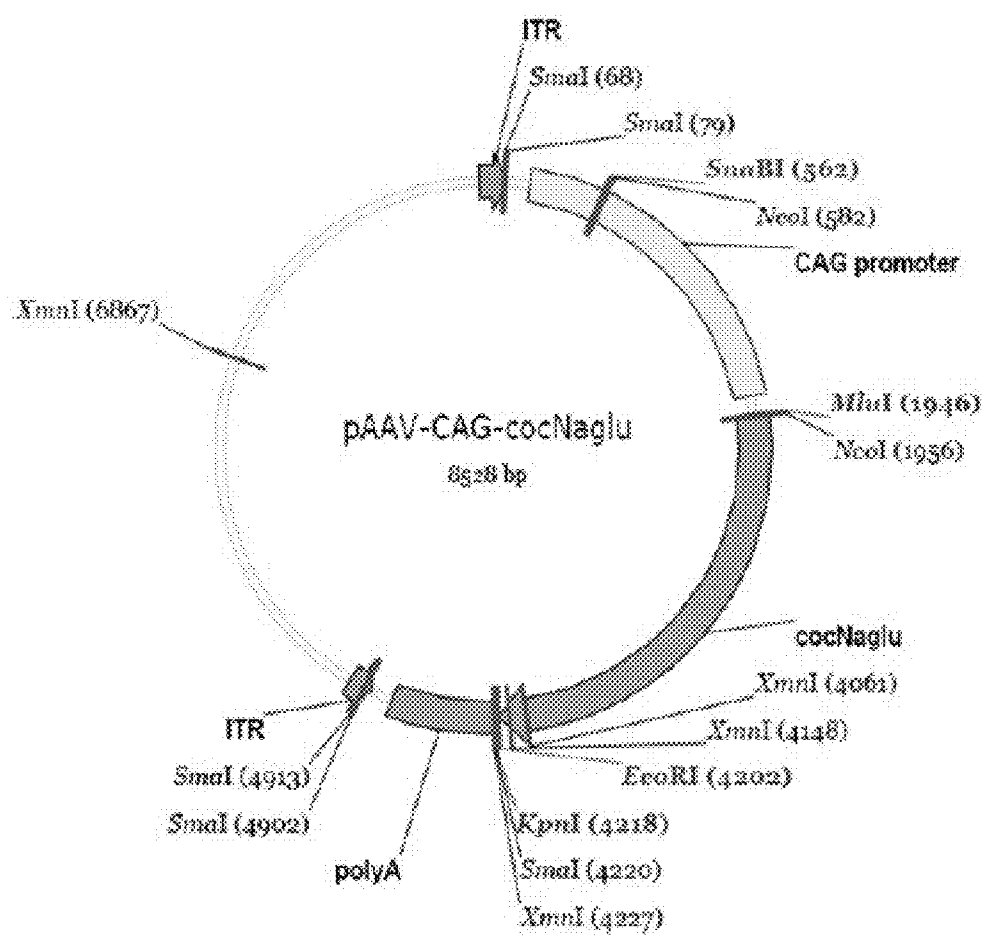
FIG. 24. Schematic representation of the plasmid pAAV-CAG-cocNaglu (A) and schematic representation of the genome of the recombinant AAV vector AAV9-CAG-cocNaglu (B).

The MluI/EcoRI optimized canine N-acetylglucosaminidase, alpha CDS fragment was excised from the pMA-RQ plasmid and subsequently cloned between the MluI and EcoRI restrictions sites of the AAV backbone plasmid pAAV-CAG. The resulting plasmid was named pAAV-CAG-cocNaglu. See SEQ ID NO: 8 and FIG. 24 A.

Example 12: Production of AAV9-CAG-cocNaglu

Vectors AAV9-CAG-cocNaglu (SEQ ID NO: 12 and FIG. 24 B) were generated by helper virus-free transfection of HEK293 cells using three plasmids with modifications. See Matsushita, 1998, supra and Wright, 2005, supra. Cells were cultured to 70% confluence in roller bottles (RB) (Corning, Corning, N.Y., US) in DMEM supplemented with 10% FBS and then co-transfected with: 1) a plasmid carrying the expression cassette flanked by AAV2 ITRs (pAAV-CAG-cocNaglu); 2) a plasmid carrying the AAV2 rep and the AAV9 cap genes (pREP2CAP9); and 3) a plasmid carrying the adenovirus helper functions. Vectors were purified by two consecutives cesium chloride gradients using either a standard protocol or an optimized protocol as previously described. See Ayuso, 2010, supra. Vectors were dialyzed against PBS, filtered, titred by qPCR and stored at −80° C. until use.

Example 13: Hydrodynamic Delivery of the Plasmid pAAV9-CAG-hNaglu

A total dose of 50 μg of the plasmid pAAV9-CAG-hNaglu containing the wild-type human N-acetylglucosaminidase, alpha expressing cassette were administered to 2-month-old MPSIIIB mice via hydrodynamic tail vein (HDTV) injection. This technique targets expression of the delivered plasmid to the liver. See Liu et al., Gene Ther. 1990; 6(7):1258-66.

One week post plasmid delivery, a considerable increase in N-acetylglucosaminidase, alpha activity over pre-treatment levels was documented in the liver and serum of all the animals administered with wild-type human N-acetylglucosaminidase, alpha-coding plasmids. See FIGS. 1A and 1B. No activity was detected in MPSIIIB animals injected with saline solution. The levels of N-acetylglucosaminidase, alpha activity observed in the liver and serum of treated animals corresponded to 150% and 1700%, respectively, of the mean value of activity measured in the liver and serum of WT animals, which was set to 100%. See FIGS. 1A and 1B.

Example 14: Intravenous Delivery of AAV9-CAG-hNaglu

A total dose of $5\times10^{11}$ vector genomes of AAV9-CAG-hNaglu vectors was administered to 2-month-old MPSIIIB mice via tail vein injection.

Figure 2:
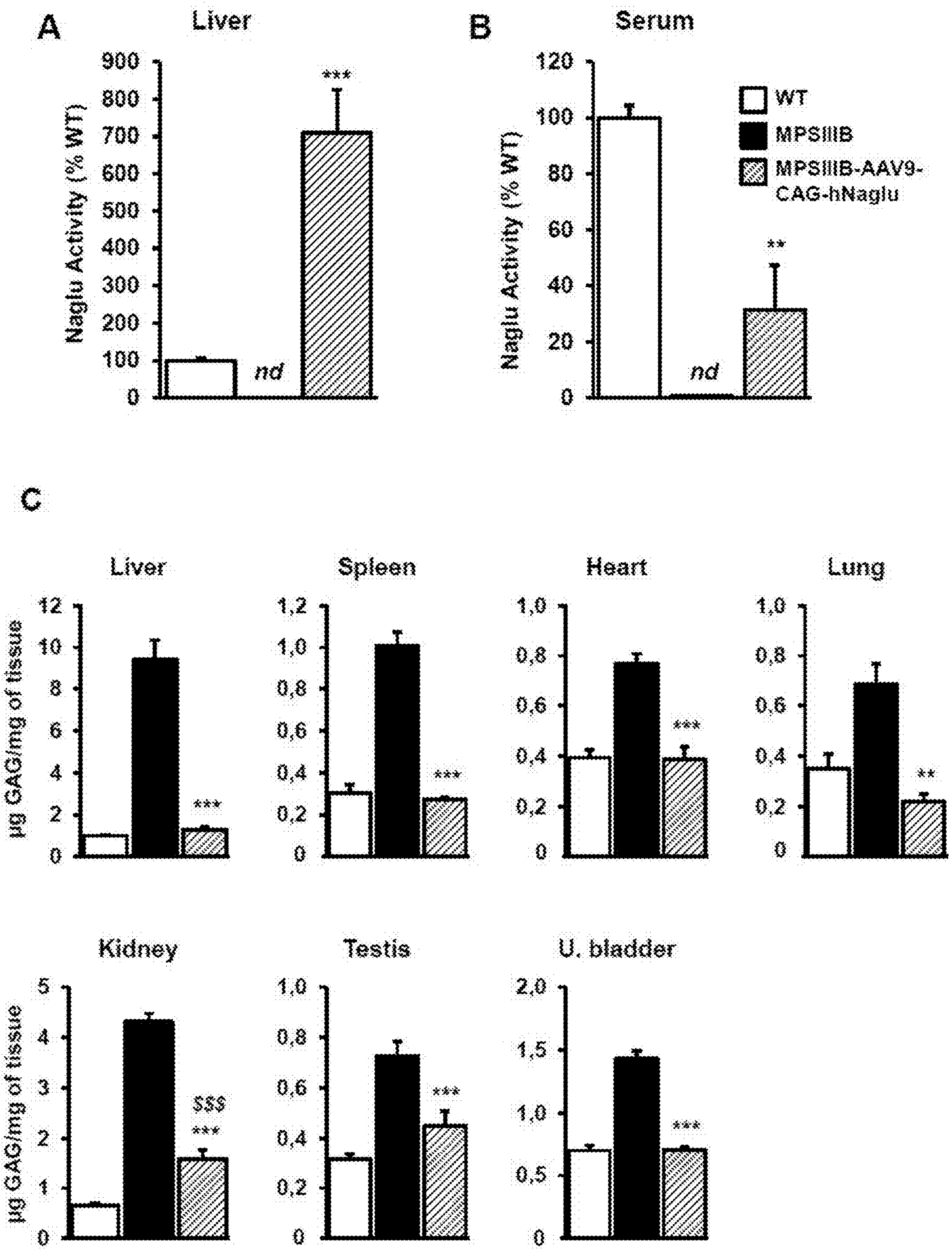
FIG. 2. Intravenous (IV) delivery of AAV9 vectors coding for human N-acetylglucosaminidase, alpha (AAV9-CAG-hNaglu). N-acetylglucosaminidase, alpha activity in the liver (A) and in serum (B) of wild-type (healthy) mice, untreated MPSIIIB mice and MPSIIIB mice treated with an IV injection of $5\times10^{11}$ vg of AAV9-CAG-hNaglu. (C) Glycosaminoglycan (GAG) quantification in somatic organs. Values are means±SEM of 5 to 8 mice per group. $$$ P<0.001 vs. WT,  P<0.01, * P<0.001 vs. untreated MPSIIIB nd: not detected.
Figure 3:
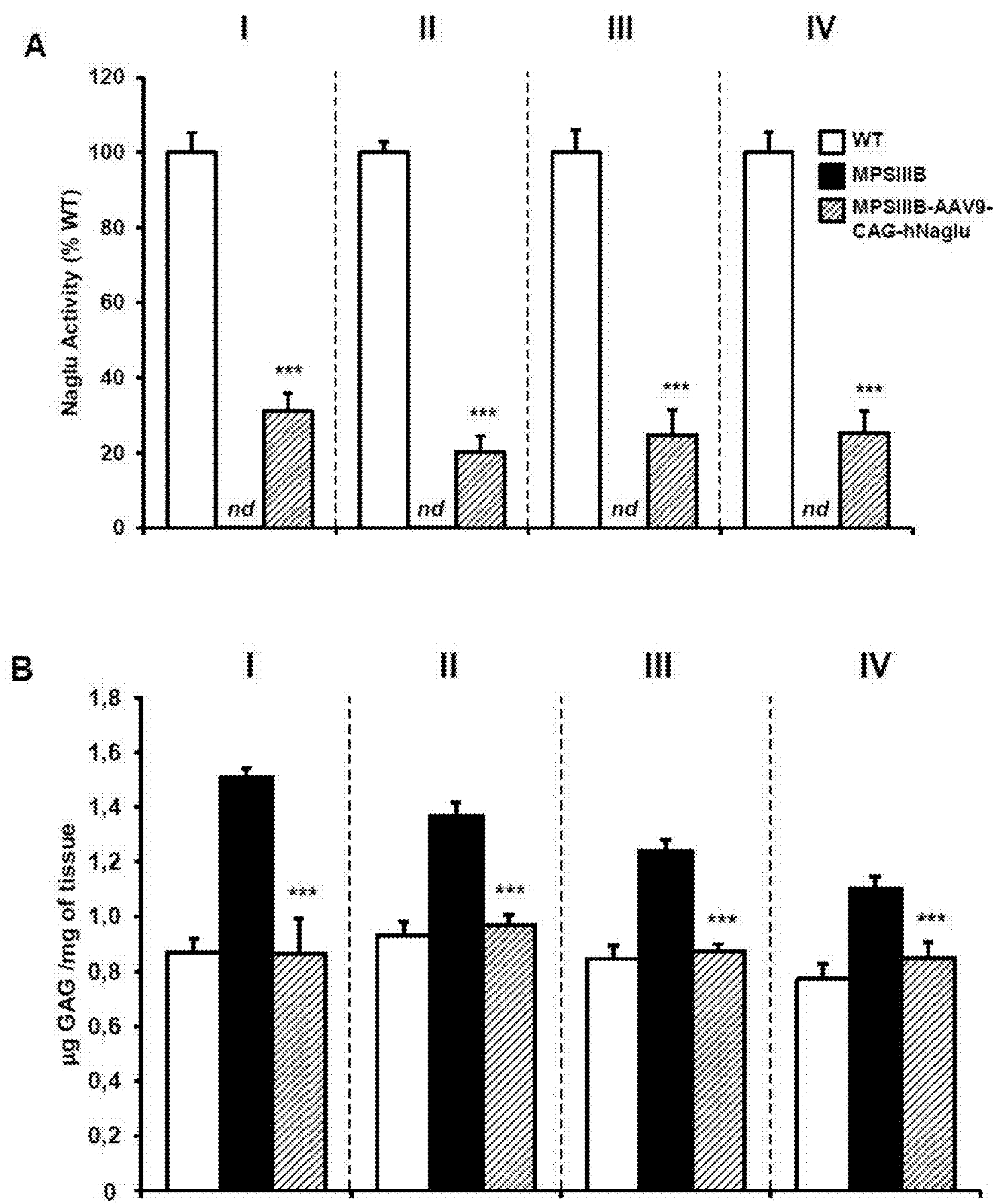
FIG. 3. Intravenous delivery of AAV9 vectors coding for human N-acetylglucosaminidase, alpha (AAV9-CAG-hNaglu). (A) N-acetylglucosaminidase, alpha activity in different parts of the brain (I-IV) of wild-type (healthy) mice, untreated MPSIIIB mice and MPSIIIB mice treated with an IV injection of $5\times10^{11}$ vg of AAV9-CAG-hNaglu. (B) Glycosaminoglycan (GAG) quantification in the same parts of the brain. Values are means±SEM of 5 to 8 mice per group. * P<0.001 vs. untreated MPSIIIB nd: not detected FIG. 4. Intravenous delivery of AAV9 vectors coding for optimized human N-acetylglucosaminidase, alpha (AAV9-CAG-cohNaglu). N-acetylglucosaminidase, alpha activity in the liver (A) and serum (B) of wild-type (healthy) mice, untreated MPSIIIB mice and MPSIIIB mice treated with an IV injection of $5\times10^{11}$ vg of AAV9-CAG-cohNaglu. (C) Glycosaminoglycan (GAG) quantification in somatic organs. Values are means±SEM of 5 to 8 mice per group. $$$ P<0.001 vs. WT,  P<0.01, *** P<0.001 vs. untreated MPSIIIB nd: not detected.

Consistent with the high tropism of AAV9 vectors for the liver, two months after administration treated animals showed high levels of N-acetylglucosaminidase, alpha activity in this organ (700% of the activity levels observed in healthy animals), which completely eliminated or considerably reduced the pathological accumulation of GAGs observed in the somatic tissues of untreated MPSIIIB mice. See FIG. 2A-C. In addition, given the high efficiency with which AAV vectors of serotype 9 transduce the brain upon systemic administration, treated animals showed significant levels of N-acetylglucosaminidase, alpha activity (20-30% of healthy mice) in all brain regions analysed. See FIG. 3A. This partial restoration of N-acetylglucosaminidase, alpha activity was sufficient to clear GAG storage from all areas of the brain. See FIG. 3B.

Example 15: Intravenous Delivery of AAV9-CAG-cohNaglu

A total dose of $5\times10^{11}$ vector genomes of AAV9-CAG-cohNaglu vectors was administered to 2-month-old MPSIIIB mice via tail vein injection.

Figure 4:
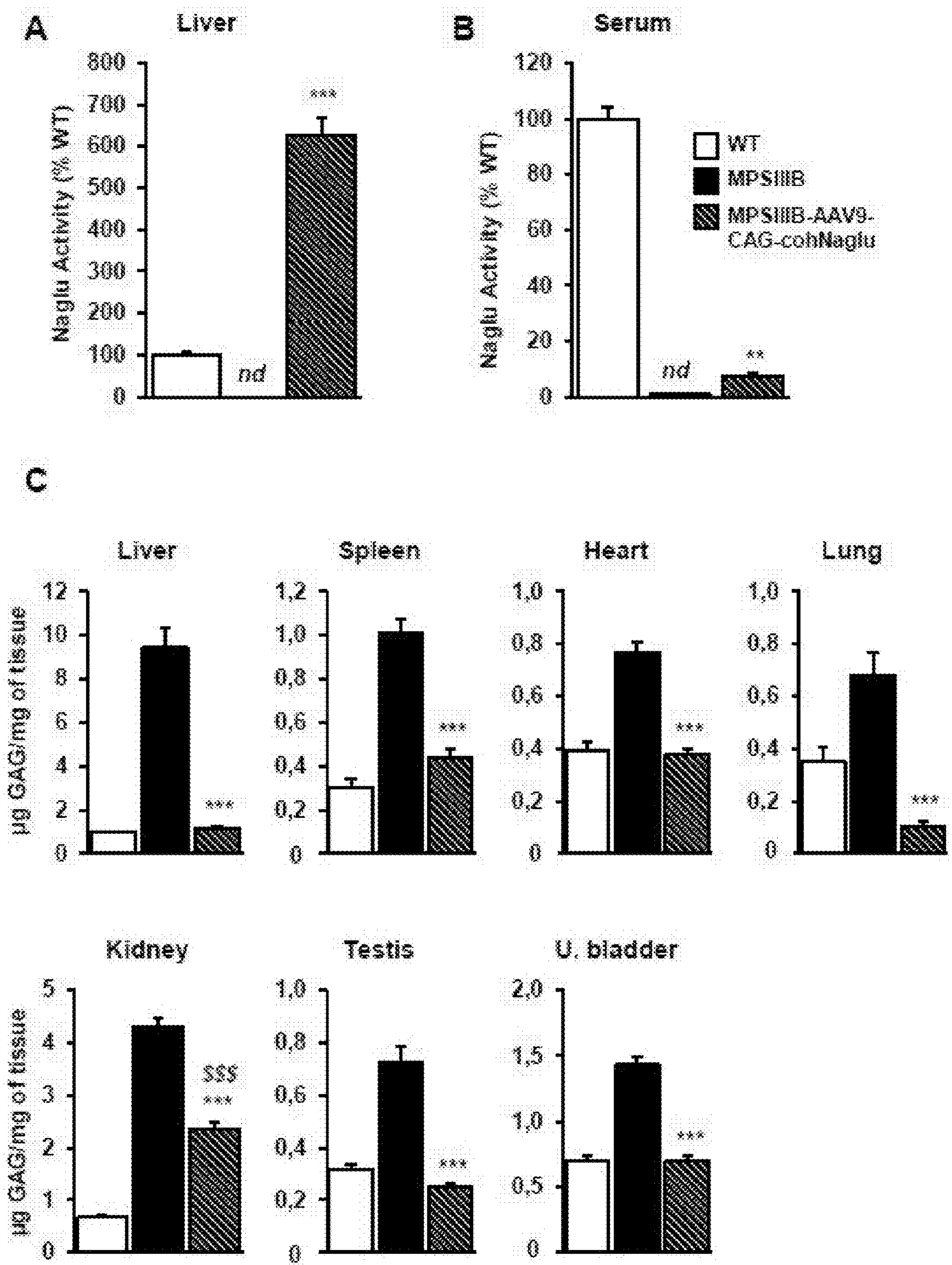
Figure 5:
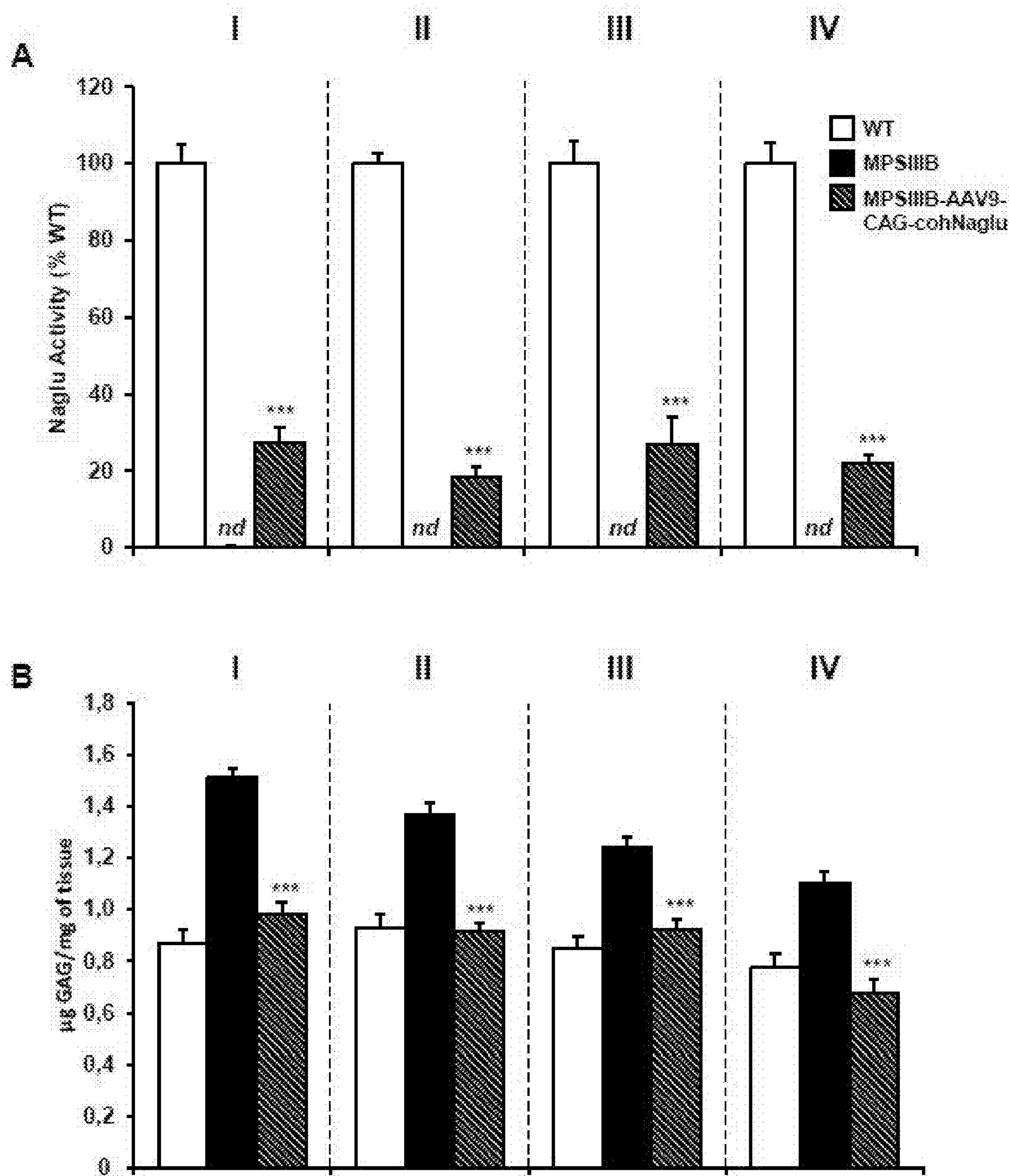
FIG. 5. Intravenous delivery of AAV9 vectors coding for optimized human N-acetylglucosaminidase, alpha (AAV9-CAG-cohNaglu). (A) N-acetylglucosaminidase, alpha activity in different parts of the brain (I-IV) of wild-type (healthy) mice, untreated MPSIIIB mice and MPSIIIB mice treated with an IV injection of $5\times10^{11}$ vg of AAV9-CAG-cohNaglu. (B) Glycosaminoglycan (GAG) quantification in the same parts of the brain. Values are means±SEM of 5 to 8 mice per group. *** P<0.001 vs. untreated MPSIIIB nd: not detected.

Two months after administration, treated animals showed high levels of activity of N-acetylglucosaminidase, alpha in the liver (600% of healthy levels) and a moderate increase (7% of healthy levels) in the levels of activity in serum. See FIGS. 4A and 4B. N-acetylglucosaminidase, alpha production completely eliminated or considerably reduced the pathological accumulation of GAGs observed in the somatic tissues of untreated MPSIIIB mice. See FIG. 4C. In addition, treated animals showed significant levels of N-acetylglucosaminidase, alpha activity (18-27% of healthy mice) in all brain regions analysed. See FIG. 5A. This partial restoration of N-acetylglucosaminidase, alpha activity was sufficient to clear GAG storage from all areas of the brain. See FIG. 5B.

Example 16: Intracisternal Delivery of AAV9-CAG-hNaglu

A total dose of $9.3\times10^9$ vector genomes of AAV9-CAG-hNaglu vector was injected into the cisterna magna of 2-month-old MPSIIIB animals in a total volume of 54

Figure 6:
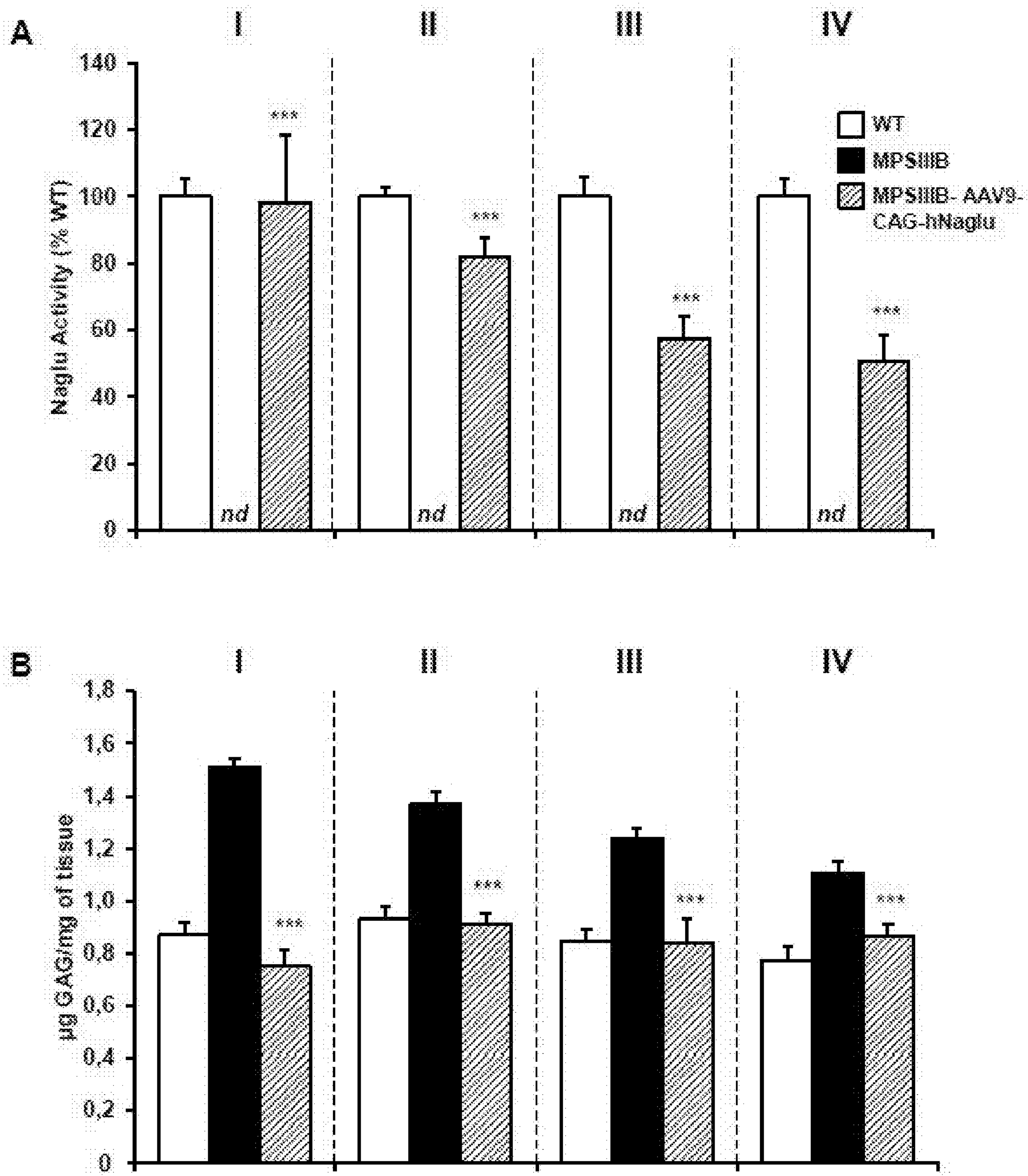
FIG. 6. Intracisternal (IC) delivery of AAV9 vectors coding for human N-acetylglucosaminidase, alpha (AAV9-CAG-hNaglu). (A) N-acetylglucosaminidase, alpha activity in different parts of the brain (I-IV) of wild-type (healthy) mice, untreated MPSIIIB mice and MPSIIIB mice treated with an intracisternal injection of $9.3\times10^{9}$ vg of AAV9-CAG-hNaglu. (B) Quantification of glycosaminoglycans (GAGs) in the same brain areas. Values are means±SEM of 5 to 8 mice per group. *** P<0.001 vs. untreated MPSIIIB nd: not detected.
Figure 7:
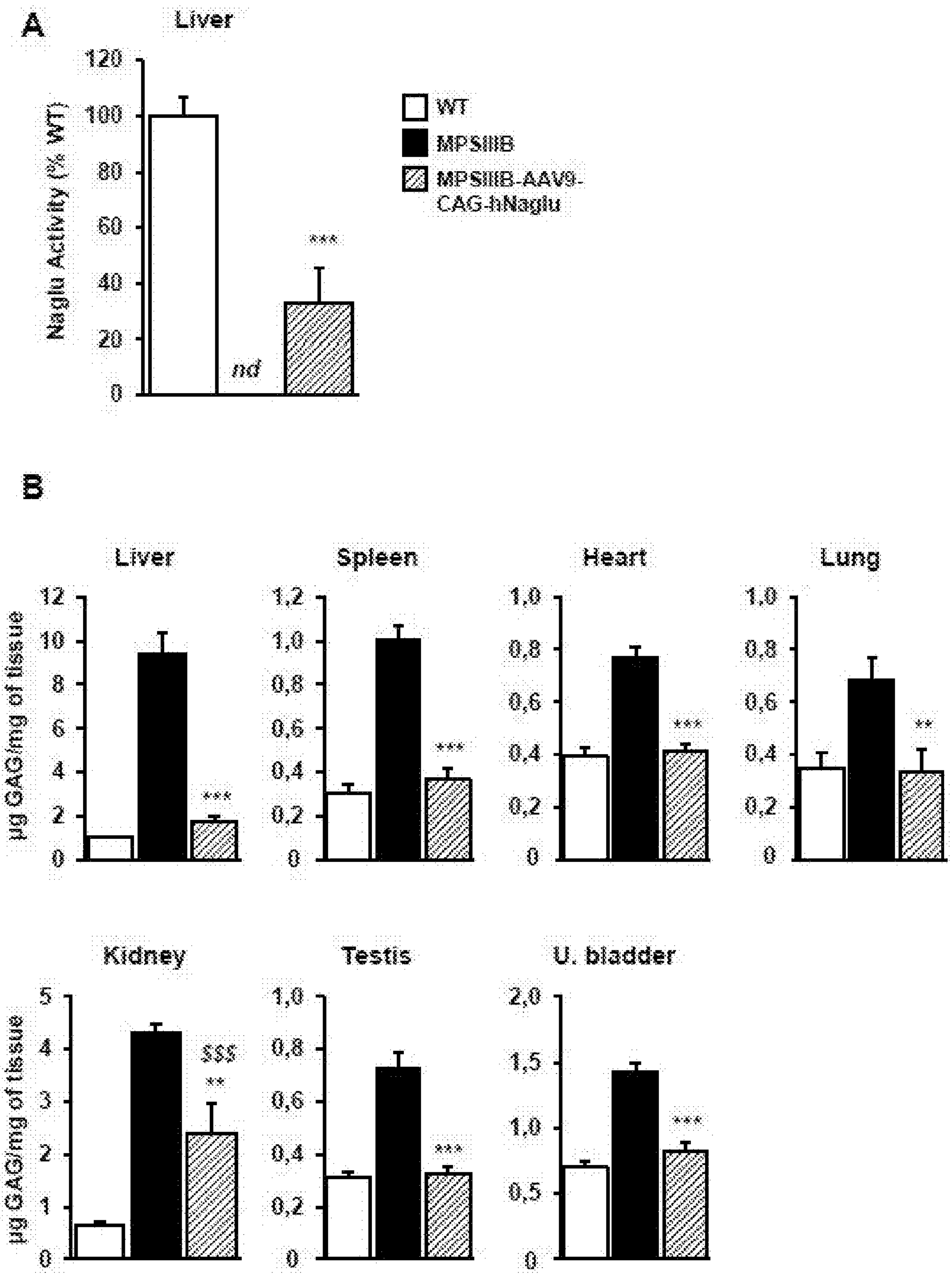
FIG. 7. Intracisternal delivery of AAV9 vectors coding for human N-acetylglucosaminidase, alpha (AAV9-CAG-hNaglu). (A) N-acetylglucosaminidase, alpha activity in the liver of wild-type (healthy) mice and untreated MPSIIIB mice and MPSIIIB mice treated with an intracisternal injection of $9.3\times10^{9}$ vg of AAV9-CAG-hNaglu. (B) Glycosaminoglycan (GAG) quantification in somatic organs. Values are means±SEM of 5 to 8 mice per group. $$$ P<0.001 vs. WT,  P<0.01, * P<0.001 vs. untreated MPSIIIB nd: not detected.

The intra-CSF administration of AAV9-CAG-hNaglu vectors led to high levels of N-acetylglucosaminidase, alpha activity in all brain areas analysed (50-100% of healthy mice); in the most forefront parts of the brain activity reached the levels observed in healthy animals. See FIG. 6A. The excessive storage of GAGs was completely abolished in the brains of treated MPSIIIB mice. See FIG. 6B. When delivered to the CSF, AAV vectors of serotype 9 leak into the bloodstream and transduce the liver. See Haurigot et al., J Clin Invest 2013; 123(8):3254-71. In agreement with this, N-acetylglucosaminidase, alpha activity was detected in the liver of treated MPSIIIB mice at levels of 32% of healthy animals. See FIG. 7A. This increase in N-acetylglucosaminidase, alpha activity mediated the correction of GAG accumulation in liver, spleen, heart, lung, testis and urinary bladder and also significantly diminished GAG storage in kidney. See FIG. 7B.

Example 17: Intracisternal Delivery of AAV9-CAG-cohNaglu

A total dose of $9.3\times10^9$ vector genomes of AAV9-CAG-cohNaglu vector was injected into the cisterna magna of 2-month-old MPSIIIB animals in a total volume of 5 µl.

Figure 8:
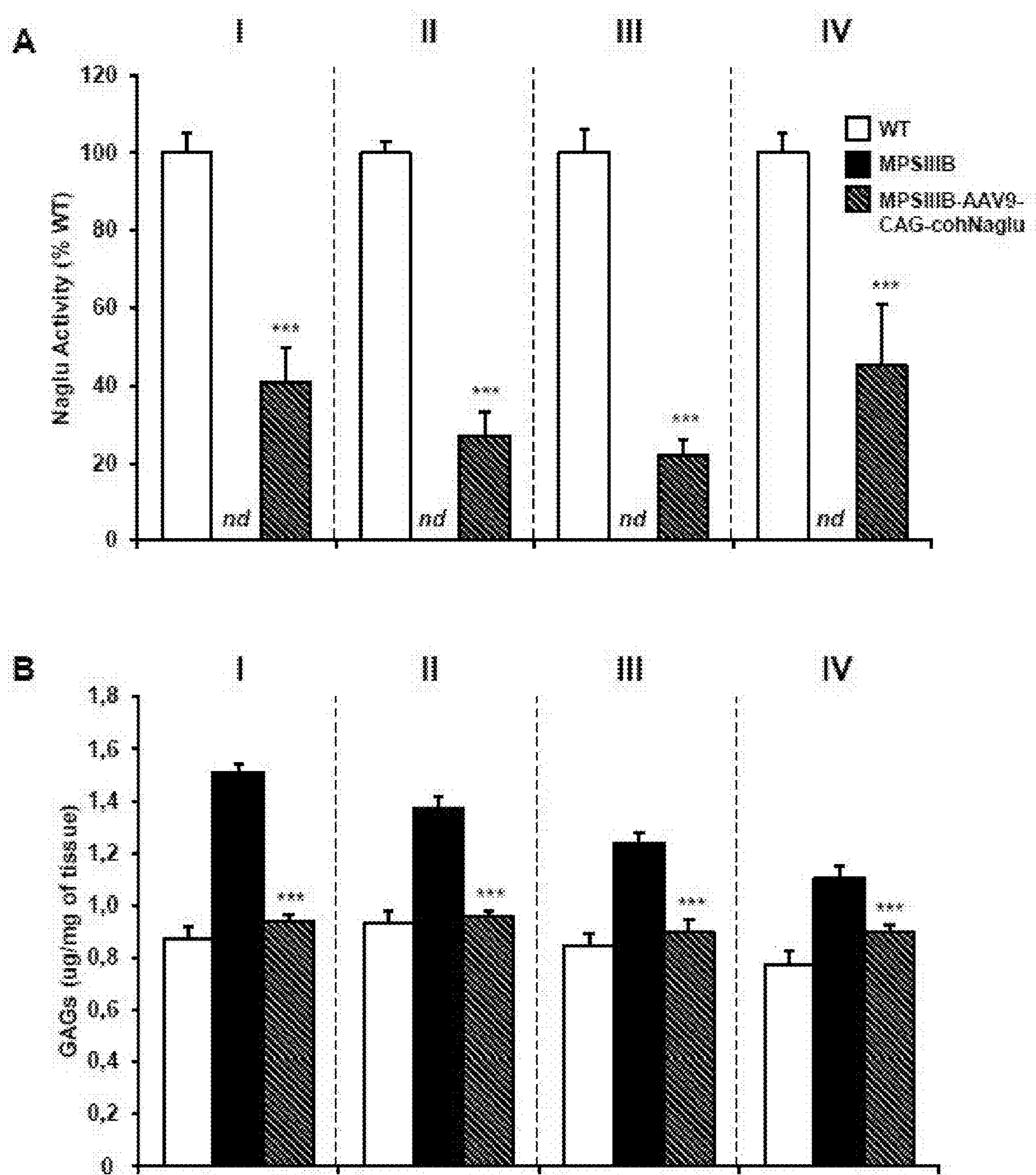
FIG. 8. Intracisternal delivery of AAV9 vectors coding for optimized human N-acetylglucosaminidase, alpha (AAV9-CAG-cohNaglu). (A) N-acetylglucosaminidase, alpha activity in different parts of the brain (I-IV) of wild-type (healthy) mice, untreated MPSIIIB mice and MPSIIIB mice treated with an intracisternal injection of $9.3\times10^{9}$ vg of AAV9-CAG-cohNaglu. (B) Quantification of glycosaminoglycans (GAGs) in the same brain areas. Values are means±SEM of 5 to 8 mice per group. *** P<0.001 vs. untreated MPSIIIB nd: not detected.
Figure 9:
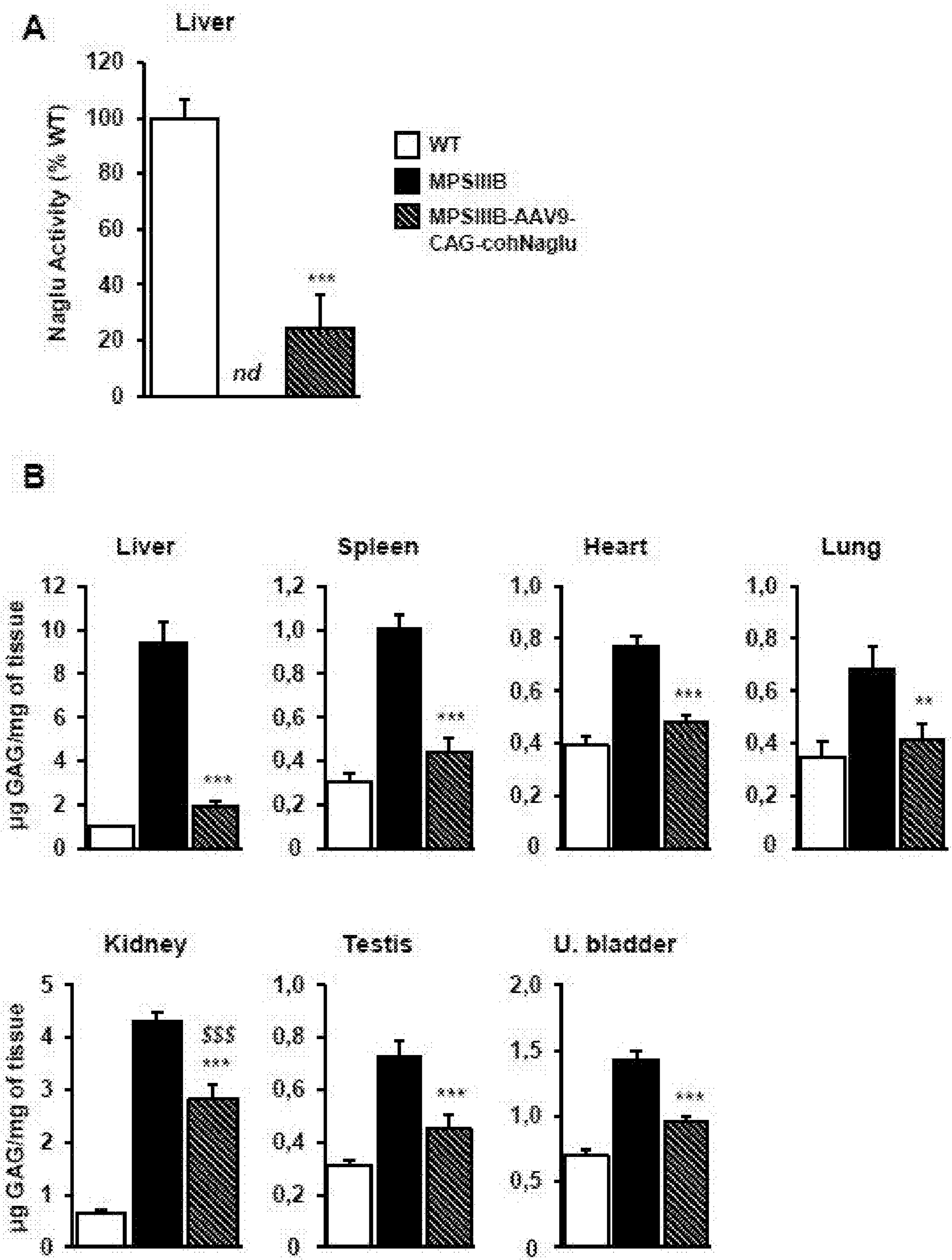
FIG. 9. Intracisternal delivery of AAV9 vectors coding for optimized human N-acetylglucosaminidase, alpha (AAV9-CAG-cohNaglu). (A) N-acetylglucosaminidase, alpha activity in the liver of wild-type (healthy) mice, untreated MPSIIIB mice and MPSIIIB mice treated with an intracisternal injection of $9.3\times10^{9}$ vg of AAV9-CAG-cohNaglu. (B) Glycosaminoglycan (GAG) quantification in somatic organs. Values are means±SEM of 5 to 8 mice per group. $$$ P<0.001 vs. WT,  P<0.01, * P<0.001 vs. untreated MPSIIIB nd: not detected.

Intracisternal administration of AAV9-CAG-cohNaglu vectors led a considerable increase in the levels of N-acetylglucosaminidase, alpha activity, which ranged from 22 to 45% of healthy values, in all brain regions analysed. See FIG. 8A. Accordingly, pathological accumulation of GAGs was completely reverted in all brains regions of treated MPSIIIB mice. See FIG. 8B. N-acetylglucosaminidase, alpha activity also increased in the liver of treated MPSIIIB mice to 25% of healthy animals. See FIG. 9A. This increase in N-acetylglucosaminidase, alpha activity mediated the correction of GAG accumulation in liver, heart, lung and urinary bladder and also significantly diminished GAG storage in spleen, testis and kidney. See FIG. 9B.

Example 18: Hydrodynamic Delivery of the Plasmid pAAV9-CAG-cohNaglu-Version2

A total dose of 50 µg of the plasmid pAAV9-CAG-cohNaglu-version2 carrying an expression cassette containing an optimized version (version2) of human N-acetylglucosaminidase, alpha were administered to 2-month-old MPSIIIB mice via tail hydrodynamic tail vein injection. As aforementioned, this technique targets expression of the delivered plasmid to the liver. See Liu et al., supra.

Figure 10:
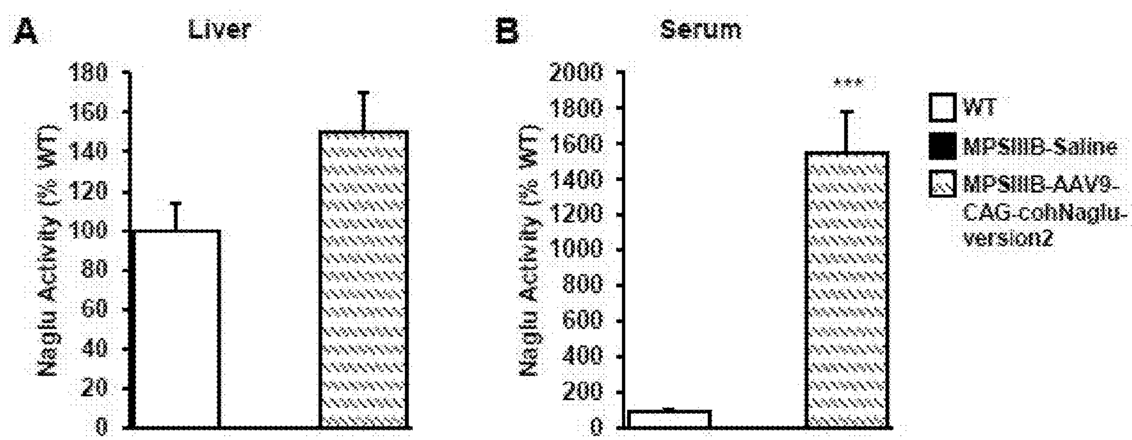
FIG. 10. Hydrodynamic delivery of plasmid encoding for optimized human N-acetylglucosaminidase, alpha-version2 (pAAV-CAG-cohNaglu-version2). Two-month-old MPSIIIB mice were hydrodynamically injected with 50 μg of the plasmid pAAV-CAG-cohNaglu-version2. Histograms depict N-acetylglucosaminidase, alpha (NAGLU) activity measured 1 week post-plasmid administration in liver (A) and serum (B). NAGLU activity of saline-injected WT mice was set to 100%. Values are means±SEM of 3-4 mice per group. *** P<0.001 vs. WT.

One week post plasmid delivery, N-acetylglucosaminidase, alpha activity was increased over pre-treatment levels in the liver and serum of all the animals that received a hydrodynamic injection of the plasmid containing the optimized version2 of N-acetylglucosaminidase, alpha-coding sequence. See FIGS. 10A and 10B. No activity was detected in MPSIIIB animals injected with saline solution. In treated animals, liver and serum N-acetylglucosaminidase, alpha activity reached levels that were 150% and 1500%, respectively, of the mean value of activity observed in WT animals (set to 100%). See FIGS. 10A and 10B.

Example 19: Hydrodynamic Delivery of the Plasmid pAAV9-CAG-cohNaglu-Version3

A total dose of 50 µg of the plasmid pAAV9-CAG-cohNaglu-version3 containing the a codon optimized version (version3) human N-acetylglucosaminidase, alpha expressing cassette were administered to 2-month-old MPSIIIB mice via tail hydrodynamic tail vein injection. As aforementioned, this technique targets expression of the delivered plasmid to the liver. See Liu et al., supra.

Figure 11:
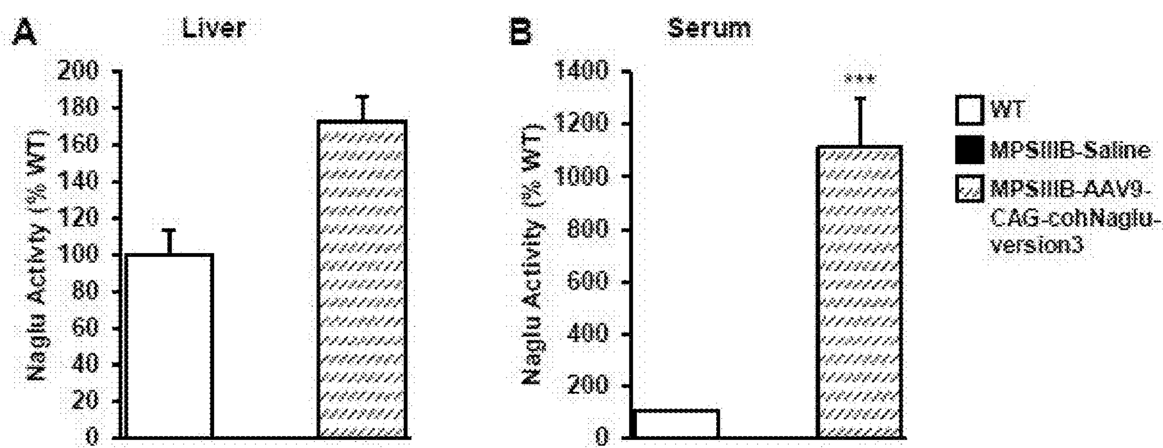
FIG. 11. Hydrodynamic delivery of plasmid encoding for optimized human N-acetylglucosaminidase, alpha-version3 (pAAV-CAG-cohNaglu-version3). Two-month-old MPSIIIB mice were hydrodynamically injected with 50 μg of the plasmid pAAV-CAG-cohNaglu-version3. Histograms depict N-acetylglucosaminidase, alpha (NAGLU) activity measured 1 week post plasmid administration in liver (A) and serum (B). NAGLU activity of saline-injected WT mice was set to 100%. Values are means±SEM of 3-4 mice per group.*** P<0.001 vs. WT.

One week post plasmid delivery, a considerable increase in N-acetylglucosaminidase, alpha activity over pre-treatment levels was documented in the liver and serum of all the animals administered with the plasmid carrying the expression cassette that contained the version3 of codon-optimized human N-acetylglucosaminidase, alpha-coding sequence. See FIGS. 11A and 11B. No activity was detected in MPSIIIB animals injected with saline solution. The levels of N-acetylglucosaminidase, alpha activity observed in the liver and serum of treated animals corresponded to 170% and 1100%, respectively, of the mean value of activity determined in the liver and serum of WT animals, which was set to 100%. See FIGS. 11A and 11B.

Example 20: Intracisternal Delivery of AAV9-CAG-comNaglu

A total dose of $3\times10^{10}$ vector genomes of AAV9-CAG-comNaglu vector was injected into the cisterna magna of 2-month-old MPSIIIB animals in a total volume of 10 µl.

AAV9 vector genomes could be detected in all brain areas analysed, as well as in the spinal cord. In peripheral tissues, vector genomes could be detected at considerable gene copy numbers only in the liver, and at low gene copy numbers in the lymph nodes in which the head drains (mandibular lymph nodes). See FIG. 12A-B.

Figure 13:
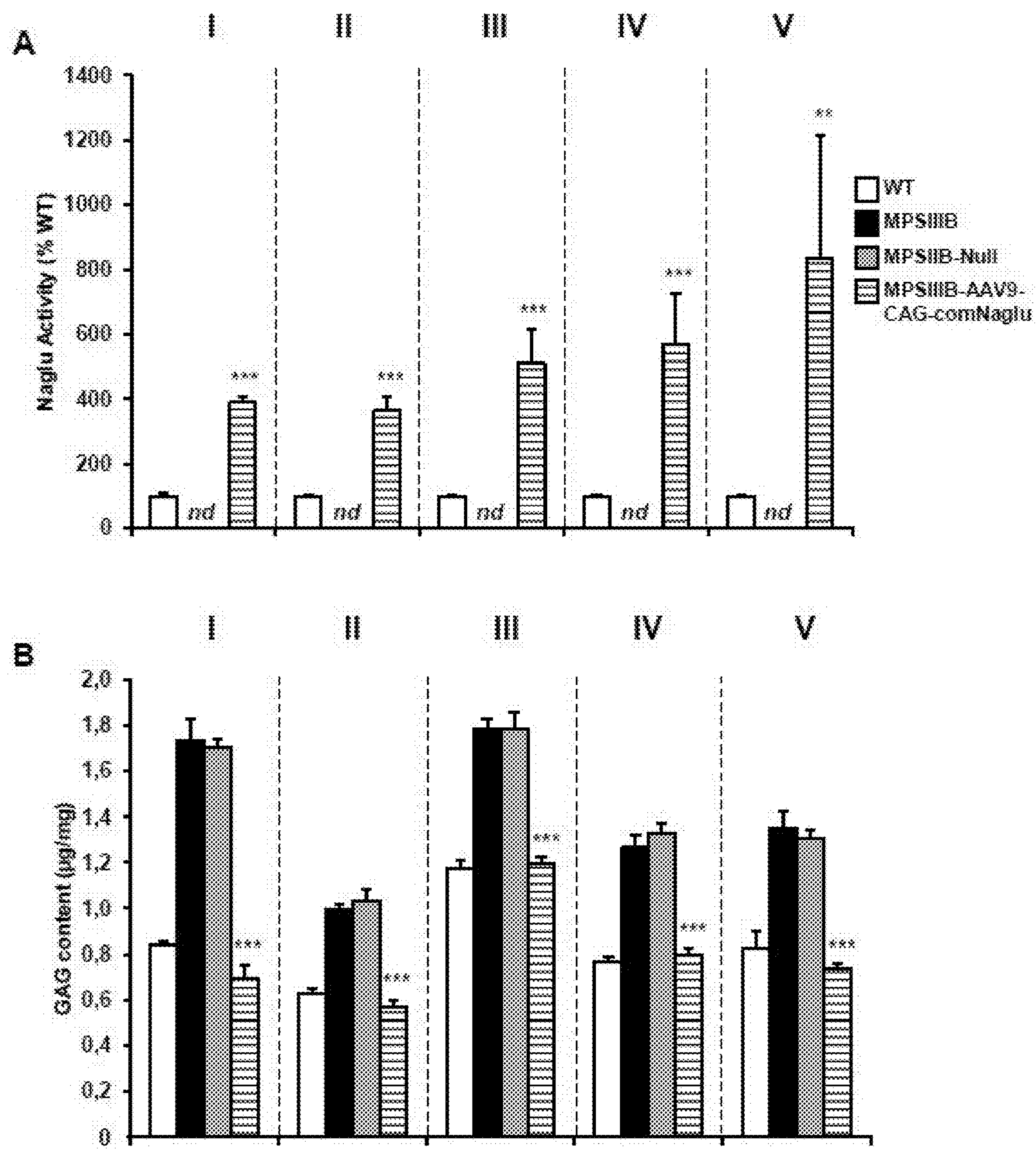
FIG. 13. Intracisternal delivery of AAV9 vectors coding for optimized murine N-acetylglucosaminidase, alpha (AAV9-CAG-comNaglu). (A) N-acetylglucosaminidase, alpha activity in different parts of the brain (I-V) of wild-type (healthy) mice, untreated MPSIIIB mice and MPSIIIB mice administered in the cisterna magna with either $3.9\times10^{10}$ vg of control vector (AAV9-Null) or $3\times10^{10}$ vg of AAV9-CAG-comNaglu. (B) Quantification of glycosaminoglycans (GAGs) in the same brain areas. Values are means±SEM of 4 mice per group.  P<0.01, * P<0.001 vs. MPS IIIB-null. nd: not detected.

The intra-CSF administration of AAV9-CAG-comNaglu vectors led to very high levels of N-acetylglucosaminidase, alpha activity in all brain areas analysed; reaching levels that were several fold higher than those observed in healthy animals in all regions. See FIG. 13A. Three months post vector delivery the lysosomal pathology characteristic of the disease was completely reverted in the brains of treated MPSIIIB mice, as indicated by the normalization of GAG accumulation and of the signal intensity for the lysosomal marker LIMP-2+ in all brain areas analysed. See FIGS. 13B and 14A. Ultrastructural analysis of the occipital cortex and the cerebellum by transmission electron microscopy confirmed the reduction in lysosomal pathology, which was very evident in cortical perineuronal glial cells that appeared distended and full of large storage vesicles in MPSIIIB animals that received control vector, while they had a normal appearance in animals treated with AAV9-CAG-comNaglu.

See FIG. 14B. In LSD, the activity of several lysosomal enzymes aside from that directly affected by the inherited mutation can be altered secondary to perturbation of normal lysosomal homeostasis. See Sardiello et al., Science. 2009; 325:473-477. In the brain of untreated or Null-treated male MPSIIIB mice aged 5 months, the activities of Iduronate 2-sulfatase (IDS), N-sulphoglucosamine sulphohydrolase (SGSH), β-glucuronidase (GUSB), and β-hexosaminidase (HEXB) were significantly increased. See FIG. 14C. Consistent with the reduction in GAG storage observed 3 months after intra-CSF delivery of AAV9-CAG-comNaglu vectors, the activity of brain SGSH, GUSB and HEXB returned to healthy wild-type levels in treated animals. See FIG. 14C.

In agreement with the correction of the lysosomal pathology, all signs of inflammation disappeared from the brains of treated MPSIIIB mice. The signal intensities for the stainings used to detect astrocytosis (GFAP) and microgliosis (BSI-B4) were similar in treated MPSIIIB mice and in healthy animals, as opposed to the signal documented in untreated MPSIIIB mice that showed a clear upregulation of these markers of neuroinflammation. See FIGS. 15A and 15B. To further assess the efficacy of intra-CSF AAV9-CAG-comNaglu gene therapy on CNS inflammation, a gene expression profiling study using the Affimetrix® microarray platform on total RNA isolated from WT and AAV9-CAG-comNaglu or AAV9-Null-treated MPSIIIB encephalon was performed. After data processing and filtering, 94 genes were found to be differentially expressed among the three groups. When Gene Ontology (GO) enrichment analysis was used to classify differentially expressed genes by biological process, 67 of the 94 genes were annotated with corresponding ontologies. See FIG. 15C. Of these, the vast majority were associated with inflammation and innate immunity or functions that can be attributed to cells involved in these processes. See FIG. 15C. To confirm this observation, we used Cell Type Enrichment (CTEN) analysis to assess the contribution of different cell types to the observed changes in transcript levels. This software considers there is enrichment of a specific cell type if a software-defined score is greater than 2. The highest score for our data set was obtained for microglial cells (score=60), a result in agreement with the important role attributed to microglia in neurodegenerative diseases and in MPSIII. See Ohmi et al., Proc Natl Acad Sci USA. 2003; 100:1902-1907, McGeer et al. Alzheimer Dis Assoc Disord. 1998; 12 (Suppl. 2):S1-E16, Derecki et al., Nature. 2012; 484: 105-109, DiRosario et al., J Neurosci Res. 2009; 87:978-990, Archer, et al., J Inherit Metab Dis. 2014; 37:1-12. When the effect of intra-CSF delivery of AAV9-CAG-comNaglu vectors was evaluated, a striking change in the profile of gene expression with respect to AAV9-Null-injected animals was observed. Three months after vector administration, the vast majority of genes in treated MPSIIIB mice had transcript levels that resembled those of healthy littermates. Almost 90% of the genes differentially expressed in untreated MPSIIIB mice showed a correction in their transcript levels of at least 50% following AAV9-CAG-comNaglu treatment and in 60% of them the correction was of 75%. Similar or slightly higher degrees of normalization in transcript levels were observed when the set of genes that the CTEN software had assigned to microglia was analysed separately. See FIG. 15D. This observation supports the idea that microglia is largely responsible for the profile of gene expression observed in MPSIIIB and is in agreement with the complete reversal of microgliosis documented in treated animals.

Figure 16:
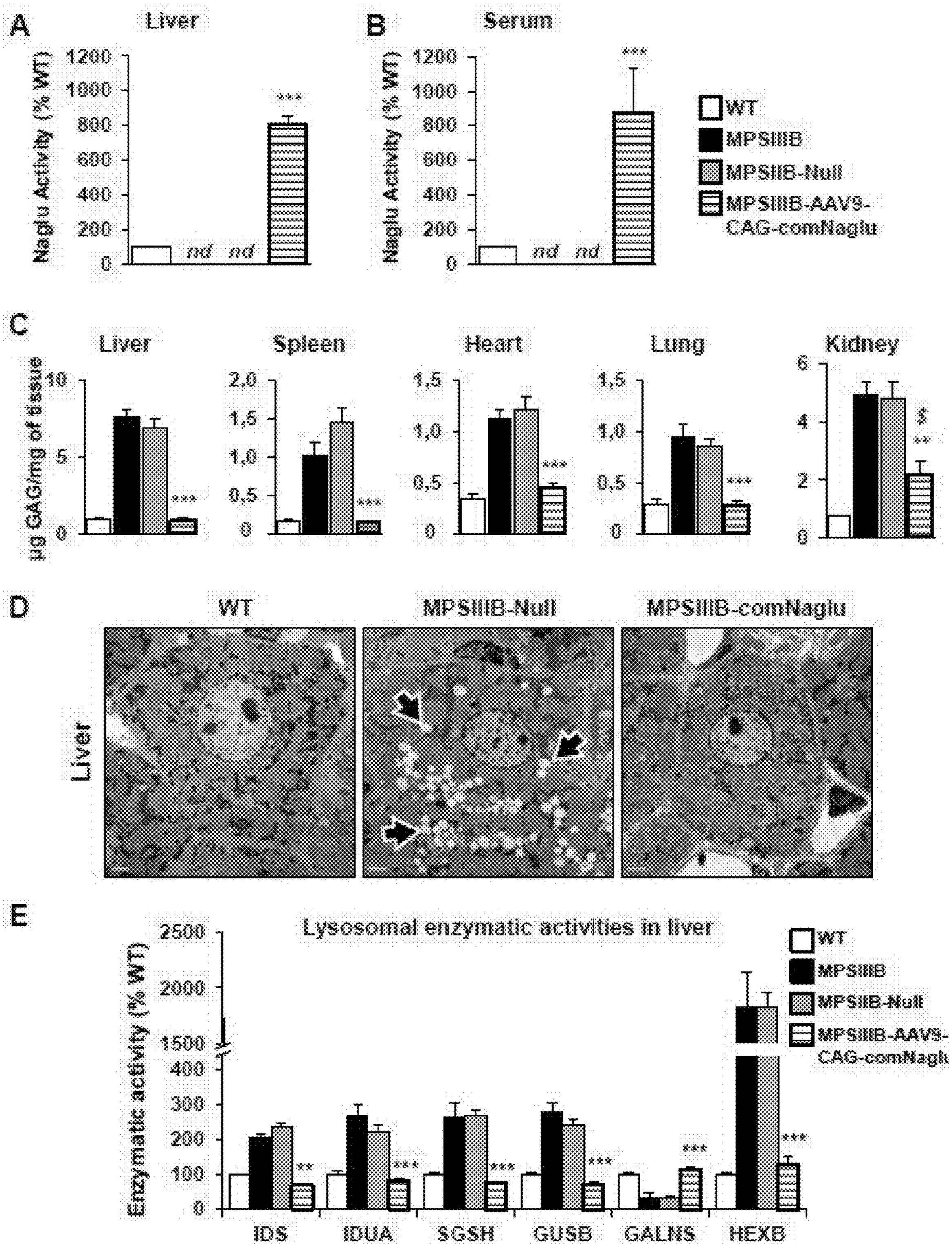
FIG. 16. Intracisternal delivery of AAV9 vectors coding for optimized murine N-acetylglucosaminidase, alpha (AAV9-CAG-comNaglu). N-acetylglucosaminidase, alpha activity in the liver (A) and serum (B) of wild-type (healthy) mice, untreated MPSIIIB mice and MPSIIIB mice administered in the cisterna magna with either $3.9\times10^{10}$ vg of control vector (AAV9-Null) or $3\times10^{10}$ vg of AAV9-CAG-comNaglu. (C) Glycosaminoglycan (GAG) quantification in somatic organs. Values are means±SEM of 4 to 8 mice per group. $ P<0.05 vs. WT,  P<0.01,  P<0.001 vs. untreated MPSIIIB nd: not detected. (D) Electron microscopy analysis of the liver. Multiple electro-lucent vacuoles (arrows) can be observed in the cytoplasm of hepatocytes from MPSIIIB mice treated with null vector and these vesicles disappear in animals treated with AAV9-CAG-mNaglu. (E) Activity of other lysosomal enzymes in liver extracts obtained from the same cohorts of animals as in (A and B). IDS, iduronate-2-sulfatase, IDUA, iduronidase, alpha-L-, SGSH, N-sulfoglucosamine sulfohydrolase, GUSB, glucuronidase, beta, HEXB, hexosaminidase B. WT enzyme activities were set to 100%. Values are means±SEM of 4 mice per group.  P<0.01 and * P<0.001 vs. MPSIIIB-Null.
Figure 17:
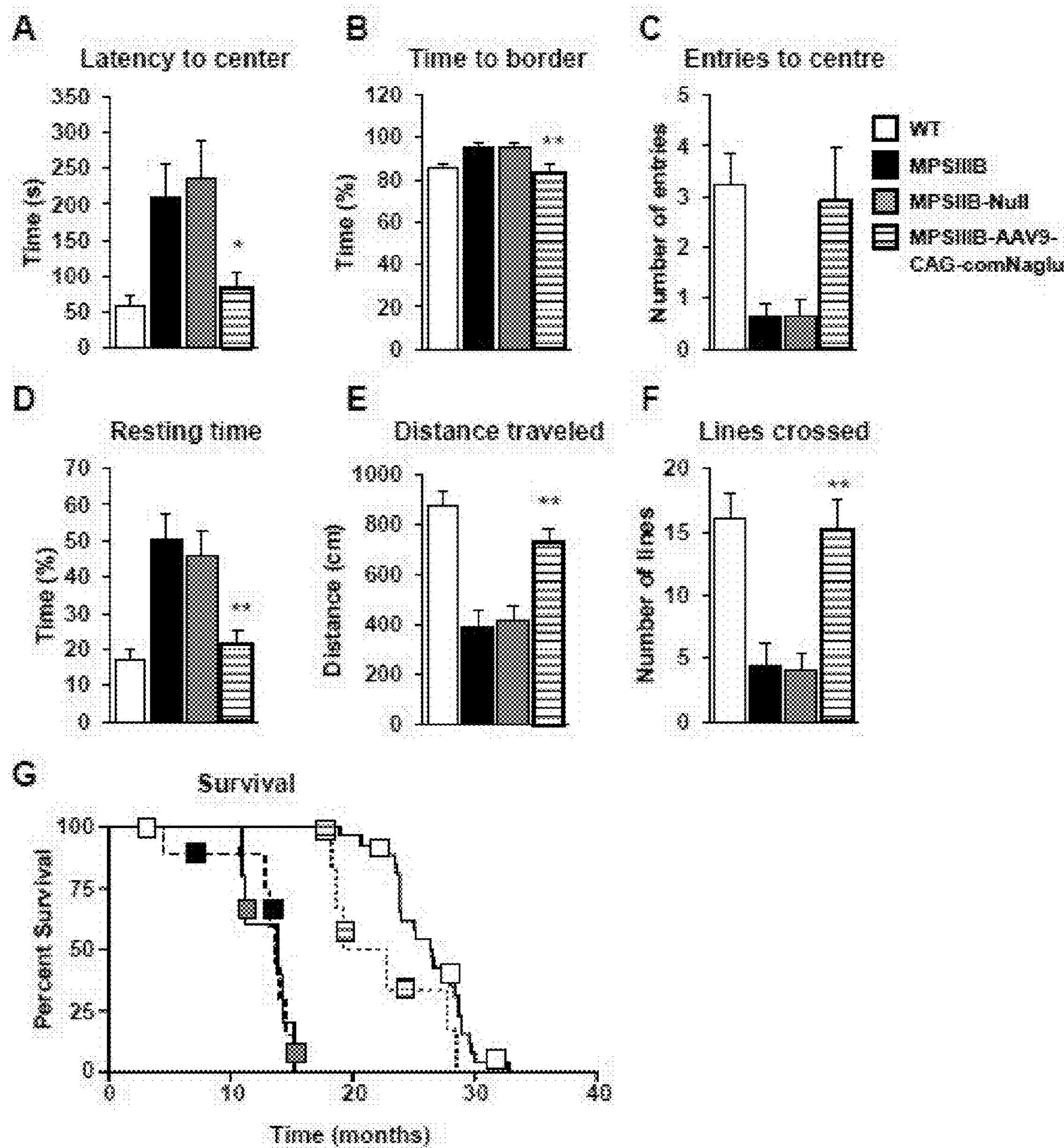
FIG. 17. Intracisternal delivery of AAV9 vectors coding for optimized murine N-acetylglucosaminidase, alpha (AAV9-CAG-comNaglu). Behavioural evaluation in naïve-tested wild-type (healthy) mice, untreated MPSIIIB mice and MPSIIIB mice administered in the cisterna magna with either $3.9\times10^{10}$ vg of control vector (AAV9-Null) or $3\times10^{10}$ vg of AAV9-CAG-comNaglu. Data correspond to the locomotor and exploratory activity recorded during the first 2 minutes, and are represented as the mean±SEM of 10 to 15 animals per group. (A) Latency to centre, (B) Time in border, (C) Entries to centre, (D) Resting time, (E) Total distance traveled, (F) Total number of lines crossed. *P<0.05 and **P<0.01 vs. MPSIIIB-null. (G) Kaplan-Meier survival analysis in WT (n=23), untreated MPSIIIB mice (n=12), MPSIIIB mice injected with $3.9\times10^{10}$ vg of AAV9-Null (n=5) or $3\times10^{9}$ vg of AAV9-CAG-comNaglu (n=8). Treatment with AAV9-CAG-comNaglu gene therapy considerably extended the lifespan of MPSIIIB animals. P=0.0007 for AAV9-CAG-comNaglu-treated MPSIIIB mice vs. MPSIIIB-null.

AAV9 vectors administered to the CSF leak to the periphery and transduce the liver. See FIG. 9 and Haurigot et al., supra. Accordingly, an increase in N-acetylglucosaminidase, alpha activity was documented in the liver and serum of MPSIIIB mice treated with AAV9-CAG-comNaglu, reaching levels of approximately 800% of the levels observed in healthy animals. See FIGS. 16A and 16B. The levels of enzymatic activity in serum correlated well with those of activity in the liver of treated mice, suggesting that the liver was the main source of circulating enzyme. When the somatic efficacy of the therapy was evaluated through quantification of the GAG content in different organs, a full normalization was observed in most tissues, including liver, spleen, heart, and lung, with the exception of kidney, in which a >50% reduction of GAGs was observed. See FIG. 16C. The ultrastructural analysis of the liver in the different experimental groups showed the complete disappearance of the storage vacuoles that are characteristic of the MPSIIIB disease from the hepatocytes of MPSIIIB mice treated with AAV9-CAG-comNaglu. See FIG. 16D. As observed in CNS, the clearance of storage material from the lysosomal compartment led to restoration of the activity of other lysosomal enzymes. In liver of untreated or Null-treated MPSIIIB mice, the activities of α-iduronidase (IDUA), iduronate 2-sulphatase (IDS), SGSH, GUSB and HEXB were altered. See FIG. 16E. Three months following AAV9-mediated NAGLU gene transfer, the activity of all these enzymes returned to normal levels, further supporting the concept that CSF gene transfer of NAGLU through AAV9-CAG-comNaglu can reverse disease phenotype also in peripheral organs. See FIG. 16E.

The impact of the intra-CSF administration of AAV9-CAG-comNaglu on behaviour was assessed with the open field test, which evaluates the general locomotor and exploratory activity of mice in unknown surroundings. Untreated and AAV9-null-treated MPSIIIB mice displayed reduced exploratory activity compared with healthy mice in terms of the latency to enter the centre, the time spent in the border, the number of entries to the centre, the resting time, the total distance traveled, and the number of lines crossed. Intracisternal administration of AAV9-CAG-comNaglu completely corrected behavioural deficits. See FIGS. 17A-F.

Furthermore, treatment with AAV9-CAG-comNaglu significantly extended the lifespan of MPSIIIB mice. By 15 months of age, all untreated MPSIIIB mice had died while 100% of the animals receiving intracisternal AAV9-CAG-comNaglu were still alive at 18 months of age. See FIG. 17G. Treated MPSIIIB males showed a median survival of 21 months, compared with a 13.8 month median survival for AAV9-null MPSIIIB males; P=0.0007. Median survival for healthy male was 26.6 months. The normalization of behavioural responses and the greater survival of treated MPSIIIB mice further demonstrate the therapeutic efficacy of AAV9-CAG-comNaglu.

Example 21: Intracisternal Delivery of AAV9-CAG-cocNaglu to Dogs

The first step towards the clinical application of a gene therapy approach requires the demonstration of its feasibility in a large animal model. We previously demonstrated that the distribution of AAV9 vectors upon intra cerebrospinal fluid administration to Beagle dogs, an animal model with a brain size closer to that of humans, is very similar to that observed in mice receiving an equivalent dose of vector through the same route. See Haurigot et al., supra. Briefly, the administration of $2\times10^{13}$ vg of AAV9 vectors encoding for a reporter protein GFP demonstrated widespread transduction of cells in the brain, cerebellum, meninges, spinal cord and dorsal root ganglia. Similar to the observations made in mice, GFP was also detected in the liver of Beagle dogs, where an average of 3.7% of hepatocytes was transduced. See Haurigot et al., supra. Importantly, the intra-CSF administration of AAV9 vectors encoding for the lysosomal enzyme sulfamidase, whose deficit causes MPSIIIA, led to sustained levels of enzyme in the CSF of treated dogs. The CSF bathes the CNS, making the enzyme available to different CNS structures. Indeed, the periodic delivery of recombinant enzyme to the CSF is a therapeutic strategy currently under clinical investigation for MPSIIIA. See NCT01155778 and NCT01299727, clinicaltrials.gov.

The same approach has been used to illustrate the potential efficacy of the AAV 9 vectors according to the present invention.

Figure 18:
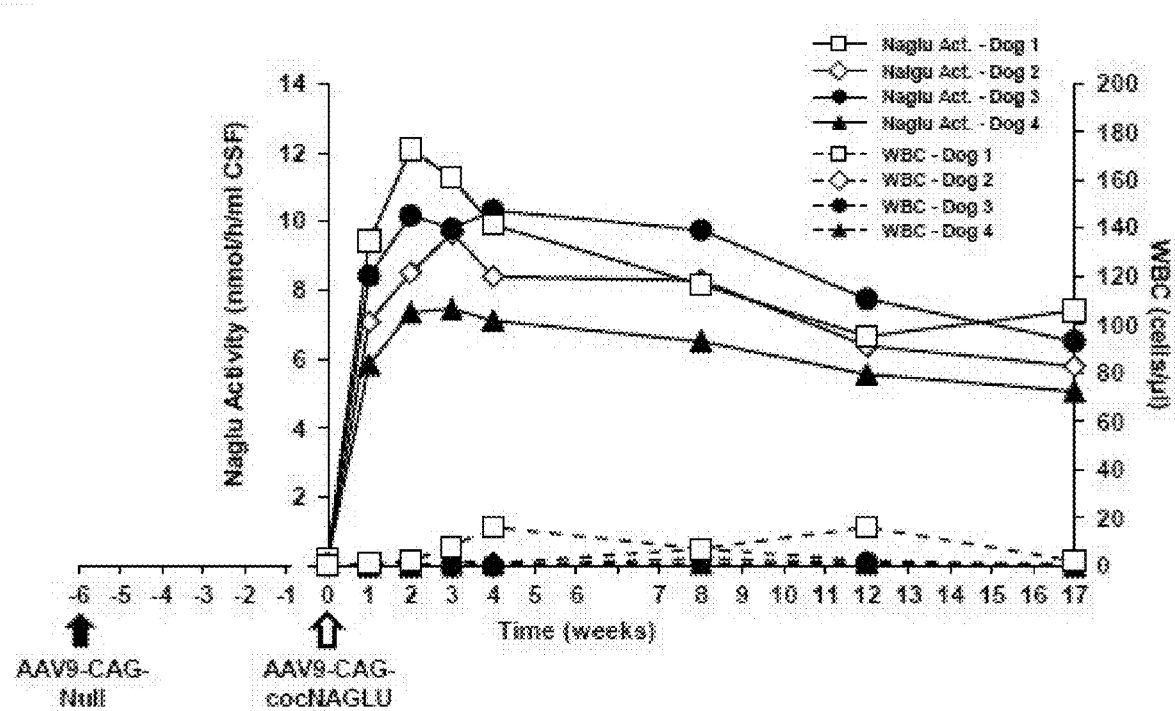
FIG. 18. Intracisternal delivery of AAV9 vectors coding for optimized canine N-acetylglucosaminidase, alpha (AAV9-CAG-cocNaglu) to Beagle dogs. (A) Follow up of anti-AAV9 Neutralising antibodies (Nab) titers in matched serum and CSF samples before and after intra-CSF delivery of AAV9-CAG-cocNaglu vectors to healthy Beagle dogs. Dogs 3 and 4 were pre-immunized by intravenous delivery of $1\times10^{11}$ vg/kg of AAV9-null vectors one month in advance of intracisternal administration. (B) Follow up of N-acetylglucosaminidase, alpha activity in the CSF of healthy adult Beagle dogs following intra-CSF administration of $6.5\times10^{12}$ vg of AAV9 vectors encoding for canine N-acetylglucosaminidase, alpha. Dogs 1 and 2 (open symbols) were naïve at the moment of administration whilst Dogs 3 and 4 (filled symbols) had pre-existing immunity against the AAV9 vector. The CSF white blood cell counts (WBC) for each time point for all dogs are depicted in the same graph (dashed lines).

A total dose of $6.5\times10^{12}$ vg AAV9-CAG-cocNaglu vectors was administered to the cisterna magna of 4 adult Beagle dogs (Dogs 1-4). To evaluate the impact of preexisting immunity on the CSF levels of N-acetylglucosaminidase, alpha activity that could be achieved by the treatment, two of those dogs (Dogs 3 and 4) were immunized by systemic administration of $1\times10^{11}$ vg/kg of non-coding AAV9-null vectors 6 weeks before CSF delivery. By the time the intracisternal administration of vectors was performed, naïve dogs had low titers of anti-AAV9 neutralizing antibodies (NAbs) in circulation and CSF, as it would be expected for animals that have not been previously exposed to the wild-type or recombinant virus. In contrast, pre-immunized dogs had high NAb titers in the circulation but low levels in the CSF, an observation compatible with the asymmetrical distribution of NAbs across the blood-brain barrier. See FIG. 18A and Haurigot et al., supra. The administration of AAV9-CAG-cocNaglu vectors to the cisterna magna led to a significant increase in the activity of the enzyme measured in the CSF samples from all 4 dogs, with no significant differences with respect to the presence or not of pre-exiting immunity. See FIG. 18B. Enzyme activity levels peaked between the $2^{nd}$ and $3^{rd}$ weeks and reached steady state levels thereafter. Importantly, this increase in the activity of N-acetylglucosaminidase, alpha in CSF was long-lasting (>4 months). See FIG. 18B.

The invention claimed is:

1. An isolated recombinant Adenoassociated Virus AAV9 vector comprising a CAG promoter comprising the nucleotide sequence as set forth in SEQ ID NO:4, wherein the CAG promoter is operably linked to a nucleic acid encoding N-acetylglucosaminidase, alpha, wherein the nucleic acid encoding N-acetylglucosaminidase, alpha comprises the nucleic acid sequence as set forth in SEQ ID NO:19.

2. A pharmaceutical composition comprising a therapeutically effective amount of the recombinant AAV9 vector of claim 1.

3. The pharmaceutical composition of claim 2 which is in a form for intravenous or intracisternal administration.

4. A method for increasing the N-acetylglucosaminidase, alpha activity in a subject having mucopolysaccharidosis type IIIB (MPS IIIB), the method comprising administering to the intra-cerebrospinal fluid (CSF) via intracisternal injection of a subject having mucopolysaccharidosis type IIIB disease, the recombinant AAV9 vector of claim 1, thereby increasing expression of the N-acetylglucosaminidase enzyme in the CSF as compared to a healthy subject.

5. An isolated cell comprising the recombinant Adenoassociated Virus AAV9 vector of claim 1.

6. An isolated recombinant Adenoassociated Virus AAV9 vector comprising a CAG promoter comprising the nucleotide sequence as set forth in SEQ ID NO:4, wherein the CAG promoter is operably linked to a nucleic acid encoding N-acetylglucosaminidase, alpha, wherein the nucleic acid encoding N-acetylglucosaminidase, alpha comprises the nucleic acid sequence as set forth in SEQ ID NO:22.

7. A pharmaceutical composition comprising a therapeutically effective amount of the recombinant AAV9 vector of claim 6.

8. The pharmaceutical composition of claim 7 which is in a form for intravenous or intracisternal administration.

9. A method for increasing the N-acetylglucosaminidase, alpha activity in a subject having mucopolysaccharidosis type IIIB (MPS IIIB), the method comprising administering to the intra-cerebrospinal fluid (CSF) via intracisternal injection of a subject having mucopolysaccharidosis type IIIB disease, the recombinant AAV9 vector of claim 6, thereby increasing expression of the N-acetylglucosaminidase enzyme in the CSF as compared to a healthy subject.

10. An isolated cell comprising the recombinant Adenoassociated Virus AAV9 vector according to claim 6.

11. A plasmid comprising a nucleic acid having the nucleotide sequence as set forth in SEQ ID NO: 19 which encodes N-acetylglucosaminidase, alpha comprising the amino acid sequence as set forth in SEQ ID NO: 1, wherein the plasmid is pAAV-CAG-cohNaglu-version2, deposited under the terms of the Budapest Treaty under accession number DSM 32042.

12. A pharmaceutical composition comprising a therapeutically effective amount of the plasmid of claim 11.

13. The pharmaceutical composition of claim 12 which is in a form for intravenous or intracisternal administration.

14. A plasmid comprising a nucleic acid having the nucleotide sequence as set forth in SEQ ID NO: 22 which encodes N-acetylglucosaminidase, alpha comprising the amino acid sequence as set forth in SEQ ID NO: 1, wherein the plasmid is pAAV-CAG-cohNaglu-version3, deposited under the terms of the Budapest Treaty under accession number DSM 32043.

15. A pharmaceutical composition comprising a therapeutically effective amount of the plasmid of claim 14.

16. The pharmaceutical composition of claim 15 which is in a form for intravenous or intracisternal administration.

* * * * *

SEQUENCE LISTING

```
<160> NUMBER OF SEQ ID NOS: 24

<210> SEQ ID NO 1
<211> LENGTH: 743
<212> TYPE: PRT
<213> ORGANISM: Homo sapiens

<400> SEQUENCE: 1

Met Glu Ala Val Ala Val Ala Ala Ala Val Gly Val Leu Leu Leu Ala
1               5                   10                  15

Gly Ala Gly Gly Ala Ala Gly Asp Glu Ala Arg Glu Ala Ala Ala Val
            20                  25                  30

Arg Ala Leu Val Ala Arg Leu Leu Gly Pro Gly Pro Ala Ala Asp Phe
        35                  40                  45

Ser Val Ser Val Glu Arg Ala Leu Ala Ala Lys Pro Gly Leu Asp Thr
    50                  55                  60

Tyr Ser Leu Gly Gly Gly Gly Ala Ala Arg Val Arg Val Arg Gly Ser
65                  70                  75                  80

Thr Gly Val Ala Ala Ala Ala Gly Leu His Arg Tyr Leu Arg Asp Phe
                85                  90                  95

Cys Gly Cys His Val Ala Trp Ser Gly Ser Gln Leu Arg Leu Pro Arg
            100                 105                 110

Pro Leu Pro Ala Val Pro Gly Glu Leu Thr Glu Ala Thr Pro Asn Arg
        115                 120                 125

Tyr Arg Tyr Tyr Gln Asn Val Cys Thr Gln Ser Tyr Ser Phe Val Trp
    130                 135                 140

Trp Asp Trp Ala Arg Trp Glu Arg Glu Ile Asp Trp Met Ala Leu Asn
145                 150                 155                 160

Gly Ile Asn Leu Ala Leu Ala Trp Ser Gly Gln Glu Ala Ile Trp Gln
                165                 170                 175

Arg Val Tyr Leu Ala Leu Gly Leu Thr Gln Ala Glu Ile Asn Glu Phe
            180                 185                 190

Phe Thr Gly Pro Ala Phe Leu Ala Trp Gly Arg Met Gly Asn Leu His
        195                 200                 205

Thr Trp Asp Gly Pro Leu Pro Pro Ser Trp His Ile Lys Gln Leu Tyr
    210                 215                 220
```

```
Leu Gln His Arg Val Leu Asp Gln Met Arg Ser Phe Gly Met Thr Pro
225                 230                 235                 240

Val Leu Pro Ala Phe Ala Gly His Val Pro Glu Ala Val Thr Arg Val
                245                 250                 255

Phe Pro Gln Val Asn Val Thr Lys Met Gly Ser Trp Gly His Phe Asn
            260                 265                 270

Cys Ser Tyr Ser Cys Ser Phe Leu Leu Ala Pro Glu Asp Pro Ile Phe
        275                 280                 285

Pro Ile Ile Gly Ser Leu Phe Leu Arg Glu Leu Ile Lys Glu Phe Gly
    290                 295                 300

Thr Asp His Ile Tyr Gly Ala Asp Thr Phe Asn Glu Met Gln Pro Pro
305                 310                 315                 320

Ser Ser Glu Pro Ser Tyr Leu Ala Ala Ala Thr Thr Ala Val Tyr Glu
                325                 330                 335

Ala Met Thr Ala Val Asp Thr Glu Ala Val Trp Leu Leu Gln Gly Trp
            340                 345                 350

Leu Phe Gln His Gln Pro Gln Phe Trp Gly Pro Ala Gln Ile Arg Ala
        355                 360                 365

Val Leu Gly Ala Val Pro Arg Gly Arg Leu Leu Val Leu Asp Leu Phe
    370                 375                 380

Ala Glu Ser Gln Pro Val Tyr Thr Arg Thr Ala Ser Phe Gln Gly Gln
385                 390                 395                 400

Pro Phe Ile Trp Cys Met Leu His Asn Phe Gly Gly Asn His Gly Leu
                405                 410                 415

Phe Gly Ala Leu Glu Ala Val Asn Gly Gly Pro Glu Ala Ala Arg Leu
            420                 425                 430

Phe Pro Asn Ser Thr Met Val Gly Thr Gly Met Ala Pro Glu Gly Ile
        435                 440                 445

Ser Gln Asn Glu Val Val Tyr Ser Leu Met Ala Glu Leu Gly Trp Arg
    450                 455                 460

Lys Asp Pro Val Pro Asp Leu Ala Ala Trp Val Thr Ser Phe Ala Ala
465                 470                 475                 480

Arg Arg Tyr Gly Val Ser His Pro Asp Ala Gly Ala Ala Trp Arg Leu
                485                 490                 495

Leu Leu Arg Ser Val Tyr Asn Cys Ser Gly Glu Ala Cys Arg Gly His
            500                 505                 510

Asn Arg Ser Pro Leu Val Arg Arg Pro Ser Leu Gln Met Asn Thr Ser
        515                 520                 525

Ile Trp Tyr Asn Arg Ser Asp Val Phe Glu Ala Trp Arg Leu Leu Leu
    530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Leu Pro Ala Leu Asp Glu
        595                 600                 605

Val Leu Ala Ser Asp Ser Arg Phe Leu Leu Gly Ser Trp Leu Glu Gln
    610                 615                 620

Ala Arg Ala Ala Ala Val Ser Glu Ala Glu Ala Asp Phe Tyr Glu Gln
625                 630                 635                 640
```

```
Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
            660                 665                 670

Pro Arg Trp Arg Leu Phe Leu Glu Ala Leu Val Asp Ser Val Ala Gln
        675                 680                 685

Gly Ile Pro Phe Gln Gln His Gln Phe Asp Lys Asn Val Phe Gln Leu
    690                 695                 700

Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
                725                 730                 735

Arg Trp Val Ala Gly Ser Trp
            740


<210> SEQ ID NO 2
<211> LENGTH: 2232
<212> TYPE: DNA
<213> ORGANISM: Homo sapiens

<400> SEQUENCE: 2

atggaggcgg tggcggtggc cgcggcggtg ggggtccttc tcctggccgg ggccgggggc      60

gcggcaggcg acgaggcccg ggaggcggcg gccgtgcggg cgctcgtggc ccggctgctg     120

gggccaggcc ccgcggccga cttctccgtg tcggtggagc gcgctctggc tgccaagccg     180

ggcttggaca cctacagcct gggcggcggc ggcgcggcgc gcgtgcgggt gcgcggctcc     240

acgggcgtgg cggccgccgc ggggctgcac cgctacctgc gcgacttctg tggctgccac     300

gtggcctggt ccggctctca gctgcgcctg ccgcggccac tgccagccgt gccgggggag     360

ctgaccgagg ccacgcccaa caggtaccgc tattaccaga atgtgtgcac gcaaagctac     420

tctttcgtgt ggtgggactg ggcccgctgg gagcgagaga tagactggat ggcgctgaat     480

ggcatcaacc tggcactggc ctggagcggc caggaggcca tctggcagcg ggtgtacctg     540

gccttgggcc tgacccaggc agagatcaat gagttcttta ctggtcctgc cttcctggcc     600

tgggggcgaa tgggcaacct gcacacctgg gatggccccc tgccccccctc ctggcacatc     660

aagcagcttt acctgcagca ccgggtcctg gaccagatgc gctccttcgg catgacccca     720

gtgctgcctg cattcgcggg gcatgttccc gaggctgtca ccagggtgtt ccctcaggtc     780

aatgtcacga agatgggcag ttggggccac tttaactgtt cctactcctg ctccttcctt     840

ctggctccgg aagaccccat attccccatc atcgggagcc tcttcctgcg agagctgatc     900

aaagagtttg gcacagacca catctatggg gccgacactt tcaatgagat gcagccacct     960

tcctcagagc cctcctacct tgccgcagcc accactgccg tctatgaggc catgactgca    1020

gtggatactg aggctgtgtg gctgctccaa ggctggctct tccagcacca gccgcagttc    1080

tgggggcccg cccagatcag ggctgtgctg ggagctgtgc cccgtggccg cctcctggtt    1140

ctggacctgt ttgctgagag ccagcctgtg tatacccgca ctgcctcctt ccagggccag    1200

cccttcatct ggtgcatgct gcacaacttt gggggaaacc atggtctttt tggagcccta    1260

gaggctgtga acggaggccc agaagctgcc cgcctcttcc ccaactccac catggtaggc    1320

acgggcatgg cccccgaggg catcagccag aacgaagtgg tctattccct catggctgag    1380

ctgggctggc gaaaggaccc agtgccagat ttggcagcct gggtgaccag ctttgccgcc    1440

cggcggtatg ggtctcccca cccggacgca ggggcagcgt ggaggctact gctccggagt    1500
```

```
gtgtacaact gctccgggga ggcctgcagg ggccacaatc gtagcccgct ggtcaggcgg   1560

ccgtccctac agatgaatac cagcatctgg tacaaccgat ctgatgtgtt tgaggcctgg   1620

cggctgctgc tcacatctgc tccctccctg gccaccagcc ccgccttccg ctacgacctg   1680

ctggacctca ctcggcaggc agtgcaggag ctggtcagct tgtactatga ggaggcaaga   1740

agcgcctacc tgagcaagga gctggcctcc ctgttgaggg ctggaggcgt cctggcctat   1800

gagctgctgc cggcactgga cgaggtgctg gctagtgaca gccgcttctt gctgggcagc   1860

tggctagagc aggcccgagc agcggcagtc agtgaggccg aggccgattt ctacgagcag   1920

aacagccgct accagctgac cttgtggggg ccagaaggca acatcctgga ctatgccaac   1980

aagcagctgg cggggttggt ggccaactac tacacccctc gctggcggct tttcctggag   2040

gcgctggttg acagtgtggc ccagggcatc cctttccaac agcaccagtt tgacaaaaat   2100

gtcttccaac tggagcaggc cttcgttctc agcaagcaga ggtaccccag ccagccgcga   2160

ggagacactg tggacctggc caagaagatc ttcctcaaat attacccccg ctgggtggcc   2220

ggctcttggt ga                                                       2232
```

<210> SEQ ID NO 3
<211> LENGTH: 2232
<212> TYPE: DNA
<213> ORGANISM: Artificial Sequence
<220> FEATURE:
<223> OTHER INFORMATION: cohNaGlu nucleotide sequence

<400> SEQUENCE: 3

```
atggaagctg tggctgtggc agctgctgtg ggcgtgctgc tgctggcagg cgctggcgga     60

gctgctgggg atgaagctag agaagctgcc gctgtgcggg ccctggtggc tagactgctg    120

ggacctggac ctgccgccga cttctccgtg tctgtggaaa gagccctggc cgccaagcct    180

ggcctggaca catattctct gggcggaggc ggcgctgctc gcgtcagagt gcgaggatct    240

acaggcgtgg ccgctgctgc cggactgcac agatacctga gagacttctg cggctgccat    300

gtggcttgga gcggcagcca gctgagactg cctagacctc tgcctgctgt gcctggcgag    360

ctgacagagg ccacccctaa cagataccgg tactaccaga acgtgtgcac ccagagctac    420

agcttcgtgt ggtgggactg ggccagatgg gagcgcgaga tcgattggat ggccctgaac    480

ggcatcaacc tggccctggc ttggagtggc caggaagcca tctggcagag agtgtacctg    540

gctctgggcc tgacccaggc cgagatcaac gagttcttta ccggccctgc ctttctggcc    600

tggggcagaa tgggcaacct gcacacatgg gacggccccc tgcctcctag ctggcacatc    660

aagcagctgt acctgcagca cagagtgctg gaccagatga gaagcttcgg catgaccccc    720

gtgctgcctg cttttgctgg acacgtgcca gaggccgtga ccagagtgtt cccccaagtg    780

aacgtgacca agatgggcag ctggggccac ttcaactgca gctactcctg cagcttcctg    840

ctggcccccg aggaccccat cttccctatt atcggcagcc tgttcctgcg ggaactgatc    900

aaagagttcg gcaccgacca catctacggc gccgacacct tcaacgagat gcagcccccct    960

agcagcgagc cctcttacct ggctgctgcc accacagccg tgtacgaggc catgacagcc   1020

gtggataccg aggccgtgtg gctgctgcag ggatggctgt ttcagcacca gccccagttc   1080

tggggccctg cccagattag agcagtgctg ggcgctgtgc ccagaggcag gctgctggtg   1140

ctggatctgt tcgccgagag ccagcccgtg tacaccagaa ccgctagctt ccagggacag   1200

cccttcatct ggtgcatgct gcacaacttc ggcggcaacc acggcctgtt cggcgctctg   1260

gaagcagtga atggcggccc tgaggccgcc agactgttcc ctaacagcac aatggtggga   1320
```

```
accggcatgg cccctgaggg catctctcag aacgaggtgg tgtacagcct gatggccgag   1380
ctgggctggc ggaaggatcc tgtgcctgat ctggccgcct gggtcacaag cttcgccgct   1440
agaagatacg gcgtgtccca ccctgatgct ggcgccgctt ggagactgct gctgagaagc   1500
gtgtacaact gctccggcga ggcctgcagg ggccacaaca gatctccact cgtgcggagg   1560
cccagcctgc agatgaacac cagcatctgg tacaatcgga gcgacgtgtt cgaggcctgg   1620
cgcctgctgc tgacatctgc tcctagcctg gccacctccc ccgccttcag atacgatctg   1680
ctggacctga ccaggcaggc cgtgcaggaa ctggtgtccc tgtactacga ggaagccaga   1740
agcgcctacc tgagcaaaga gctggcctcc ctgctgagag caggggggagt gctggcttac   1800
gaactgctgc cagccctgga tgaggtgctg gctagcgact ccagatttct gctgggctcc   1860
tggctggaac aggccagagc tgccgcagtg tctgaggccg aggccgattt ctacgagcag   1920
aacagcagat accagctgac cctgtggggc ccagagggca acatcctgga ctacgccaac   1980
aaacagctgg ccggcctggt ggccaactac tacacaccta gatggcggct gtttctggaa   2040
gctctggtgg actctgtggc ccagggcatc ccattccagc agcaccagtt cgacaagaac   2100
gtgttccagc tggaacaggc tttcgtgctg agcaagcaga gataccccag ccagcctaga   2160
ggcgacacag tggacctggc caagaagatc tttctgaagt actaccccag atgggtggcc   2220
ggctcttggt ga                                                        2232
```

<210> SEQ ID NO 4
<211> LENGTH: 646
<212> TYPE: DNA
<213> ORGANISM: Artificial Sequence
<220> FEATURE:
<223> OTHER INFORMATION: CAG nucleotide sequence

<400> SEQUENCE: 4

```
actagttatt aatagtaatc aattacgggg tcattagttc atagcccata tatggagttc     60
cgcgttacat aacttacggt aaatggcccg cctggctgac cgcccaacga cccccgccca    120
ttgacgtcaa taatgacgta tgttcccata gtaacgccaa tagggacttt ccattgacgt    180
caatgggtgg agtatttacg gtaaactgcc cacttggcag tacatcaagt gtatcatatg    240
ccaagtacgc cccctattga cgtcaatgac ggtaaatggc ccgcctggca ttatgcccag    300
tacatgacct tatgggactt tcctacttgg cagtacatct acgtattagt catcgctatt    360
accatggtcg aggtgagccc cacgttctgc ttcactctcc ccatctcccc cccctcccca    420
cccccaattt tgtatttatt tatttttttaa ttattttgtg cagcgatggg ggcggggggg    480
gggggggggc gcgcgccagg cggggcgggg cggggcgagg ggcggggcgg ggcgaggcgg    540
agaggtgcgg cggcagccaa tcagagcggc gcgctccgaa agtttccttt tatggcgagg    600
cggcggcggc ggcggcccta taaaaagcga agcgcgcggc gggcgg                   646
```

<210> SEQ ID NO 5
<211> LENGTH: 8461
<212> TYPE: DNA
<213> ORGANISM: Artificial Sequence
<220> FEATURE:
<223> OTHER INFORMATION: pAAV-CAG-hNaGlu Nucleotide sequence

<400> SEQUENCE: 5

```
attacgccag ctgcgcgctc gctcgctcac tgaggccgcc cgggcaaagc ccgggcgtcg     60
ggcgaccttt ggtcgcccgg cctcagtgag cgagcgagcg cgcagagagg gagtggccaa    120
```

```
ctccatcact aggggttcct tgtagttaat gattaacccg ccatgctact tatctactcg    180
acattgatta ttgactagtt attaatagta atcaattacg gggtcattag ttcatagccc    240
atatatggag ttccgcgtta cataacttac ggtaaatggc ccgcctggct gaccgcccaa    300
cgacccccgc ccattgacgt caataatgac gtatgttccc atagtaacgc caatagggac    360
tttccattga cgtcaatggg tggagtattt acggtaaact gcccacttgg cagtacatca    420
agtgtatcat atgccaagta cgccccctat tgacgtcaat gacggtaaat ggcccgcctg    480
gcattatgcc cagtacatga ccttatggga ctttcctact tggcagtaca tctacgtatt    540
agtcatcgct attaccatgg tcgaggtgag ccccacgttc tgcttcactc tccccatctc    600
ccccccctcc ccacccccaa ttttgtattt atttattttt taattatttt gtgcagcgat    660
gggggcgggg gggggggggg ggcgcgcgcc aggcggggcg gggcggggcg aggggcgggg    720
cggggcgagg cggagaggtg cggcggcagc caatcagagc ggcgcgctcc gaaagtttcc    780
ttttatggcg aggcggcggc ggcggcggcc ctataaaaag cgaagcgcgc ggcgggcggg    840
agtcgctgcg ttgccttcgc cccgtgcccc gctccgccgc cgcctcgcgc cgcccgcccc    900
ggctctgact gaccgcgtta ctcccacagg tgagcgggcg ggacggccct tctcctccgg    960
gctgtaatta gcgcttggtt taatgacggc ttgtttcttt tctgtggctg cgtgaaagcc   1020
ttgaggggct ccgggagggc cctttgtgcg gggggagcgg ctcggggggt gcgtgcgtgt   1080
gtgtgtgcgt ggggagcgcc gcgtgcggct ccgcgctgcc cggcggctgt gagcgctgcg   1140
ggcgcggcgc ggggctttgt gcgctccgca gtgtgcgcga ggggagcgcg gccgggggcg   1200
gtgccccgcg gtgcgggggg ggctgcgagg ggaacaaagg ctgcgtgcgg ggtgtgtgcg   1260
tgggggggtg agcagggggt gtgggcgcgt cggtcgggct gcaacccccc ctgcaccccc   1320
ctccccgagt tgctgagcac ggcccggctt cgggtgcggg gctccgtacg gggcgtggcg   1380
cggggctcgc cgtgccgggc ggggggtggc ggcaggtggg ggtgccgggc ggggcggggc   1440
cgcctcgggc cggggagggc tcgggggagg ggcgcggcgg cccccggagc gccggcggct   1500
gtcgaggcgc ggcgagccgc agccattgcc ttttatggta atcgtgcgag agggcgcagg   1560
gacttccttt gtcccaaatc tgtgcggagc cgaaatctgg gaggcgccgc cgcaccccct   1620
ctagcgggcg cggggcgaag cggtgcggcg ccggcaggaa ggaaatgggc ggggagggcc   1680
ttcgtgcgtc gccgcgccgc cgtccccttc tccctctcca gcctcggggc tgtccgcggg   1740
gggacggctg ccttcggggg ggacggggca gggcggggtt cggcttctgg cgtgtgaccg   1800
gcggctctag agcctctgct aaccatgttc atgccttctt ctttttccta cagctcctgg   1860
gcaacgtgct ggttattgtg ctgtctcatc attttggcaa agaattgatt aattcgagcg   1920
aacgcgtatg gaggcggtgg cggtggccgc ggcggtgggg gtccttctcc tggccggggc   1980
cgggggcgcg gcaggcgacg aggcccggga ggcggcggcc gtgcgggcgc tcgtggcccg   2040
gctgctgggg ccaggccccg cggccgactt ctccgtgtcg gtggagcgcg ctctggctgc   2100
caagccgggc ttggacacct acagcctggg cggcggcggc gcggcgcgcg tgcgggtgcg   2160
cggctccacg ggcgtggcgg ccgccgcggg gctgcaccgc tacctgcgcg acttctgtgg   2220
ctgccacgtg gcctggtccg gctctcagct gcgcctgccg cggccactgc cagccgtgcc   2280
gggggagctg accgaggcca cgcccaacag gtaccgctat taccagaatg tgtgcacgca   2340
aagctactct ttcgtgtggt gggactgggc ccgctgggag cgagagatag actggatggc   2400
gctgaatggc atcaacctgg cactggcctg gagcggccag gaggccatct ggcagcgggt   2460
gtacctggcc ttgggcctga cccaggcaga gatcaatgag ttctttactg gtcctgcctt   2520
```

```
cctggcctgg gggcgaatgg gcaacctgca cacctgggat ggccccctgc ccccctcctg   2580
gcacatcaag cagctttacc tgcagcaccg ggtcctggac cagatgcgct ccttcggcat   2640
gaccccagtg ctgcctgcat tcgcggggca tgttcccgag gctgtcacca gggtgttccc   2700
tcaggtcaat gtcacgaaga tgggcagttg ggccactttt aactgttcct actcctgctc   2760
cttccttctg gctccggaag accccatatt ccccatcatc gggagcctct tcctgcgaga   2820
gctgatcaaa gagtttggca cagaccacat ctatggggcc gacactttca atgagatgca   2880
gccaccttcc tcagagccct cctaccttgc cgcagccacc actgccgtct atgaggccat   2940
gactgcagtg gatactgagg ctgtgtggct gctccaaggc tggctcttcc agcaccagcc   3000
gcagttctgg gggcccgccc agatcagggc tgtgctggga gctgtgcccc gtggccgcct   3060
cctggttctg gacctgtttg ctgagagcca gcctgtgtat acccgcactg cctccttcca   3120
gggccagccc ttcatctggt gcatgctgca caactttggg ggaaaccatg gtctttttgg   3180
agccctagag gctgtgaacg gaggcccaga agctgcccgc ctcttcccca actccaccat   3240
ggtaggcacg ggcatggccc ccgagggcat cagccagaac gaagtggtct attccctcat   3300
ggctgagctg ggctggcgaa aggacccagt gccagatttg gcagcctggg tgaccagctt   3360
tgccgcccgg cggtatgggg tctcccaccc ggacgcaggg gcagcgtgga ggctactgct   3420
ccggagtgtg tacaactgct ccggggaggc ctgcaggggc cacaatcgta gcccgctggt   3480
caggcggccg tccctacaga tgaataccag catctggtac aaccgatctg atgtgtttga   3540
ggcctggcgg ctgctgctca catctgctcc ctccctggcc accagccccg ccttccgcta   3600
cgacctgctg gacctcactc ggcaggcagt gcaggagctg gtcagcttgt actatgagga   3660
ggcaagaagc gcctacctga gcaaggagct ggcctccctg ttgagggctg gaggcgtcct   3720
ggcctatgag ctgctgccgg cactggacga ggtgctggct agtgacagcc gcttcttgct   3780
gggcagctgg ctagagcagg cccgagcagc ggcagtcagt gaggccgagg ccgatttcta   3840
cgagcagaac agccgctacc agctgacctt gtgggggcca gaaggcaaca tcctggacta   3900
tgccaacaag cagctggcgg ggttggtggc caactactac acccctcgct ggcggctttt   3960
cctggaggcg ctggttgaca gtgtggccca gggcatccct ttccaacagc accagtttga   4020
caaaaatgtc ttccaactgg agcaggcctt cgttctcagc aagcagaggt accccagcca   4080
gccgcgagga gacactgtgg acctggccaa gaagatcttc ctcaaatatt acccccgctg   4140
ggtggccggc tcttggtgag aattcgagct cggtacccgg gaatcaattc actcctcagg   4200
tgcaggctgc ctatcagaag gtggtggctg gtgtggccaa tgccctggct cacaaatacc   4260
actgagatct tttccctct gccaaaaatt atggggacat catgaagccc cttgagcatc   4320
tgacttctgg ctaataaagg aaatttattt tcattgcaat agtgtgttgg aatttttgt   4380
gtctctcact cggaaggaca tatgggaggg caaatcattt aaaacatcag aatgagtatt   4440
tggtttagag tttggcaaca tatgcccata tgctggctgc catgaacaaa ggttggctat   4500
aaagaggtca tcagtatatg aaacagcccc ctgctgtcca ttccttattc catagaaaag   4560
ccttgacttg aggttagatt ttttttatat tttgttttgt gttatttttt tctttaacat   4620
ccctaaaatt ttccttacat gttttactag ccagattttt cctcctctcc tgactactcc   4680
cagtcatagc tgtccctctt ctcttatgga gatccctcga cctgcagccc aagctgtaga   4740
taagtagcat ggcgggttaa tcattaacta caaggaaccc ctagtgatgg agttggccac   4800
tccctctctg cgcgctcgct cgctcactga ggccgcccgg gctttgcccg ggcggcctca   4860
```

```
gtgagcgagc gagcgcgcag ctgcattaat gaatcggcca acgcgcgggg agaggcggtt   4920
tgcgtattgg gcgctcttcc gcttcctcgc tcactgactc gctgcgctcg gtcgttcggc   4980
tgcggcgagc ggtatcagct cactcaaagg cggtaatacg gttatccaca gaatcagggg   5040
ataacgcagg aaagaacatg tgagcaaaag gccagcaaaa ggccaggaac cgtaaaaagg   5100
ccgcgttgct ggcgtttttc cataggctcc gcccccctga cgagcatcac aaaaatcgac   5160
gctcaagtca gaggtggcga aacccgacag gactataaag ataccaggcg tttccccctg   5220
gaagctccct cgtgcgctct cctgttccga ccctgccgct taccggatac ctgtccgcct   5280
ttctcccttc gggaagcgtg gcgctttctc atagctcacg ctgtaggtat ctcagttcgg   5340
tgtaggtcgt tcgctccaag ctgggctgtg tgcacgaacc ccccgttcag cccgaccgct   5400
gcgccttatc cggtaactat cgtcttgagt ccaacccggt aagacacgac ttatcgccac   5460
tggcagcagc cactggtaac aggattagca gagcgaggta tgtaggcggt gctacagagt   5520
tcttgaagtg gtggcctaac tacggctaca ctagaagaac agtatttggt atctgcgctc   5580
tgctgaagcc agttaccttc ggaaaaagag ttggtagctc ttgatccggc aaacaaacca   5640
ccgctggtag cggtggtttt tttgtttgca agcagcagat tacgcgcaga aaaaaaggat   5700
ctcaagaaga tcctttgatc ttttctacgg ggtctgacgc tcagtggaac gaaaactcac   5760
gttaagggat tttggtcatg agattatcaa aaaggatctt cacctagatc cttttaaatt   5820
aaaaatgaag ttttaaatca atctaaagta tatatgagta aacttggtct gacagttacc   5880
aatgcttaat cagtgaggca cctatctcag cgatctgtct atttcgttca tccatagttg   5940
cctgactccc cgtcgtgtag ataactacga tacgggaggg cttaccatct ggccccagtg   6000
ctgcaatgat accgcgagac ccacgctcac cggctccaga tttatcagca ataaaccagc   6060
cagccggaag ggccgagcgc agaagtggtc ctgcaacttt atccgcctcc atccagtcta   6120
ttaattgttg ccgggaagct agagtaagta gttcgccagt taatagtttg cgcaacgttg   6180
ttgccattgc tacaggcatc gtggtgtcac gctcgtcgtt tggtatggct tcattcagct   6240
ccggttccca acgatcaagg cgagttacat gatcccccat gttgtgcaaa aaagcggtta   6300
gctccttcgg tcctccgatc gttgtcagaa gtaagttggc cgcagtgtta tcactcatgg   6360
ttatggcagc actgcataat tctcttactg tcatgccatc cgtaagatgc ttttctgtga   6420
ctggtgagta ctcaaccaag tcattctgag aatagtgtat gcggcgaccg agttgctctt   6480
gcccggcgtc aatacgggat aataccgcgc cacatagcag aactttaaaa gtgctcatca   6540
ttggaaaacg ttcttcgggg cgaaaactct caaggatctt accgctgttg agatccagtt   6600
cgatgtaacc cactcgtgca cccaactgat cttcagcatc ttttactttc accagcgttt   6660
ctgggtgagc aaaaacagga aggcaaaatg ccgcaaaaaa gggaataagg gcgacacgga   6720
aatgttgaat actcatactc ttcctttttc aatattattg aagcatttat cagggttatt   6780
gtctcatgag cggatacata tttgaatgta tttagaaaaa taaacaaata ggggttccgc   6840
gcacatttcc ccgaaaagtg ccacctgacg tctaagaaac cattattatc atgacattaa   6900
cctataaaaa taggcgtatc acgaggccct ttcgtctcgc gcgtttcggt gatgacggtg   6960
aaaacctctg acacatgcag ctcccggaga cggtcacagc ttgtctgtaa gcggatgccg   7020
ggagcagaca agcccgtcag ggcgcgtcag cgggtgttgg cgggtgtcgg ggctggctta   7080
actatgcggc atcagagcag attgtactga gagtgcacca tatgcggtgt gaaataccgc   7140
acagatgcgt aaggagaaaa taccgcatca ggcgattcca acatccaata aatcatacag   7200
gcaaggcaaa gaattagcaa aattaagcaa taaagcctca gagcataaag ctaaatcggt   7260
```

```
tgtaccaaaa acattatgac cctgtaatac ttttgcggga gaagccttta tttcaacgca   7320

aggataaaaa tttttagaac cctcatatat tttaaatgca atgcctgagt aatgtgtagg   7380

taaagattca aacgggtgag aaaggccgga gacagtcaaa tcaccatcaa tatgatattc   7440

aaccgttcta gctgataaat tcatgccgga gagggtagct atttttgaga ggtctctaca   7500

aaggctatca ggtcattgcc tgagagtctg gagcaaacaa gagaatcgat gaacggtaat   7560

cgtaaaacta gcatgtcaat catatgtacc ccggttgata atcagaaaag ccccaaaaac   7620

aggaagattg tataagcaaa tatttaaatt gtaagcgtta atattttgtt aaaattcgcg   7680

ttaaattttt gttaaatcag ctcatttttt aaccaatagg ccgaaatcgg caaaatccct   7740

tataaatcaa aagaatagac cgagataggg ttgagtgttg ttccagtttg gaacaagagt   7800

ccactattaa agaacgtgga ctccaacgtc aaagggcgaa aaaccgtcta tcagggcgat   7860

ggcccactac gtgaaccatc accctaatca agttttttgg ggtcgaggtg ccgtaaagca   7920

ctaaatcgga accctaaagg gagcccccga tttagagctt gacggggaaa gccggcgaac   7980

gtggcgagaa aggaagggaa gaaagcgaaa ggagcgggcg ctagggcgct ggcaagtgta   8040

gcggtcacgc tgcgcgtaac caccacaccc gccgcgctta atgcgccgct acagggcgcg   8100

tactatggtt gctttgacga gcacgtataa cgtgctttcc tcgttagaat cagagcggga   8160

gctaaacagg aggccgatta aagggatttt agacaggaac ggtacgccag aatcctgaga   8220

agtgttttta taatcagtga ggccaccgag taaaagagtc tgtccatcac gcaaattaac   8280

cgttgtcgca atacttcttt gattagtaat aacatcactt gcctgagtag aagaactcaa   8340

actatcggcc ttgctggtaa tatccagaac aatattaccg ccagccattg caacggaatc   8400

gccattcgcc attcaggctg cgcaactgtt gggaagggcg atcggtgcgg gcctcttcgc   8460

t                                                                   8461
```

```
<210> SEQ ID NO 6
<211> LENGTH: 8467
<212> TYPE: DNA
<213> ORGANISM: Artificial Sequence
<220> FEATURE:
<223> OTHER INFORMATION: pAAV-CAG-cohNaGlu Nucleotide sequence

<400> SEQUENCE: 6
```

```
attacgccag ctgcgcgctc gctcgctcac tgaggccgcc cgggcaaagc ccgggcgtcg     60

ggcgaccttt ggtcgcccgg cctcagtgag cgagcgagcg cgcagagagg gagtggccaa    120

ctccatcact aggggttcct tgtagttaat gattaacccg ccatgctact tatctactcg    180

acattgatta ttgactagtt attaatagta atcaattacg gggtcattag ttcatagccc    240

atatatggag ttccgcgtta cataacttac ggtaaatggc ccgcctggct gaccgcccaa    300

cgacccccgc ccattgacgt caataatgac gtatgttccc atagtaacgc caatagggac    360

tttccattga cgtcaatggg tggagtattt acggtaaact gcccacttgg cagtacatca    420

agtgtatcat atgccaagta cgccccctat tgacgtcaat gacggtaaat ggcccgcctg    480

gcattatgcc cagtacatga ccttatggga ctttcctact tggcagtaca tctacgtatt    540

agtcatcgct attaccatgg tcgaggtgag ccccacgttc tgcttcactc tccccatctc    600

ccccccctcc ccacccccaa ttttgtattt atttattttt taattatttt gtgcagcgat    660

gggggcgggg gggggggggg ggcgcgcgcc aggcggggcg gggcggggcg aggggcgggg    720

cggggcgagg cggagaggtg cggcggcagc caatcagagc ggcgcgctcc gaaagtttcc    780
```

```
ttttatggcg aggcggcggc ggcggcggcc ctataaaaag cgaagcgcgc ggcgggcggg    840
agtcgctgcg ttgccttcgc cccgtgcccc gctccgccgc cgcctcgcgc cgcccgcccc    900
ggctctgact gaccgcgtta ctcccacagg tgagcgggcg ggacggccct tctcctccgg    960
gctgtaatta gcgcttggtt taatgacggc ttgtttcttt tctgtggctg cgtgaaagcc   1020
ttgaggggct ccgggagggc cctttgtgcg gggggagcgg ctcggggggt gcgtgcgtgt   1080
gtgtgtgcgt ggggagcgcc gcgtgcggct ccgcgctgcc cggcggctgt gagcgctgcg   1140
ggcgcggcgc ggggctttgt gcgctccgca gtgtgcgcga ggggagcgcg gccgggggcg   1200
gtgccccgcg gtgcgggggg ggctgcgagg ggaacaaagg ctgcgtgcgg ggtgtgtgcg   1260
tgggggggtg agcagggggt gtgggcgcgt cggtcgggct gcaacccccc ctgcaccccc   1320
ctccccgagt tgctgagcac ggcccggctt cgggtgcggg gctccgtacg gggcgtggcg   1380
cggggctcgc cgtgccgggc ggggggtggc ggcaggtggg ggtgccgggc ggggcggggc   1440
cgcctcgggc cggggagggc tcgggggagg ggcgcggcgg cccccggagc gccggcggct   1500
gtcgaggcgc ggcgagccgc agccattgcc ttttatggta atcgtgcgag agggcgcagg   1560
gacttccttt gtcccaaatc tgtgcggagc cgaaatctgg gaggcgccgc cgcaccccct   1620
ctagcgggcg cggggcgaag cggtgcggcg ccggcaggaa ggaaatgggc ggggagggcc   1680
ttcgtgcgtc gccgcgccgc cgtccccttc tccctctcca gcctcggggc tgtccgcggg   1740
gggacggctg ccttcggggg ggacggggca gggcggggtt cggcttctgg cgtgtgaccg   1800
gcggctctag agcctctgct aaccatgttc atgccttctt ctttttccta cagctcctgg   1860
gcaacgtgct ggttattgtg ctgtctcatc attttggcaa agaattgatt aattcgagcg   1920
aacgcgtgcc accatggaag ctgtggctgt ggcagctgct gtgggcgtgc tgctgctggc   1980
aggcgctggc ggagctgctg gggatgaagc tagagaagct gccgctgtgc gggccctggt   2040
ggctagactg ctgggacctg gacctgccgc cgacttctcc gtgtctgtgg aaagagccct   2100
ggccgccaag cctggcctgg acacatattc tctgggcgga ggcggcgctg ctcgcgtcag   2160
agtgcgagga tctacaggcg tggccgctgc tgccggactg cacagatacc tgagagactt   2220
ctgcggctgc catgtggctt ggagcggcag ccagctgaga ctgcctagac ctctgcctgc   2280
tgtgcctggc gagctgacag aggccacccc taacagatac cggtactacc agaacgtgtg   2340
cacccagagc tacagcttcg tgtggtggga ctgggccaga tgggagcgcg agatcgattg   2400
gatggccctg aacggcatca acctggccct ggcttggagt ggccaggaag ccatctggca   2460
gagagtgtac ctggctctgg gcctgaccca ggccgagatc aacgagttct ttaccggccc   2520
tgcctttctg gcctggggca gaatgggcaa cctgcacaca tgggacggcc ccctgcctcc   2580
tagctggcac atcaagcagc tgtacctgca gcacagagtg ctggaccaga tgagaagctt   2640
cggcatgacc cccgtgctgc ctgcttttgc tggacacgtg ccagaggccg tgaccagagt   2700
gttcccccaa gtgaacgtga ccaagatggg cagctggggc cacttcaact gcagctactc   2760
ctgcagcttc ctgctggccc ccgaggaccc catcttccct attatcggca gcctgttcct   2820
gcgggaactg atcaaagagt tcggcaccga ccacatctac ggcgccgaca ccttcaacga   2880
gatgcagccc cctagcagcg agccctctta cctggctgct gccaccacag ccgtgtacga   2940
ggccatgaca gccgtggata ccgaggccgt gtggctgctg cagggatggc tgtttcagca   3000
ccagccccag ttctggggcc ctgcccagat tagagcagtg ctgggcgctg tgcccagagg   3060
caggctgctg gtgctggatc tgttcgccga gagccagccc gtgtacacca gaaccgctag   3120
cttccaggga cagcccttca tctggtgcat gctgcacaac ttcggcggca accacggcct   3180
```

```
gttcggcgct ctggaagcag tgaatggcgg ccctgaggcc gccagactgt tccctaacag   3240
cacaatggtg ggaaccggca tggcccctga gggcatctct cagaacgagg tggtgtacag   3300
cctgatggcc gagctgggct ggcggaagga tcctgtgcct gatctggccg cctgggtcac   3360
aagcttcgcc gctagaagat acggcgtgtc ccaccctgat gctggcgccg cttggagact   3420
gctgctgaga agcgtgtaca actgctccgg cgaggcctgc aggggccaca acagatctcc   3480
actcgtgcgg aggcccagcc tgcagatgaa caccagcatc tggtacaatc ggagcgacgt   3540
gttcgaggcc tggcgcctgc tgctgacatc tgctcctagc ctggccacct cccccgcctt   3600
cagatacgat ctgctggacc tgaccaggca ggccgtgcag gaactggtgt ccctgtacta   3660
cgaggaagcc agaagcgcct acctgagcaa agagctggcc tccctgctga gagcaggggg   3720
agtgctggct tacgaactgc tgccagccct ggatgaggtg ctggctagcg actccagatt   3780
tctgctgggc tcctggctgg aacaggccag agctgccgca gtgtctgagg ccgaggccga   3840
tttctacgag cagaacagca gataccagct gaccctgtgg ggcccagagg gcaacatcct   3900
ggactacgcc aacaaacagc tggccggcct ggtggccaac tactacacac ctagatggcg   3960
gctgtttctg gaagctctgg tggactctgt ggcccagggc atcccattcc agcagcacca   4020
gttcgacaag aacgtgttcc agctggaaca ggctttcgtg ctgagcaagc agagataccc   4080
cagccagcct agaggcgaca cagtggacct ggccaagaag atctttctga agtactaccc   4140
cagatgggtg gccggctctt ggtgagaatt cgagctcggt acccgggaat caattcactc   4200
ctcaggtgca ggctgcctat cagaaggtgg tggctggtgt ggccaatgcc ctggctcaca   4260
aataccactg agatcttttt ccctctgcca aaaattatgg ggacatcatg aagccccttg   4320
agcatctgac ttctggctaa taaaggaaat ttattttcat tgcaatagtg tgttggaatt   4380
ttttgtgtct ctcactcgga aggacatatg ggagggcaaa tcatttaaaa catcagaatg   4440
agtatttggt ttagagtttg gcaacatatg cccatatgct ggctgccatg aacaaaggtt   4500
ggctataaag aggtcatcag tatatgaaac agccccctgc tgtccattcc ttattccata   4560
gaaaagcctt gacttgaggt tagatttttt ttatattttg ttttgtgtta tttttttctt   4620
taacatccct aaaattttcc ttacatgttt tactagccag atttttcctc ctctcctgac   4680
tactcccagt catagctgtc cctcttctct tatggagatc cctcgacctg cagcccaagc   4740
tgtagataag tagcatggcg ggttaatcat taactacaag gaacccctag tgatggagtt   4800
ggccactccc tctctgcgcg ctcgctcgct cactgaggcc gcccgggctt tgcccgggcg   4860
gcctcagtga gcgagcgagc gcgcagctgc attaatgaat cggccaacgc gcggggagag   4920
gcggtttgcg tattgggcgc tcttccgctt cctcgctcac tgactcgctg cgctcggtcg   4980
ttcggctgcg gcgagcggta tcagctcact caaaggcggt aatacggtta tccacagaat   5040
caggggataa cgcaggaaag aacatgtgag caaaaggcca gcaaaaggcc aggaaccgta   5100
aaaaggccgc gttgctggcg tttttccata ggctccgccc ccctgacgag catcacaaaa   5160
atcgacgctc aagtcagagg tggcgaaacc cgacaggact ataaagatac caggcgtttc   5220
cccctggaag ctccctcgtg cgctctcctg ttccgaccct gccgcttacc ggatacctgt   5280
ccgcctttct cccttcggga agcgtggcgc tttctcatag ctcacgctgt aggtatctca   5340
gttcggtgta ggtcgttcgc tccaagctgg gctgtgtgca cgaacccccc gttcagcccg   5400
accgctgcgc cttatccggt aactatcgtc ttgagtccaa cccggtaaga cacgacttat   5460
cgccactggc agcagccact ggtaacagga ttagcagagc gaggtatgta ggcggtgcta   5520
```

-continued

```
cagagttctt gaagtggtgg cctaactacg gctacactag aagaacagta tttggtatct   5580
gcgctctgct gaagccagtt accttcggaa aaagagttgg tagctcttga tccggcaaac   5640
aaaccaccgc tggtagcggt ggtttttttg tttgcaagca gcagattacg cgcagaaaaa   5700
aaggatctca agaagatcct ttgatctttt ctacggggtc tgacgctcag tggaacgaaa   5760
actcacgtta agggattttg gtcatgagat tatcaaaaag gatcttcacc tagatccttt   5820
taaattaaaa atgaagtttt aaatcaatct aaagtatata tgagtaaact tggtctgaca   5880
gttaccaatg cttaatcagt gaggcaccta tctcagcgat ctgtctattt cgttcatcca   5940
tagttgcctg actccccgtc gtgtagataa ctacgatacg ggagggctta ccatctggcc   6000
ccagtgctgc aatgataccg cgagacccac gctcaccggc tccagattta tcagcaataa   6060
accagccagc cggaagggcc gagcgcagaa gtggtcctgc aactttatcc gcctccatcc   6120
agtctattaa ttgttgccgg gaagctagag taagtagttc gccagttaat agtttgcgca   6180
acgttgttgc cattgctaca ggcatcgtgg tgtcacgctc gtcgtttggt atggcttcat   6240
tcagctccgg ttcccaacga tcaaggcgag ttacatgatc ccccatgttg tgcaaaaaag   6300
cggttagctc cttcggtcct ccgatcgttg tcagaagtaa gttggccgca gtgttatcac   6360
tcatggttat ggcagcactg cataattctc ttactgtcat gccatccgta agatgctttt   6420
ctgtgactgg tgagtactca accaagtcat tctgagaata gtgtatgcgg cgaccgagtt   6480
gctcttgccc ggcgtcaata cgggataata ccgcgccaca tagcagaact ttaaaagtgc   6540
tcatcattgg aaaacgttct tcggggcgaa aactctcaag gatcttaccg ctgttgagat   6600
ccagttcgat gtaacccact cgtgcaccca actgatcttc agcatctttt actttcacca   6660
gcgtttctgg gtgagcaaaa acaggaaggc aaaatgccgc aaaaaaggga ataagggcga   6720
cacggaaatg ttgaatactc atactcttcc tttttcaata ttattgaagc atttatcagg   6780
gttattgtct catgagcgga tacatatttg aatgtattta gaaaaataaa caaatagggg   6840
ttccgcgcac atttccccga aaagtgccac ctgacgtcta agaaaccatt attatcatga   6900
cattaaccta taaaaatagg cgtatcacga ggccctttcg tctcgcgcgt ttcggtgatg   6960
acggtgaaaa cctctgacac atgcagctcc cggagacggt cacagcttgt ctgtaagcgg   7020
atgccgggag cagacaagcc cgtcagggcg cgtcagcggg tgttggcggg tgtcggggct   7080
ggcttaacta tgcggcatca gagcagattg tactgagagt gcaccatatg cggtgtgaaa   7140
taccgcacag atgcgtaagg agaaaatacc gcatcaggcg attccaacat ccaataaatc   7200
atacaggcaa ggcaaagaat tagcaaaatt aagcaataaa gcctcagagc ataaagctaa   7260
atcggttgta ccaaaaacat tatgaccctg taatactttt gcgggagaag cctttatttc   7320
aacgcaagga taaaaatttt tagaaccctc atatatttta aatgcaatgc ctgagtaatg   7380
tgtaggtaaa gattcaaacg ggtgagaaag gccggagaca gtcaaatcac catcaatatg   7440
atattcaacc gttctagctg ataaattcat gccggagagg gtagctattt ttgagaggtc   7500
tctacaaagg ctatcaggtc attgcctgag agtctggagc aaacaagaga atcgatgaac   7560
ggtaatcgta aaactagcat gtcaatcata tgtaccccgg ttgataatca gaaaagcccc   7620
aaaaacagga agattgtata agcaaatatt taaattgtaa gcgttaatat tttgttaaaa   7680
ttcgcgttaa atttttgtta aatcagctca ttttttaacc aataggccga aatcggcaaa   7740
atcccttata aatcaaaaga atagaccgag atagggttga gtgttgttcc agtttggaac   7800
aagagtccac tattaaagaa cgtggactcc aacgtcaaag ggcgaaaaac cgtctatcag   7860
ggcgatggcc cactacgtga accatcaccc taatcaagtt ttttggggtc gaggtgccgt   7920
```

aaagcactaa atcggaaccc taaagggagc ccccgattta gagcttgacg gggaaagccg 7980
gcgaacgtgg cgagaaagga agggaagaaa gcgaaaggag cgggcgctag ggcgctggca 8040
agtgtagcgg tcacgctgcg cgtaaccacc acacccgccg cgcttaatgc gccgctacag 8100
ggcgcgtact atggttgctt tgacgagcac gtataacgtg ctttcctcgt tagaatcaga 8160
gcgggagcta aacaggaggc cgattaaagg gattttagac aggaacggta cgccagaatc 8220
ctgagaagtg tttttataat cagtgaggcc accgagtaaa agagtctgtc catcacgcaa 8280
attaaccgtt gtcgcaatac ttctttgatt agtaataaca tcacttgcct gagtagaaga 8340
actcaaacta tcggccttgc tggtaatatc cagaacaata ttaccgccag ccattgcaac 8400
ggaatcgcca ttcgccattc aggctgcgca actgttggga agggcgatcg gtgcgggcct 8460
cttcgct 8467

<210> SEQ ID NO 7
<211> LENGTH: 8472
<212> TYPE: DNA
<213> ORGANISM: Artificial Sequence
<220> FEATURE:
<223> OTHER INFORMATION: pAAV-CAG-comNaGlu Nucleotide sequence

<400> SEQUENCE: 7
attacgccag ctgcgcgctc gctcgctcac tgaggccgcc cgggcaaagc ccgggcgtcg 60
ggcgaccttt ggtcgcccgg cctcagtgag cgagcgagcg cgcagagagg gagtggccaa 120
ctccatcact aggggttcct tgtagttaat gattaacccg ccatgctact tatctactcg 180
acattgatta ttgactagtt attaatagta atcaattacg gggtcattag ttcatagccc 240
atatatggag ttccgcgtta cataacttac ggtaaatggc ccgcctggct gaccgcccaa 300
cgacccccgc ccattgacgt caataatgac gtatgttccc atagtaacgc caatagggac 360
tttccattga cgtcaatggg tggagtattt acggtaaact gcccacttgg cagtacatca 420
agtgtatcat atgccaagta cgccccctat tgacgtcaat gacggtaaat ggcccgcctg 480
gcattatgcc cagtacatga ccttatggga ctttcctact tggcagtaca tctacgtatt 540
agtcatcgct attaccatgg tcgaggtgag ccccacgttc tgcttcactc tccccatctc 600
ccccccctcc ccacccccaa ttttgtattt atttattttt taattatttt gtgcagcgat 660
gggggcgggg gggggggggg ggcgcgcgcc aggcggggcg gggcggggcg aggggcgggg 720
cggggcgagg cggagaggtg cggcggcagc caatcagagc ggcgcgctcc gaaagtttcc 780
ttttatggcg aggcggcggc ggcggcggcc ctataaaaag cgaagcgcgc ggcgggcggg 840
agtcgctgcg ttgccttcgc cccgtgcccc gctccgccgc cgcctcgcgc cgcccgcccc 900
ggctctgact gaccgcgtta ctcccacagg tgagcgggcg ggacggccct tctcctccgg 960
gctgtaatta gcgcttggtt taatgacggc ttgtttcttt tctgtggctg cgtgaaagcc 1020
ttgaggggct ccgggagggc cctttgtgcg gggggagcgg ctcggggggt gcgtgcgtgt 1080
gtgtgtgcgt ggggagcgcc gcgtgcggct ccgcgctgcc cggcggctgt gagcgctgcg 1140
ggcgcggcgc ggggctttgt gcgctccgca gtgtgcgcga ggggagcgcg gccgggggcg 1200
gtgccccgcg gtgcgggggg ggctgcgagg ggaacaaagg ctgcgtgcgg ggtgtgtgcg 1260
tgggggggtg agcagggggt gtgggcgcgt cggtcgggct gcaacccccc ctgcaccccc 1320
ctccccgagt tgctgagcac ggcccggctt cgggtgcggg gctccgtacg gggcgtggcg 1380
cggggctcgc cgtgccgggc gggggtggc ggcaggtggg ggtgccgggc ggggcggggc 1440

```
cgcctcgggc cggggagggc tcgggggagg ggcgcggcgg cccccggagc gccggcggct   1500
gtcgaggcgc ggcgagccgc agccattgcc ttttatggta atcgtgcgag agggcgcagg   1560
gacttccttt gtcccaaatc tgtgcggagc cgaaatctgg gaggcgccgc cgcacccccct  1620
ctagcgggcg cggggcgaag cggtgcggcg ccggcaggaa ggaaatgggc ggggagggcc   1680
ttcgtgcgtc gccgcgccgc cgtccccttc tccctctcca gcctcggggc tgtccgcggg   1740
gggacggctg ccttcggggg ggacggggca gggcggggtt cggcttctgg cgtgtgaccg   1800
gcggctctag agcctctgct aaccatgttc atgccttctt ctttttccta cagctcctgg   1860
gcaacgtgct ggttattgtg ctgtctcatc attttggcaa agaattgatt aattcgagcg   1920
aacgcgtgct agcgccacca tggaagctgc cggcctggcc gtgatcctgg gctttctgct   1980
gctggctggc ggctctgtgg gcgacgaggc cagagaagcc aaggctgtgc gcgagctggt   2040
cgtgcgcctg ctgggacctg gccctgccgc caacttcctg gtgtccgtgg aaagagccct   2100
ggccgacgag agcggcctgg acacatacag cctgtctggc ggcggaggcg tgccagttct   2160
ggtgcgcgga tctacaggcg tggccgctgc cgctggcctg cacagatacc tgagagactt   2220
ctgcggctgc caggtggcct ggtccagcgc tcagctgcat ctgccttggc cctgcctgc    2280
cgtgcctgac ggcctgaccg agacaacccc caacagatac cggtactacc agaacgtgtg   2340
cacccacagc tacagcttcg tctggtggga ctgggccaga tgggagcaag aaatcgactg   2400
gatggccctg aacggcatca acctggctct ggcctggaac ggccaagaag ccatctggca   2460
gagagtgtat ctggccctgg gcctgaccca gagcgagatc gacacctact tcaccggccc   2520
tgcctttctg gcttggggca gaatgggcaa cctgcacacc tgggacggcc ccctgcccag   2580
aagctggcac ctgagccagg tgtacctgca gcacagaatc ctggacagaa tgagaagctt   2640
cggcatgatc cccgtgctgc ccgccttcgc tggccacgtg cccaaggcca tcaccagagt   2700
gttcccccaa gtgaacgtga tcaagctggg cagctggggc cacttcaact gcagctactc   2760
ctgcagcttc ctgctggccc ctggcgaccc catgttcccc ctgatcggca acctgttcct   2820
gagagagctg accaaagagt tcggcaccga ccacatctac ggcgccgaca ccttcaacga   2880
gatgcagccc cccttcagcg acccctctta cctggccgcc accacagccg ccgtgtacga   2940
ggccatggtg acagtggacc ccgacgccgt gtggctgctg cagggctggc tgttccagca   3000
ccagccccag ttctggggac ctagccagat cagagccgtg ctggaagccg tgcccagagg   3060
cagactgctg gtgctggacc tgttcgccga gagccacccc gtgtacatgc acaccgccag   3120
cttccacggc cagcccttca tctggtgcat gctgcacaac ttcggcggca accacggcct   3180
gttcggcgcc ctggaagatg tgaacagagg cccccaggcc gccagactgt tccccaacag   3240
caccatggtc ggaaccggaa tcgcccccga gggcatcggc cagaacgagg tggtgtacgc   3300
cctgatggcc gagctgggct ggcggaagga ccctgtgcct gacctgatgg cctgggtgtc   3360
cagcttcgcc atcagacgct acggcgtgtc ccagcctgat gccgtggccg cttggaagct   3420
gctgctgaga agcgtgtaca actgcagcgg cgaggcctgc agcggccaca acagatcccc   3480
cctggtgaaa agacccagcc tgcagatgag caccgccgtg tggtacaacc gcagcgacgt   3540
gttcgaggcc tggcgcctgc tgctgacagc cgcccctaac ctgaccacct cccccgcctt   3600
cagatacgac ctgctggacg tgaccagaca ggccgtgcaa gaactggtgt ccctgtgcta   3660
cgaggaagcc agaaccgcct acctgaaaca agaactggac ctgctcctgc gggcaggcgg   3720
cctgctggtg tacaagctgc tgcccaccct ggacgagctg ctggccagct ctagccactt   3780
tctgctgggc acatggctgg accaggccag aaaggccgct gtgtctgagg ccgaggccca   3840
```

```
gttctacgag cagaacagca gataccagat caccctgtgg ggccctgagg gcaacatcct   3900
ggactacgcc aacaagcagc tggctggcct ggtggccgac tactaccagc ccagatggtg   3960
cctgttcctg ggcaccctgg cccacagcct ggctagaggc gtgcccttcc agcagcacga   4020
gttcgagaag aacgtgttcc ctctggaaca ggccttcgtg tacaacaaga agagataccc   4080
cagccagccc agaggcgaca ccgtggacct gagcaagaag atcttcctga agtaccaccc   4140
ccagcccgac agcctgtgat gagcggccgc gaattcgagc tcggtacccg ggaatcaatt   4200
cactcctcag gtgcaggctg cctatcagaa ggtggtggct ggtgtggcca atgccctggc   4260
tcacaaatac cactgagatc tttttccctc tgccaaaaat tatggggaca tcatgaagcc   4320
ccttgagcat ctgacttctg gctaataaag gaaatttatt ttcattgcaa tagtgtgttg   4380
gaattttttg tgtctctcac tcggaaggac atatgggagg gcaaatcatt taaaacatca   4440
gaatgagtat ttggtttaga gtttggcaac atatgcccat atgctggctg ccatgaacaa   4500
aggttggcta taaagaggtc atcagtatat gaaacagccc cctgctgtcc attccttatt   4560
ccatagaaaa gccttgactt gaggttagat ttttttatat ttttgttttg tgttattttt   4620
ttctttaaca tccctaaaat ttccttaca tgttttacta gccagatttt tcctcctctc   4680
ctgactactc ccagtcatag ctgtccctct tctcttatgg agatccctcg acctgcagcc   4740
caagctgtag ataagtagca tggcgggtta atcattaact acaaggaacc cctagtgatg   4800
gagttggcca ctccctctct gcgcgctcgc tcgctcactg aggccgcccg ggctttgccc   4860
gggcggcctc agtgagcgag cgagcgcgca gctgcattaa tgaatcggcc aacgcgcggg   4920
gagaggcggt ttgcgtattg ggcgctcttc cgcttcctcg ctcactgact cgctgcgctc   4980
ggtcgttcgg ctgcggcgag cggtatcagc tcactcaaag gcggtaatac ggttatccac   5040
agaatcaggg gataacgcag gaaagaacat gtgagcaaaa ggccagcaaa aggccaggaa   5100
ccgtaaaaag gccgcgttgc tggcgttttt ccataggctc cgcccccctg acgagcatca   5160
caaaaatcga cgctcaagtc agaggtggcg aaacccgaca ggactataaa gataccaggc   5220
gtttccccct ggaagctccc tcgtgcgctc tcctgttccg accctgccgc ttaccggata   5280
cctgtccgcc tttctccctt cgggaagcgt ggcgctttct catagctcac gctgtaggta   5340
tctcagttcg gtgtaggtcg ttcgctccaa gctgggctgt gtgcacgaac cccccgttca   5400
gcccgaccgc tgcgccttat ccggtaacta tcgtcttgag tccaacccgg taagacacga   5460
cttatcgcca ctggcagcag ccactggtaa caggattagc agagcgaggt atgtaggcgg   5520
tgctacagag ttcttgaagt ggtggcctaa ctacggctac actagaagaa cagtatttgg   5580
tatctgcgct ctgctgaagc cagttacctt cggaaaaaga gttggtagct cttgatccgg   5640
caaacaaacc accgctggta gcggtggttt ttttgtttgc aagcagcaga ttacgcgcag   5700
aaaaaaagga tctcaagaag atcctttgat cttttctacg gggtctgacg ctcagtggaa   5760
cgaaaactca cgttaaggga ttttggtcat gagattatca aaaaggatct tcacctagat   5820
ccttttaaat taaaaatgaa gttttaaatc aatctaaagt atatatgagt aaacttggtc   5880
tgacagttac caatgcttaa tcagtgaggc acctatctca gcgatctgtc tatttcgttc   5940
atccatagtt gcctgactcc ccgtcgtgta gataactacg atacgggagg gcttaccatc   6000
tggccccagt gctgcaatga taccgcgaga cccacgctca ccggctccag atttatcagc   6060
aataaaccag ccagccggaa gggccgagcg cagaagtggt cctgcaactt tatccgcctc   6120
catccagtct attaattgtt gccgggaagc tagagtaagt agttcgccag ttaatagttt   6180
```

```
gcgcaacgtt gttgccattg ctacaggcat cgtggtgtca cgctcgtcgt ttggtatggc   6240
ttcattcagc tccggttccc aacgatcaag gcgagttaca tgatccccca tgttgtgcaa   6300
aaaagcggtt agctccttcg gtcctccgat cgttgtcaga agtaagttgg ccgcagtgtt   6360
atcactcatg gttatggcag cactgcataa ttctcttact gtcatgccat ccgtaagatg   6420
cttttctgtg actggtgagt actcaaccaa gtcattctga gaatagtgta tgcggcgacc   6480
gagttgctct tgcccggcgt caatacggga taataccgcg ccacatagca gaactttaaa   6540
agtgctcatc attggaaaac gttcttcggg gcgaaaactc tcaaggatct taccgctgtt   6600
gagatccagt tcgatgtaac ccactcgtgc acccaactga tcttcagcat cttttacttt   6660
caccagcgtt tctgggtgag caaaaacagg aaggcaaaat gccgcaaaaa agggaataag   6720
ggcgacacgg aaatgttgaa tactcatact cttccttttt caatattatt gaagcattta   6780
tcagggttat tgtctcatga gcggatacat atttgaatgt atttagaaaa ataaacaaat   6840
aggggttccg cgcacatttc cccgaaaagt gccacctgac gtctaagaaa ccattattat   6900
catgacatta acctataaaa ataggcgtat cacgaggccc tttcgtctcg cgcgtttcgg   6960
tgatgacggt gaaaacctct gacacatgca gctcccggag acggtcacag cttgtctgta   7020
agcggatgcc gggagcagac aagcccgtca gggcgcgtca gcgggtgttg gcgggtgtcg   7080
gggctggctt aactatgcgg catcagagca gattgtactg agagtgcacc atatgcggtg   7140
tgaaataccg cacagatgcg taaggagaaa ataccgcatc aggcgattcc aacatccaat   7200
aaatcataca ggcaaggcaa agaattagca aaattaagca ataaagcctc agagcataaa   7260
gctaaatcgg ttgtaccaaa aacattatga ccctgtaata cttttgcggg agaagccttt   7320
atttcaacgc aaggataaaa atttttagaa ccctcatata ttttaaatgc aatgcctgag   7380
taatgtgtag gtaaagattc aaacgggtga gaaaggccgg agacagtcaa atcaccatca   7440
atatgatatt caaccgttct agctgataaa ttcatgccgg agagggtagc tatttttgag   7500
aggtctctac aaaggctatc aggtcattgc ctgagagtct ggagcaaaca agagaatcga   7560
tgaacggtaa tcgtaaaact agcatgtcaa tcatatgtac cccggttgat aatcagaaaa   7620
gccccaaaaa caggaagatt gtataagcaa atatttaaat tgtaagcgtt aatattttgt   7680
taaaattcgc gttaaatttt tgttaaatca gctcattttt taaccaatag gccgaaatcg   7740
gcaaaatccc ttataaatca aaagaataga ccgagatagg gttgagtgtt gttccagttt   7800
ggaacaagag tccactatta aagaacgtgg actccaacgt caaagggcga aaaaccgtct   7860
atcagggcga tggcccacta cgtgaaccat caccctaatc aagttttttg gggtcgaggt   7920
gccgtaaagc actaaatcgg aaccctaaag ggagcccccg atttagagct tgacggggaa   7980
agccggcgaa cgtggcgaga aaggaaggga agaaagcgaa aggagcgggc gctagggcgc   8040
tggcaagtgt agcggtcacg ctgcgcgtaa ccaccacacc cgccgcgctt aatgcgccgc   8100
tacagggcgc gtactatggt tgctttgacg agcacgtata acgtgctttc ctcgttagaa   8160
tcagagcggg agctaaacag gaggccgatt aaagggattt tagacaggaa cggtacgcca   8220
gaatcctgag aagtgttttt ataatcagtg aggccaccga gtaaaagagt ctgtccatca   8280
cgcaaattaa ccgttgtcgc aatacttctt tgattagtaa taacatcact tgcctgagta   8340
gaagaactca aactatcggc cttgctggta atatccagaa caatattacc gccagccatt   8400
gcaacggaat cgccattcgc cattcaggct gcgcaactgt tgggaagggc gatcggtgcg   8460
ggcctcttcg ct                                                       8472
```

```
<210> SEQ ID NO 8
<211> LENGTH: 8479
<212> TYPE: DNA
<213> ORGANISM: Artificial Sequence
<220> FEATURE:
<223> OTHER INFORMATION: pAAV-CAG-cocNaGlu Nucleotide sequence

<400> SEQUENCE: 8

attacgccag ctgcgcgctc gctcgctcac tgaggccgcc cgggcaaagc ccgggcgtcg      60

ggcgaccttt ggtcgcccgg cctcagtgag cgagcgagcg cgcagagagg gagtggccaa     120

ctccatcact aggggttcct tgtagttaat gattaacccg ccatgctact tatctactcg     180

acattgatta ttgactagtt attaatagta atcaattacg gggtcattag ttcatagccc     240

atatatggag ttccgcgtta cataacttac ggtaaatggc ccgcctggct gaccgcccaa     300

cgacccccgc ccattgacgt caataatgac gtatgttccc atagtaacgc caatagggac     360

tttccattga cgtcaatggg tggagtattt acggtaaact gcccacttgg cagtacatca     420

agtgtatcat atgccaagta cgccccctat tgacgtcaat gacggtaaat ggcccgcctg     480

gcattatgcc cagtacatga ccttatggga ctttcctact tggcagtaca tctacgtatt     540

agtcatcgct attaccatgg tcgaggtgag ccccacgttc tgcttcactc tccccatctc     600

ccccccctcc ccacccccaa ttttgtattt atttattttt taattatttt gtgcagcgat     660

gggggcgggg gggggggggg ggcgcgcgcc aggcggggcg gggcggggcg aggggcgggg     720

cggggcgagg cggagaggtg cggcggcagc caatcagagc ggcgcgctcc gaaagtttcc     780

ttttatggcg aggcggcggc ggcggcggcc ctataaaaag cgaagcgcgc ggcgggcggg     840

agtcgctgcg ttgccttcgc cccgtgcccc gctccgccgc cgcctcgcgc cgcccgcccc     900

ggctctgact gaccgcgtta ctcccacagg tgagcgggcg ggacggccct tctcctccgg     960

gctgtaatta gcgcttggtt taatgacggc ttgtttcttt tctgtggctg cgtgaaagcc    1020

ttgaggggct ccgggagggc cctttgtgcg gggggagcgg ctcggggggt gcgtgcgtgt    1080

gtgtgtgcgt ggggagcgcc gcgtgcggct ccgcgctgcc cggcggctgt gagcgctgcg    1140

ggcgcggcgc ggggctttgt gcgctccgca gtgtgcgcga ggggagcgcg gccgggggcg    1200

gtgccccgcg gtgcgggggg ggctgcgagg ggaacaaagg ctgcgtgcgg ggtgtgtgcg    1260

tgggggggtg agcagggggt gtgggcgcgt cggtcgggct gcaacccccc ctgcaccccc    1320

ctccccgagt tgctgagcac ggcccggctt cgggtgcggg gctccgtacg gggcgtggcg    1380

cggggctcgc cgtgccgggc ggggggtggc ggcaggtggg ggtgccgggc ggggcggggc    1440

cgcctcgggc cggggagggc tcgggggagg ggcgcggcgg cccccggagc gccggcggct    1500

gtcgaggcgc ggcgagccgc agccattgcc ttttatggta atcgtgcgag agggcgcagg    1560

gacttccttt gtcccaaatc tgtgcggagc cgaaatctgg gaggcgccgc cgcaccccct    1620

ctagcgggcg cggggcgaag cggtgcggcg ccggcaggaa ggaaatgggc ggggagggcc    1680

ttcgtgcgtc gccgcgccgc cgtccccttc tccctctcca gcctcggggc tgtccgcggg    1740

gggacggctg ccttcggggg ggacggggca gggcggggtt cggcttctgg cgtgtgaccg    1800

gcggctctag agcctctgct aaccatgttc atgccttctt ctttttccta cagctcctgg    1860

gcaacgtgct ggttattgtg ctgtctcatc attttggcaa agaattgatt aattcgagcg    1920

aacgcgtgcc accatgggag ctgccgctgc tgctgctgtc ctgggcctcc tgctcctggg    1980

agctgctggc ggagccgccg ctgatgaagc cagagaagcc gctgccgtgc gggctctgct    2040

cgtcagactg ctgggacctg gacccgcagc tgccttcagc gtgtccgtga aagagccct    2100
```

```
ggccgccgag agcggcctgg acacctatag actgtctggc ggcggagccg gcaccagggt   2160
gctggtgctg ggatctacag gtgtcgccgc tgccgccgga ctgcacagat acctgaggga   2220
cttctgcggc tgccatgtgg cttggagcgg cagccagctg agactgcctg agcctctgcc   2280
tgccgtgcct caggtgctga ccgaggccac ccccaacaga taccggtact accagaacgt   2340
gtgcacccac agctacagct tcgtctggtg ggactgggcc agatgggagc gcgagctgga   2400
ctggatggcc ctgaacggca tcaacctggc tctcgcttgg agtggccagg aagccatctg   2460
gcagagggtg tacctggccc tgggcctgac ccagagcgag atcgacgagt acttcaccgg   2520
ccctgccttt ctggcctggg gcaggatggg caacctgcac acctggggcg gacccctgcc   2580
tcacagctgg cacctgaagc agctgtacct gcagcacagg atcctggaca ggatgcggag   2640
cttcggcatg atccccgtgc tgcccgcctt cagcggccac gtgccaaagg ccctgaccag   2700
ggtgttcccc cagatcaaca tcacacagct cggaagttgg ggccacttca actgcagcta   2760
ctcctgcagc ttcctgctgg cccccgagga cccccctgttc cctatcatcg gcagcctgtt   2820
tctgagagag ctgatccagg aatttggcac caaccacatc tacggcgccg acaccttcaa   2880
cgagatgcag ccccccagca gcgagcccag ctacctggcc tctgccaccg ccagcgtgta   2940
ccaggccatg atcaccgtgg acagcgacgc cgtgtggctg ctgcagggct ggctgttcca   3000
gcaccagcct cagttctggg gccctgccca ggtcaaagcc gtgctggaag ccgtgcccag   3060
gggcaggctg ctcgtgctgg atctgttcgc cgagagccag cccgtgtaca tccagaccgc   3120
cagcttccag ggccagccct tcatctggtg catgctgcac aacttcggcg gcaaccacgg   3180
cctgttcgga gccctcgagg ccgtgaatag aggcccagcc gccgctaggc tgttccccaa   3240
ctctaccatg ctgggcaccg gaatggcccc tgagggcatc ggccagaacg aggtggtgta   3300
cgccctgatg gccgagctgg gctggcggaa ggatcccgtg gccgatctgg aagcctgggt   3360
gtccagcttc gccgctcgga gatacggcgt ggcccacaga gataccgaag ccgcctggag   3420
actgctgctg agaagcgtgt acaactgcag cggcgaggcc tgctccggcc acaacagatc   3480
tccactcgtg cggaggccct ccctgcagat ggtcaccacc gtgtggtata accgcagcga   3540
cgtgttcgag gcttggagac tgctgctgac cgccgctcct accctggcca gcagccccac   3600
cttcagatac gacctgctgg acgtgaccag gcaggccgcc caggaactcg tcagcctgta   3660
ctacgtggaa gccagaagcg cctacctgcg gaaagaactg gtgcccctgc tgagggccgc   3720
tggcgtgctg gtgtatgagc tgctgcctgc cctggacaag gtgctggcta gcgactcccg   3780
gttcctgctg ggcagatggc tggaacaggc cagggctgcc gccgtgtctg aagccgaggc   3840
ccacctgtac gagcagaaca gcagatacca gctgaccctg tggggacccg agggcaacat   3900
cctggactac gccaacaagc agctggccgg cctggtggcc gactactaca cccccagatg   3960
gcggctgttc atggaaatgc tggtggaaag cctggtgcag ggcatcccat tccagcagca   4020
ccagttcgac aagaacgcct tccagctcga gcagaccttc atcttcggca cccagagata   4080
ccccagccag cccgacggcg acaccgtgga cctggccaag aagctgttca tcaagtacta   4140
ccccaggctg gtggccggct ccctgtgggc cgattgagaa ttcgagctcg gtacccggga   4200
atcaattcac tcctcaggtg caggctgcct atcagaaggt ggtggctggt gtggccaatg   4260
ccctggctca caaataccac tgagatcttt ttccctctgc caaaaattat ggggacatca   4320
tgaagcccct tgagcatctg acttctggct aataaaggaa atttattttc attgcaatag   4380
tgtgttggaa tttttttgtgt ctctcactcg gaaggacata tgggagggca aatcatttaa   4440
aacatcagaa tgagtatttg gtttagagtt tggcaacata tgcccatatg ctggctgcca   4500
```

```
tgaacaaagg ttggctataa agaggtcatc agtatatgaa acagccccct gctgtccatt   4560
ccttattcca tagaaaagcc ttgacttgag gttagatttt ttttatattt tgttttgtgt   4620
tattttttttc tttaacatcc ctaaaatttt ccttacatgt tttactagcc agatttttcc   4680
tcctctcctg actactccca gtcatagctg tccctcttct cttatggaga tccctcgacc   4740
tgcagcccaa gctgtagata agtagcatgg cgggttaatc attaactaca aggaacccct   4800
agtgatggag ttggccactc cctctctgcg cgctcgctcg ctcactgagg ccgcccgggc   4860
tttgcccggg cggcctcagt gagcgagcga gcgcgcagct gcattaatga atcggccaac   4920
gcgcggggag aggcggtttg cgtattgggc gctcttccgc ttcctcgctc actgactcgc   4980
tgcgctcggt cgttcggctg cggcgagcgg tatcagctca ctcaaaggcg gtaatacggt   5040
tatccacaga atcaggggat aacgcaggaa agaacatgtg agcaaaaggc cagcaaaagg   5100
ccaggaaccg taaaaaggcc gcgttgctgg cgtttttcca taggctccgc ccccctgacg   5160
agcatcacaa aaatcgacgc tcaagtcaga ggtggcgaaa cccgacagga ctataaagat   5220
accaggcgtt tccccctgga agctccctcg tgcgctctcc tgttccgacc ctgccgctta   5280
ccggatacct gtccgccttt ctcccttcgg gaagcgtggc gctttctcat agctcacgct   5340
gtaggtatct cagttcggtg taggtcgttc gctccaagct gggctgtgtg cacgaacccc   5400
ccgttcagcc cgaccgctgc gccttatccg gtaactatcg tcttgagtcc aacccggtaa   5460
gacacgactt atcgccactg gcagcagcca ctggtaacag gattagcaga gcgaggtatg   5520
taggcggtgc tacagagttc ttgaagtggt ggcctaacta cggctacact agaagaacag   5580
tatttggtat ctgcgctctg ctgaagccag ttaccttcgg aaaaagagtt ggtagctctt   5640
gatccggcaa acaaaccacc gctggtagcg gtggtttttt tgtttgcaag cagcagatta   5700
cgcgcagaaa aaaaggatct caagaagatc ctttgatctt ttctacgggg tctgacgctc   5760
agtggaacga aaactcacgt taagggattt tggtcatgag attatcaaaa aggatcttca   5820
cctagatcct tttaaattaa aaatgaagtt ttaaatcaat ctaaagtata tatgagtaaa   5880
cttggtctga cagttaccaa tgcttaatca gtgaggcacc tatctcagcg atctgtctat   5940
ttcgttcatc catagttgcc tgactccccg tcgtgtagat aactacgata cgggagggct   6000
taccatctgg ccccagtgct gcaatgatac cgcgagaccc acgctcaccg gctccagatt   6060
tatcagcaat aaaccagcca gccggaaggg ccgagcgcag aagtggtcct gcaactttat   6120
ccgcctccat ccagtctatt aattgttgcc gggaagctag agtaagtagt tcgccagtta   6180
atagtttgcg caacgttgtt gccattgcta caggcatcgt ggtgtcacgc tcgtcgtttg   6240
gtatggcttc attcagctcc ggttcccaac gatcaaggcg agttacatga tcccccatgt   6300
tgtgcaaaaa agcggttagc tccttcggtc ctccgatcgt tgtcagaagt aagttggccg   6360
cagtgttatc actcatggtt atggcagcac tgcataattc tcttactgtc atgccatccg   6420
taagatgctt ttctgtgact ggtgagtact caaccaagtc attctgagaa tagtgtatgc   6480
ggcgaccgag ttgctcttgc ccggcgtcaa tacgggataa taccgcgcca catagcagaa   6540
ctttaaaagt gctcatcatt ggaaaacgtt cttcggggcg aaaactctca aggatcttac   6600
cgctgttgag atccagttcg atgtaaccca ctcgtgcacc caactgatct tcagcatctt   6660
ttactttcac cagcgtttct gggtgagcaa aaacaggaag gcaaaatgcc gcaaaaaagg   6720
gaataagggc gacacggaaa tgttgaatac tcatactctt cctttttcaa tattattgaa   6780
gcatttatca gggttattgt ctcatgagcg gatacatatt tgaatgtatt tagaaaaata   6840
```

```
aacaaatagg ggttccgcgc acatttcccc gaaaagtgcc acctgacgtc taagaaacca   6900

ttattatcat gacattaacc tataaaaata ggcgtatcac gaggcccttt cgtctcgcgc   6960

gtttcggtga tgacggtgaa aacctctgac acatgcagct cccggagacg gtcacagctt   7020

gtctgtaagc ggatgccggg agcagacaag cccgtcaggg cgcgtcagcg ggtgttggcg   7080

ggtgtcgggg ctggcttaac tatgcggcat cagagcagat tgtactgaga gtgcaccata   7140

tgcggtgtga aataccgcac agatgcgtaa ggagaaaata ccgcatcagg cgattccaac   7200

atccaataaa tcatacaggc aaggcaaaga attagcaaaa ttaagcaata aagcctcaga   7260

gcataaagct aaatcggttg taccaaaaac attatgaccc tgtaatactt ttgcgggaga   7320

agcctttatt tcaacgcaag gataaaaatt tttagaaccc tcatatattt taaatgcaat   7380

gcctgagtaa tgtgtaggta aagattcaaa cgggtgagaa aggccggaga cagtcaaatc   7440

accatcaata tgatattcaa ccgttctagc tgataaattc atgccggaga gggtagctat   7500

ttttgagagg tctctacaaa ggctatcagg tcattgcctg agagtctgga gcaaacaaga   7560

gaatcgatga acggtaatcg taaaactagc atgtcaatca tatgtacccc ggttgataat   7620

cagaaaagcc ccaaaaacag gaagattgta taagcaaata tttaaattgt aagcgttaat   7680

attttgttaa aattcgcgtt aaatttttgt taaatcagct cattttttaa ccaataggcc   7740

gaaatcggca aaatccctta taaatcaaaa gaatagaccg agatagggtt gagtgttgtt   7800

ccagtttgga acaagagtcc actattaaag aacgtggact ccaacgtcaa agggcgaaaa   7860

accgtctatc agggcgatgg cccactacgt gaaccatcac cctaatcaag ttttttgggg   7920

tcgaggtgcc gtaaagcact aaatcggaac cctaaaggga gcccccgatt tagagcttga   7980

cggggaaagc cggcgaacgt ggcgagaaag gaagggaaga aagcgaaagg agcgggcgct   8040

agggcgctgg caagtgtagc ggtcacgctg cgcgtaacca ccacacccgc cgcgcttaat   8100

gcgccgctac agggcgcgta ctatggttgc tttgacgagc acgtataacg tgctttcctc   8160

gttagaatca gagcgggagc taaacaggag gccgattaaa gggattttag acaggaacgg   8220

tacgccagaa tcctgagaag tgtttttata atcagtgagg ccaccgagta aaagagtctg   8280

tccatcacgc aaattaaccg ttgtcgcaat acttctttga ttagtaataa catcacttgc   8340

ctgagtagaa gaactcaaac tatcggcctt gctggtaata tccagaacaa tattaccgcc   8400

agccattgca acggaatcgc cattcgccat tcaggctgcg caactgttgg gaagggcgat   8460

cggtgcgggc ctcttcgct                                                8479
```

```
<210> SEQ ID NO 9
<211> LENGTH: 4880
<212> TYPE: DNA
<213> ORGANISM: Artificial Sequence
<220> FEATURE:
<223> OTHER INFORMATION: AAV9-CAG-hNaGlu Nucleotide sequence

<400> SEQUENCE: 9
```

```
attacgccag ctgcgcgctc gctcgctcac tgaggccgcc cgggcaaagc ccgggcgtcg     60

ggcgaccttt ggtcgcccgg cctcagtgag cgagcgagcg cgcagagagg gagtggccaa    120

ctccatcact aggggttcct tgtagttaat gattaacccg ccatgctact tatctactcg    180

acattgatta ttgactagtt attaatagta atcaattacg gggtcattag ttcatagccc    240

atatatggag ttccgcgtta cataacttac ggtaaatggc ccgcctggct gaccgcccaa    300

cgacccccgc ccattgacgt caataatgac gtatgttccc atagtaacgc caatagggac    360

tttccattga cgtcaatggg tggagtattt acggtaaact gcccacttgg cagtacatca    420
```

```
agtgtatcat atgccaagta cgccccctat tgacgtcaat gacggtaaat ggcccgcctg    480
gcattatgcc cagtacatga ccttatggga ctttcctact tggcagtaca tctacgtatt    540
agtcatcgct attaccatgg tcgaggtgag ccccacgttc tgcttcactc tccccatctc    600
ccccccctcc ccacccccaa ttttgtattt atttattttt taattatttt gtgcagcgat    660
gggggcgggg gggggggggg ggcgcgcgcc aggcggggcg gggcggggcg aggggcgggg    720
cggggcgagg cggagaggtg cggcggcagc caatcagagc ggcgcgctcc gaaagtttcc    780
ttttatggcg aggcggcggc ggcggcggcc ctataaaaag cgaagcgcgc ggcgggcggg    840
agtcgctgcg ttgccttcgc cccgtgcccc gctccgccgc cgcctcgcgc cgcccgcccc    900
ggctctgact gaccgcgtta ctcccacagg tgagcgggcg ggacggccct tctcctccgg    960
gctgtaatta gcgcttggtt taatgacggc ttgtttcttt tctgtggctg cgtgaaagcc   1020
ttgaggggct ccgggagggc cctttgtgcg gggggagcgg ctcggggggt gcgtgcgtgt   1080
gtgtgtgcgt ggggagcgcc gcgtgcggct ccgcgctgcc cggcggctgt gagcgctgcg   1140
ggcgcggcgc ggggctttgt gcgctccgca gtgtgcgcga ggggagcgcg gccgggggcg   1200
gtgccccgcg gtgcgggggg ggctgcgagg ggaacaaagg ctgcgtgcgg ggtgtgtgcg   1260
tgggggggtg agcagggggt gtgggcgcgt cggtcgggct gcaacccccc ctgcaccccc   1320
ctccccgagt tgctgagcac ggcccggctt cgggtgcggg gctccgtacg gggcgtggcg   1380
cggggctcgc cgtgccgggc ggggggtggc ggcaggtggg ggtgccgggc ggggcggggc   1440
cgcctcgggc cggggagggc tcgggggagg ggcgcggcgg cccccggagc gccggcggct   1500
gtcgaggcgc ggcgagccgc agccattgcc ttttatggta atcgtgcgag agggcgcagg   1560
gacttccttt gtcccaaatc tgtgcggagc cgaaatctgg gaggcgccgc cgcacccccct   1620
ctagcgggcg cggggcgaag cggtgcggcg ccggcaggaa ggaaatgggc ggggagggcc   1680
ttcgtgcgtc gccgcgccgc cgtccccttc tccctctcca gcctcggggc tgtccgcggg   1740
gggacggctg ccttcggggg ggacggggca gggcggggtt cggcttctgg cgtgtgaccg   1800
gcggctctag agcctctgct aaccatgttc atgccttctt ctttttccta cagctcctgg   1860
gcaacgtgct ggttattgtg ctgtctcatc attttggcaa agaattgatt aattcgagcg   1920
aacgcgtatg gaggcggtgg cggtggccgc ggcggtgggg gtccttctcc tggccggggc   1980
cgggggcgcg gcaggcgacg aggcccggga ggcggcggcc gtgcgggcgc tcgtggcccg   2040
gctgctgggg ccaggccccg cggccgactt ctccgtgtcg gtggagcgcg ctctggctgc   2100
caagccgggc ttggacacct acagcctggg cggcggcggc gcggcgcgcg tgcgggtgcg   2160
cggctccacg ggcgtggcgg ccgccgcggg gctgcaccgc tacctgcgcg acttctgtgg   2220
ctgccacgtg gcctggtccg gctctcagct gcgcctgccg cggccactgc cagccgtgcc   2280
gggggagctg accgaggcca cgcccaacag gtaccgctat taccagaatg tgtgcacgca   2340
aagctactct ttcgtgtggt gggactgggc ccgctgggag cgagagatag actggatggc   2400
gctgaatggc atcaacctgg cactggcctg gagcggccag gaggccatct ggcagcgggt   2460
gtacctggcc ttgggcctga cccaggcaga gatcaatgag ttctttactg gtcctgcctt   2520
cctggcctgg gggcgaatgg gcaacctgca cacctgggat ggccccctgc ccccctcctg   2580
gcacatcaag cagctttacc tgcagcaccg ggtcctggac cagatgcgct ccttcggcat   2640
gaccccagtg ctgcctgcat tcgcggggca tgttcccgag gctgtcacca gggtgttccc   2700
tcaggtcaat gtcacgaaga tgggcagttg ggccactttt aactgttcct actcctgctc   2760
```

```
cttccttctg gctccggaag accccatatt ccccatcatc gggagcctct tcctgcgaga   2820
gctgatcaaa gagtttggca cagaccacat ctatggggcc gacactttca atgagatgca   2880
gccaccttcc tcagagccct cctaccttgc cgcagccacc actgccgtct atgaggccat   2940
gactgcagtg gatactgagg ctgtgtggct gctccaaggc tggctcttcc agcaccagcc   3000
gcagttctgg gggcccgccc agatcagggc tgtgctggga gctgtgcccc gtggccgcct   3060
cctggttctg gacctgtttg ctgagagcca gcctgtgtat acccgcactg cctccttcca   3120
gggccagccc ttcatctggt gcatgctgca caactttggg ggaaaccatg gtctttttgg   3180
agccctagag gctgtgaacg gaggcccaga agctgcccgc ctcttcccca actccaccat   3240
ggtaggcacg ggcatggccc ccgagggcat cagccagaac gaagtggtct attccctcat   3300
ggctgagctg ggctggcgaa aggacccagt gccagatttg gcagcctggg tgaccagctt   3360
tgccgcccgg cggtatgggg tctcccaccc ggacgcaggg gcagcgtgga ggctactgct   3420
ccggagtgtg tacaactgct ccggggaggc ctgcaggggc cacaatcgta gcccgctggt   3480
caggcggccg tccctacaga tgaataccag catctggtac aaccgatctg atgtgtttga   3540
ggcctggcgg ctgctgctca catctgctcc ctccctggcc accagccccg ccttccgcta   3600
cgacctgctg gacctcactc ggcaggcagt gcaggagctg gtcagcttgt actatgagga   3660
ggcaagaagc gcctacctga gcaaggagct ggcctccctg ttgagggctg gaggcgtcct   3720
ggcctatgag ctgctgccgg cactggacga ggtgctggct agtgacagcc gcttcttgct   3780
gggcagctgg ctagagcagg cccgagcagc ggcagtcagt gaggccgagg ccgatttcta   3840
cgagcagaac agccgctacc agctgacctt gtgggggcca gaaggcaaca tcctggacta   3900
tgccaacaag cagctggcgg ggttggtggc caactactac acccctcgct ggcggctttt   3960
cctggaggcg ctggttgaca gtgtggccca gggcatccct ttccaacagc accagtttga   4020
caaaaatgtc ttccaactgg agcaggcctt cgttctcagc aagcagaggt accccagcca   4080
gccgcgagga gacactgtgg acctggccaa gaagatcttc ctcaaatatt acccccgctg   4140
ggtggccggc tcttggtgag aattcgagct cggtacccgg gaatcaattc actcctcagg   4200
tgcaggctgc ctatcagaag gtggtggctg gtgtggccaa tgccctggct cacaaatacc   4260
actgagatct tttccctct gccaaaaatt atggggacat catgaagccc cttgagcatc    4320
tgacttctgg ctaataaagg aaatttattt tcattgcaat agtgtgttgg aatttttgt    4380
gtctctcact cggaaggaca tatgggaggg caaatcattt aaaacatcag aatgagtatt   4440
tggtttagag tttggcaaca tatgcccata tgctggctgc catgaacaaa ggttggctat   4500
aaagaggtca tcagtatatg aaacagcccc ctgctgtcca ttccttattc catagaaaag   4560
ccttgacttg aggttagatt ttttttatat tttgttttgt gttatttttt tctttaacat   4620
ccctaaaatt ttccttacat gttttactag ccagattttt cctcctctcc tgactactcc   4680
cagtcatagc tgtccctctt ctcttatgga gatccctcga cctgcagccc aagctgtaga   4740
taagtagcat ggcgggttaa tcattaacta caaggaaccc ctagtgatgg agttggccac   4800
tccctctctg cgcgctcgct cgctcactga ggccgcccgg gctttgcccg ggcggcctca   4860
gtgagcgagc gagcgcgcag                                               4880
```

<210> SEQ ID NO 10
<211> LENGTH: 4886
<212> TYPE: DNA
<213> ORGANISM: Artificial Sequence
<220> FEATURE:
<223> OTHER INFORMATION: AAV9-CAG-cohNaGlu Nucleotide sequence

<400> SEQUENCE: 10

```
attacgccag ctgcgcgctc gctcgctcac tgaggccgcc cgggcaaagc ccgggcgtcg     60
ggcgaccttt ggtcgcccgg cctcagtgag cgagcgagcg cgcagagagg gagtggccaa    120
ctccatcact aggggttcct tgtagttaat gattaacccg ccatgctact tatctactcg    180
acattgatta ttgactagtt attaatagta atcaattacg gggtcattag ttcatagccc    240
atatatggag ttccgcgtta cataacttac ggtaaatggc ccgcctggct gaccgcccaa    300
cgacccccgc ccattgacgt caataatgac gtatgttccc atagtaacgc caatagggac    360
tttccattga cgtcaatggg tggagtattt acggtaaact gcccacttgg cagtacatca    420
agtgtatcat atgccaagta cgccccctat tgacgtcaat gacggtaaat ggcccgcctg    480
gcattatgcc cagtacatga ccttatggga ctttcctact tggcagtaca tctacgtatt    540
agtcatcgct attaccatgg tcgaggtgag ccccacgttc tgcttcactc tccccatctc    600
ccccccctcc ccacccccaa ttttgtattt atttattttt taattatttt gtgcagcgat    660
gggggcgggg gggggggggg ggcgcgcgcc aggcggggcg gggcggggcg aggggcgggg    720
cggggcgagg cggagaggtg cggcggcagc caatcagagc ggcgcgctcc gaaagtttcc    780
ttttatggcg aggcggcggc ggcggcggcc ctataaaaag cgaagcgcgc ggcgggcggg    840
agtcgctgcg ttgccttcgc cccgtgcccc gctccgccgc cgcctcgcgc cgcccgcccc    900
ggctctgact gaccgcgtta ctcccacagg tgagcgggcg ggacggccct tctcctccgg    960
gctgtaatta gcgcttggtt taatgacggc ttgtttcttt tctgtggctg cgtgaaagcc   1020
ttgaggggct ccgggagggc cctttgtgcg gggggagcgg ctcggggggt gcgtgcgtgt   1080
gtgtgtgcgt ggggagcgcc gcgtgcggct ccgcgctgcc cggcggctgt gagcgctgcg   1140
ggcgcggcgc ggggctttgt gcgctccgca gtgtgcgcga ggggagcgcg gccgggggcg   1200
gtgccccgcg gtgcgggggg ggctgcgagg ggaacaaagg ctgcgtgcgg ggtgtgtgcg   1260
tgggggggtg agcagggggt gtgggcgcgt cggtcgggct gcaacccccc ctgcaccccc   1320
ctccccgagt tgctgagcac ggcccggctt cgggtgcggg gctccgtacg gggcgtggcg   1380
cggggctcgc cgtgccgggc ggggggtggc ggcaggtggg ggtgccgggc ggggcggggc   1440
cgcctcgggc cggggagggc tcgggggagg ggcgcggcgg cccccggagc gccggcggct   1500
gtcgaggcgc ggcgagccgc agccattgcc ttttatggta atcgtgcgag agggcgcagg   1560
gacttccttt gtcccaaatc tgtgcggagc cgaaatctgg gaggcgccgc cgcaccccct   1620
ctagcgggcg cggggcgaag cggtgcggcg ccggcaggaa ggaaatgggc ggggagggcc   1680
ttcgtgcgtc gccgcgccgc cgtccccttc tccctctcca gcctcggggc tgtccgcggg   1740
gggacggctg ccttcggggg ggacggggca gggcggggtt cggcttctgg cgtgtgaccg   1800
gcggctctag agcctctgct aaccatgttc atgccttctt ctttttccta cagctcctgg   1860
gcaacgtgct ggttattgtg ctgtctcatc attttggcaa agaattgatt aattcgagcg   1920
aacgcgtgcc accatggaag ctgtggctgt ggcagctgct gtgggcgtgc tgctgctggc   1980
aggcgctggc ggagctgctg ggatgaagc tagagaagct gccgctgtgc gggccctggt   2040
ggctagactg ctgggacctg gacctgccgc cgacttctcc gtgtctgtgg aaagagccct   2100
ggccgccaag cctggcctgg acacatattc tctgggcgga ggcggcgctg ctcgcgtcag   2160
agtgcgagga tctacaggcg tggccgctgc tgccggactg cacagatacc tgagagactt   2220
ctgcggctgc catgtggctt ggagcggcag ccagctgaga ctgcctagac ctctgcctgc   2280
```

-continued

```
tgtgcctggc gagctgacag aggccacccc taacagatac cggtactacc agaacgtgtg   2340
cacccagagc tacagcttcg tgtggtggga ctgggccaga tgggagcgcg agatcgattg   2400
gatggccctg aacggcatca acctggccct ggcttggagt ggccaggaag ccatctggca   2460
gagagtgtac ctggctctgg gcctgaccca ggccgagatc aacgagttct ttaccggccc   2520
tgcctttctg gcctggggca gaatgggcaa cctgcacaca tgggacggcc ccctgcctcc   2580
tagctggcac atcaagcagc tgtacctgca gcacagagtg ctggaccaga tgagaagctt   2640
cggcatgacc cccgtgctgc ctgcttttgc tggacacgtg ccagaggccg tgaccagagt   2700
gttcccccaa gtgaacgtga ccaagatggg cagctggggc cacttcaact gcagctactc   2760
ctgcagcttc ctgctggccc ccgaggaccc catcttccct attatcggca gcctgttcct   2820
gcgggaactg atcaaagagt tcggcaccga ccacatctac ggcgccgaca ccttcaacga   2880
gatgcagccc cctagcagcg agccctctta cctggctgct gccaccacag ccgtgtacga   2940
ggccatgaca gccgtggata ccgaggccgt gtggctgctg cagggatggc tgtttcagca   3000
ccagccccag ttctggggcc ctgcccagat tagagcagtg ctgggcgctg tgcccagagg   3060
caggctgctg gtgctggatc tgttcgccga gagccagccc gtgtacacca gaaccgctag   3120
cttccaggga cagcccttca tctggtgcat gctgcacaac ttcggcggca accacggcct   3180
gttcggcgct ctggaagcag tgaatggcgg ccctgaggcc gccagactgt tccctaacag   3240
cacaatggtg ggaaccggca tggcccctga gggcatctct cagaacgagg tggtgtacag   3300
cctgatggcc gagctgggct ggcggaagga tcctgtgcct gatctggccg cctgggtcac   3360
aagcttcgcc gctagaagat acggcgtgtc ccaccctgat gctggcgccg cttggagact   3420
gctgctgaga agcgtgtaca actgctccgg cgaggcctgc aggggccaca acagatctcc   3480
actcgtgcgg aggcccagcc tgcagatgaa caccagcatc tggtacaatc ggagcgacgt   3540
gttcgaggcc tggcgcctgc tgctgacatc tgctcctagc ctggccacct cccccgcctt   3600
cagatacgat ctgctggacc tgaccaggca ggccgtgcag gaactggtgt ccctgtacta   3660
cgaggaagcc agaagcgcct acctgagcaa agagctggcc tccctgctga gagcaggggg   3720
agtgctggct tacgaactgc tgccagccct ggatgaggtg ctggctagcg actccagatt   3780
tctgctgggc tcctggctgg aacaggccag agctgccgca gtgtctgagg ccgaggccga   3840
tttctacgag cagaacagca gataccagct gaccctgtgg ggcccagagg gcaacatcct   3900
ggactacgcc aacaaacagc tggccggcct ggtggccaac tactacacac ctagatggcg   3960
gctgtttctg gaagctctgg tggactctgt ggcccagggc atcccattcc agcagcacca   4020
gttcgacaag aacgtgttcc agctggaaca ggctttcgtg ctgagcaagc agagataccc   4080
cagccagcct agaggcgaca cagtggacct ggccaagaag atctttctga agtactaccc   4140
cagatgggtg gccggctctt ggtgagaatt cgagctcggt acccgggaat caattcactc   4200
ctcaggtgca ggctgcctat cagaaggtgg tggctggtgt ggccaatgcc ctggctcaca   4260
aataccactg agatcttttt ccctctgcca aaaattatgg ggacatcatg aagccccttg   4320
agcatctgac ttctggctaa taaaggaaat ttattttcat tgcaatagtg tgttggaatt   4380
ttttgtgtct ctcactcgga aggacatatg ggagggcaaa tcatttaaaa catcagaatg   4440
agtatttggt ttagagtttg gcaacatatg cccatatgct ggctgccatg aacaaaggtt   4500
ggctataaag aggtcatcag tatatgaaac agccccctgc tgtccattcc ttattccata   4560
gaaaagcctt gacttgaggt tagatttttt ttatattttg ttttgtgtta ttttttcttt   4620
taacatccct aaaattttcc ttacatgttt tactagccag atttttcctc ctctcctgac   4680
```

```
tactcccagt catagctgtc cctcttctct tatggagatc cctcgacctg cagcccaagc   4740

tgtagataag tagcatggcg ggttaatcat taactacaag gaacccctag tgatggagtt   4800

ggccactccc tctctgcgcg ctcgctcgct cactgaggcc gcccgggctt tgcccgggcg   4860

gcctcagtga gcgagcgagc gcgcag                                        4886
```

<210> SEQ ID NO 11
<211> LENGTH: 4891
<212> TYPE: DNA
<213> ORGANISM: Artificial Sequence
<220> FEATURE:
<223> OTHER INFORMATION: AAV9-CAG-comNaGlu Nucleotide sequence

<400> SEQUENCE: 11

```
attacgccag ctgcgcgctc gctcgctcac tgaggccgcc cgggcaaagc ccgggcgtcg     60

ggcgaccttt ggtcgcccgg cctcagtgag cgagcgagcg cgcagagagg gagtggccaa    120

ctccatcact aggggttcct tgtagttaat gattaacccg ccatgctact tatctactcg    180

acattgatta ttgactagtt attaatagta atcaattacg gggtcattag ttcatagccc    240

atatatggag ttccgcgtta cataacttac ggtaaatggc ccgcctggct gaccgcccaa    300

cgacccccgc ccattgacgt caataatgac gtatgttccc atagtaacgc caatagggac    360

tttccattga cgtcaatggg tggagtattt acggtaaact gcccacttgg cagtacatca    420

agtgtatcat atgccaagta cgccccctat tgacgtcaat gacggtaaat ggcccgcctg    480

gcattatgcc cagtacatga ccttatggga ctttcctact tggcagtaca tctacgtatt    540

agtcatcgct attaccatgg tcgaggtgag ccccacgttc tgcttcactc tccccatctc    600

ccccccctcc ccacccccaa ttttgtattt atttattttt taattatttt gtgcagcgat    660

gggggcgggg gggggggggg ggcgcgcgcc aggcggggcg gggcggggcg aggggcgggg    720

cggggcgagg cggagaggtg cggcggcagc caatcagagc ggcgcgctcc gaaagtttcc    780

ttttatggcg aggcggcggc ggcggcggcc ctataaaaag cgaagcgcgc ggcgggcggg    840

agtcgctgcg ttgccttcgc cccgtgcccc gctccgccgc cgcctcgcgc cgcccgcccc    900

ggctctgact gaccgcgtta ctcccacagg tgagcgggcg ggacggccct tctcctccgg    960

gctgtaatta gcgcttggtt taatgacggc ttgtttcttt tctgtggctg cgtgaaagcc   1020

ttgaggggct ccgggagggc cctttgtgcg gggggagcgg ctcggggggt gcgtgcgtgt   1080

gtgtgtgcgt ggggagcgcc gcgtgcggct ccgcgctgcc cggcggctgt gagcgctgcg   1140

ggcgcggcgc ggggctttgt gcgctccgca gtgtgcgcga ggggagcgcg gccgggggcg   1200

gtgccccgcg gtgcgggggg ggctgcgagg ggaacaaagg ctgcgtgcgg ggtgtgtgcg   1260

tgggggggtg agcagggggt gtgggcgcgt cggtcgggct gcaacccccc ctgcaccccc   1320

ctccccgagt tgctgagcac ggcccggctt cgggtgcggg gctccgtacg gggcgtggcg   1380

cggggctcgc cgtgccgggc ggggggtggc ggcaggtggg ggtgccgggc ggggcggggc   1440

cgcctcgggc cggggagggc tcgggggagg ggcgcggcgg cccccggagc gccggcggct   1500

gtcgaggcgc ggcgagccgc agccattgcc ttttatggta atcgtgcgag agggcgcagg   1560

gacttccttt gtcccaaatc tgtgcggagc cgaaatctgg gaggcgccgc cgcaccccct   1620

ctagcgggcg cggggcgaag cggtgcggcg ccggcaggaa ggaaatgggc ggggagggcc   1680

ttcgtgcgtc gccgcgccgc cgtccccttc tccctctcca gcctcggggc tgtccgcggg   1740

gggacggctg ccttcggggg ggacggggca gggcggggtt cggcttctgg cgtgtgaccg   1800
```

-continued

```
gcggctctag agcctctgct aaccatgttc atgccttctt ctttttccta cagctcctgg   1860
gcaacgtgct ggttattgtg ctgtctcatc attttggcaa agaattgatt aattcgagcg   1920
aacgcgtgct agcgccacca tggaagctgc cggcctggcc gtgatcctgg gctttctgct   1980
gctggctggc ggctctgtgg gcgacgaggc cagagaagcc aaggctgtgc gcgagctggt   2040
cgtgcgcctg ctgggacctg gccctgccgc caacttcctg gtgtccgtgg aaagagccct   2100
ggccgacgag agcggcctgg acacatacag cctgtctggc ggcggaggcg tgccagttct   2160
ggtgcgcgga tctacaggcg tggccgctgc cgctggcctg cacagatacc tgagagactt   2220
ctgcggctgc caggtggcct ggtccagcgc tcagctgcat ctgccttggc cctgcctgc    2280
cgtgcctgac ggcctgaccg agacaacccc caacagatac cggtactacc agaacgtgtg   2340
cacccacagc tacagcttcg tctggtggga ctgggccaga tgggagcaag aaatcgactg   2400
gatggccctg aacggcatca acctggctct ggcctggaac ggccaagaag ccatctggca   2460
gagagtgtat ctggccctgg gcctgaccca gagcgagatc gacacctact tcaccggccc   2520
tgcctttctg gcttggggca gaatgggcaa cctgcacacc tgggacggcc ccctgcccag   2580
aagctggcac ctgagccagg tgtacctgca gcacagaatc ctggacagaa tgagaagctt   2640
cggcatgatc cccgtgctgc ccgccttcgc tggccacgtg cccaaggcca tcaccagagt   2700
gttcccccaa gtgaacgtga tcaagctggg cagctggggc cacttcaact gcagctactc   2760
ctgcagcttc ctgctggccc ctggcgaccc catgttcccc ctgatcggca acctgttcct   2820
gagagagctg accaaagagt tcggcaccga ccacatctac ggcgccgaca ccttcaacga   2880
gatgcagccc cccttcagcg acccctctta cctggccgcc accacagccg ccgtgtacga   2940
ggccatggtg acagtggacc ccgacgccgt gtggctgctg cagggctggc tgttccagca   3000
ccagccccag ttctggggac ctagccagat cagagccgtg ctggaagccg tgcccagagg   3060
cagactgctg gtgctggacc tgttcgccga gagccacccc gtgtacatgc acaccgccag   3120
cttccacggc cagcccttca tctggtgcat gctgcacaac ttcggcggca accacggcct   3180
gttcggcgcc ctggaagatg tgaacagagg cccccaggcc gccagactgt tccccaacag   3240
caccatggtc ggaaccggaa tcgcccccga gggcatcggc cagaacgagg tggtgtacgc   3300
cctgatggcc gagctgggct ggcggaagga ccctgtgcct gacctgatgg cctgggtgtc   3360
cagcttcgcc atcagacgct acggcgtgtc ccagcctgat gccgtggccg cttggaagct   3420
gctgctgaga agcgtgtaca actgcagcgg cgaggcctgc agcggccaca acagatcccc   3480
cctggtgaaa agacccagcc tgcagatgag caccgccgtg tggtacaacc gcagcgacgt   3540
gttcgaggcc tggcgcctgc tgctgacagc cgcccctaac ctgaccacct cccccgcctt   3600
cagatacgac ctgctggacg tgaccagaca ggccgtgcaa gaactggtgt ccctgtgcta   3660
cgaggaagcc agaaccgcct acctgaaaca agaactggac ctgctcctgc gggcaggcgg   3720
cctgctggtg tacaagctgc tgcccaccct ggacgagctg ctggccagct ctagccactt   3780
tctgctgggc acatggctgg accaggccag aaaggccgct gtgtctgagg ccgaggccca   3840
gttctacgag cagaacagca gataccagat caccctgtgg ggccctgagg gcaacatcct   3900
ggactacgcc aacaagcagc tggctggcct ggtggccgac tactaccagc ccagatggtg   3960
cctgttcctg ggcaccctgg cccacagcct ggctagaggc gtgcccttcc agcagcacga   4020
gttcgagaag aacgtgttcc ctctggaaca ggccttcgtg tacaacaaga agagataccc   4080
cagccagccc agaggcgaca ccgtggacct gagcaagaag atcttcctga agtaccaccc   4140
ccagcccgac agcctgtgat gagcggccgc gaattcgagc tcggtacccg ggaatcaatt   4200
```

```
cactcctcag gtgcaggctg cctatcagaa ggtggtggct ggtgtggcca atgccctggc   4260

tcacaaatac cactgagatc tttttccctc tgccaaaaat tatggggaca tcatgaagcc   4320

ccttgagcat ctgacttctg gctaataaag gaaatttatt ttcattgcaa tagtgtgttg   4380

gaattttttg tgtctctcac tcggaaggac atatgggagg gcaaatcatt taaaacatca   4440

gaatgagtat ttggtttaga gtttggcaac atatgcccat atgctggctg ccatgaacaa   4500

aggttggcta taaagaggtc atcagtatat gaaacagccc cctgctgtcc attccttatt   4560

ccatagaaaa gccttgactt gaggttagat ttttttata ttttgttttg tgttattttt   4620

ttctttaaca tccctaaaat ttttccttaca tgttttacta gccagatttt tcctcctctc   4680

ctgactactc ccagtcatag ctgtccctct tctcttatgg agatccctcg acctgcagcc   4740

caagctgtag ataagtagca tggcgggtta atcattaact acaaggaacc cctagtgatg   4800

gagttggcca ctccctctct gcgcgctcgc tcgctcactg aggccgcccg ggctttgccc   4860

gggcggcctc agtgagcgag cgagcgcgca g                                  4891
```

<210> SEQ ID NO 12
<211> LENGTH: 4898
<212> TYPE: DNA
<213> ORGANISM: Artificial Sequence
<220> FEATURE:
<223> OTHER INFORMATION: AAV9-CAG-cocNaGlu Nucleotide sequence

<400> SEQUENCE: 12

```
attacgccag ctgcgcgctc gctcgctcac tgaggccgcc cgggcaaagc ccgggcgtcg     60

ggcgaccttt ggtcgcccgg cctcagtgag cgagcgagcg cgcagagagg gagtggccaa    120

ctccatcact aggggttcct tgtagttaat gattaacccg ccatgctact tatctactcg    180

acattgatta ttgactagtt attaatagta atcaattacg gggtcattag ttcatagccc    240

atatatggag ttccgcgtta cataacttac ggtaaatggc ccgcctggct gaccgcccaa    300

cgacccccgc ccattgacgt caataatgac gtatgttccc atagtaacgc caatagggac    360

tttccattga cgtcaatggg tggagtattt acggtaaact gcccacttgg cagtacatca    420

agtgtatcat atgccaagta cgccccctat tgacgtcaat gacggtaaat ggcccgcctg    480

gcattatgcc cagtacatga ccttatggga ctttcctact tggcagtaca tctacgtatt    540

agtcatcgct attaccatgg tcgaggtgag ccccacgttc tgcttcactc tccccatctc    600

ccccccctcc ccacccccaa ttttgtattt atttattttt taattatttt gtgcagcgat    660

gggggcgggg gggggggggg ggcgcgcgcc aggcggggcg gggcggggcg aggggcgggg    720

cggggcgagg cggagaggtg cggcggcagc caatcagagc ggcgcgctcc gaaagtttcc    780

ttttatggcg aggcggcggc ggcggcggcc ctataaaaag cgaagcgcgc ggcgggcggg    840

agtcgctgcg ttgccttcgc cccgtgcccc gctccgccgc cgcctcgcgc cgcccgcccc    900

ggctctgact gaccgcgtta ctcccacagg tgagcgggcg ggacggccct tctcctccgg    960

gctgtaatta gcgcttggtt taatgacggc ttgtttcttt tctgtggctg cgtgaaagcc   1020

ttgaggggct ccgggagggc cctttgtgcg gggggagcgg ctcggggggt gcgtgcgtgt   1080

gtgtgtgcgt ggggagcgcc gcgtgcggct ccgcgctgcc cggcggctgt gagcgctgcg   1140

ggcgcggcgc ggggctttgt gcgctccgca gtgtgcgcga ggggagcgcg gccgggggcg   1200

gtgccccgcg gtgcgggggg ggctgcgagg ggaacaaagg ctgcgtgcgg ggtgtgtgcg   1260

tggggggtg agcagggggt gtgggcgcgt cggtcgggct gcaacccccc ctgcaccccc   1320
```

-continued

```
ctccccgagt tgctgagcac ggcccggctt cgggtgcggg gctccgtacg gggcgtggcg   1380

cggggctcgc cgtgccgggc ggggggtggc ggcaggtggg ggtgccgggc ggggcggggc   1440

cgcctcgggc cggggagggc tcgggggagg ggcgcggcgg cccccggagc gccggcggct   1500

gtcgaggcgc ggcgagccgc agccattgcc ttttatggta atcgtgcgag agggcgcagg   1560

gacttccttt gtcccaaatc tgtgcggagc cgaaatctgg gaggcgccgc cgcacccct    1620

ctagcgggcg cggggcgaag cggtgcggcg ccggcaggaa ggaaatgggc ggggagggcc   1680

ttcgtgcgtc gccgcgccgc cgtccccttc tccctctcca gcctcggggc tgtccgcggg   1740

gggacggctg ccttcggggg ggacggggca gggcggggtt cggcttctgg cgtgtgaccg   1800

gcggctctag agcctctgct aaccatgttc atgccttctt ctttttccta cagctcctgg   1860

gcaacgtgct ggttattgtg ctgtctcatc attttggcaa agaattgatt aattcgagcg   1920

aacgcgtgcc accatgggag ctgccgctgc tgctgctgtc ctgggcctcc tgctcctggg   1980

agctgctggc ggagccgccg ctgatgaagc cagagaagcc gctgccgtgc gggctctgct   2040

cgtcagactg ctgggacctg gacccgcagc tgccttcagc gtgtccgtga aaagagccct   2100

ggccgccgag agcggcctgg acacctatag actgtctggc ggcggagccg gcaccagggt   2160

gctggtgctg ggatctacag gtgtcgccgc tgccgccgga ctgcacagat acctgaggga   2220

cttctgcggc tgccatgtgg cttggagcgg cagccagctg agactgcctg agcctctgcc   2280

tgccgtgcct caggtgctga ccgaggccac ccccaacaga taccggtact accagaacgt   2340

gtgcacccac agctacagct tcgtctggtg ggactgggcc agatgggagc gcgagctgga   2400

ctggatggcc ctgaacggca tcaacctggc tctcgcttgg agtggccagg aagccatctg   2460

gcagagggtg tacctggccc tgggcctgac ccagagcgag atcgacgagt acttcaccgg   2520

ccctgccttt ctggcctggg gcaggatggg caacctgcac acctggggcg gacccctgcc   2580

tcacagctgg cacctgaagc agctgtacct gcagcacagg atcctggaca ggatgcggag   2640

cttcggcatg atccccgtgc tgcccgcctt cagcggccac gtgccaaagg ccctgaccag   2700

ggtgttcccc cagatcaaca tcacacagct cggaagttgg ggccacttca actgcagcta   2760

ctcctgcagc ttcctgctgg cccccgagga cccccctgttc cctatcatcg gcagcctgtt   2820

tctgagagag ctgatccagg aatttggcac caaccacatc tacggcgccg acaccttcaa   2880

cgagatgcag ccccccagca gcgagcccag ctacctggcc tctgccaccg ccagcgtgta   2940

ccaggccatg atcaccgtgg acagcgacgc cgtgtggctg ctgcagggct ggctgttcca   3000

gcaccagcct cagttctggg gccctgccca ggtcaaagcc gtgctggaag ccgtgcccag   3060

gggcaggctg ctcgtgctgg atctgttcgc cgagagccag cccgtgtaca tccagaccgc   3120

cagcttccag ggccagccct tcatctggtg catgctgcac aacttcggcg gcaaccacgg   3180

cctgttcgga gccctcgagg ccgtgaatag aggcccagcc gccgctaggc tgttccccaa   3240

ctctaccatg ctgggcaccg gaatggcccc tgagggcatc ggccagaacg aggtggtgta   3300

cgccctgatg gccgagctgg gctggcggaa ggatcccgtg gccgatctgg aagcctgggt   3360

gtccagcttc gccgctcgga gatacggcgt ggcccacaga gataccgaag ccgcctggag   3420

actgctgctg agaagcgtgt acaactgcag cggcgaggcc tgctccggcc acaacagatc   3480

tccactcgtg cggaggccct ccctgcagat ggtcaccacc gtgtggtata accgcagcga   3540

cgtgttcgag gcttggagac tgctgctgac cgccgctcct accctggcca gcagccccac   3600

cttcagatac gacctgctgg acgtgaccag gcaggccgcc caggaactcg tcagcctgta   3660

ctacgtggaa gccagaagcg cctacctgcg gaaagaactg gtgcccctgc tgagggccgc   3720
```

```
tggcgtgctg gtgtatgagc tgctgcctgc cctggacaag gtgctggcta gcgactcccg   3780

gttcctgctg ggcagatggc tggaacaggc cagggctgcc gccgtgtctg aagccgaggc   3840

ccacctgtac gagcagaaca gcagatacca gctgaccctg tggggacccg agggcaacat   3900

cctggactac gccaacaagc agctggccgg cctggtggcc gactactaca cccccagatg   3960

gcggctgttc atggaaatgc tggtggaaag cctggtgcag ggcatcccat tccagcagca   4020

ccagttcgac aagaacgcct tccagctcga gcagaccttc atcttcggca cccagagata   4080

ccccagccag cccgacggcg acaccgtgga cctggccaag aagctgttca tcaagtacta   4140

ccccaggctg gtggccggct ccctgtgggc cgattgagaa ttcgagctcg gtacccggga   4200

atcaattcac tcctcaggtg caggctgcct atcagaaggt ggtggctggt gtggccaatg   4260

ccctggctca caaataccac tgagatcttt ttccctctgc caaaaattat ggggacatca   4320

tgaagcccct tgagcatctg acttctggct aataaaggaa atttattttc attgcaatag   4380

tgtgttggaa ttttttgtgt ctctcactcg gaaggacata tgggagggca aatcatttaa   4440

aacatcagaa tgagtatttg gtttagagtt tggcaacata tgcccatatg ctggctgcca   4500

tgaacaaagg ttggctataa agaggtcatc agtatatgaa acagcccct gctgtccatt   4560

ccttattcca tagaaaagcc ttgacttgag gttagatttt ttttatattt tgttttgtgt   4620

tatttttttc tttaacatcc ctaaaatttt ccttacatgt tttactagcc agatttttcc   4680

tcctctcctg actactccca gtcatagctg tccctcttct cttatggaga tccctcgacc   4740

tgcagcccaa gctgtagata agtagcatgg cgggttaatc attaactaca aggaacccct   4800

agtgatggag ttggccactc cctctctgcg cgctcgctcg ctcactgagg ccgcccgggc   4860

tttgcccggg cggcctcagt gagcgagcga gcgcgcag                          4898
```

<210> SEQ ID NO 13
<211> LENGTH: 20
<212> TYPE: DNA
<213> ORGANISM: Artificial Sequence
<220> FEATURE:
<223> OTHER INFORMATION: Forward primer for genotyping

<400> SEQUENCE: 13

```
gtcgtctcct ggttctggac                                                20
```

<210> SEQ ID NO 14
<211> LENGTH: 20
<212> TYPE: DNA
<213> ORGANISM: Artificial Sequence
<220> FEATURE:
<223> OTHER INFORMATION: Reverse primer for genotyping

<400> SEQUENCE: 14

```
accacttcat tctggccaat                                                20
```

<210> SEQ ID NO 15
<211> LENGTH: 18
<212> TYPE: DNA
<213> ORGANISM: Artificial Sequence
<220> FEATURE:
<223> OTHER INFORMATION: Reverse primer mutation for genotyping

<400> SEQUENCE: 15

```
cgctttctgg gctcagag                                                  18
```

<210> SEQ ID NO 16

<211> LENGTH: 18
<212> TYPE: DNA
<213> ORGANISM: Artificial Sequence
<220> FEATURE:
<223> OTHER INFORMATION: Forward primer for quantification

<400> SEQUENCE: 16
gccgaggccc agttctac 18

<210> SEQ ID NO 17
<211> LENGTH: 21
<212> TYPE: DNA
<213> ORGANISM: Artificial Sequence
<220> FEATURE:
<223> OTHER INFORMATION: Reverse primer for quantification

<400> SEQUENCE: 17
ttggcgtagt ccaggatgtt g 21

<210> SEQ ID NO 18
<211> LENGTH: 27
<212> TYPE: DNA
<213> ORGANISM: Artificial Sequence
<220> FEATURE:
<223> OTHER INFORMATION: Probe for quantification

<400> SEQUENCE: 18
agcagaacag cagataccag atcaccc 27

<210> SEQ ID NO 19
<211> LENGTH: 2244
<212> TYPE: DNA
<213> ORGANISM: Artificial Sequence
<220> FEATURE:
<223> OTHER INFORMATION: cohNaglu-version2 CDS sequence

<400> SEQUENCE: 19
cgcgtgccac catggaagca gtcgccgtcg ccgcagcagt gggtgtcctc ctcctcgccg 60
gtgctggagg tgccgccggg gacgaggccc gcgaggccgc agctgtgcgg gcccttgtgg 120
cccggcttct cggaccgggc cctgccgccg acttcagcgt gtcagtggaa cgcgcactgg 180
ctgcgaagcc tgggctcgat acttactccc tgggcggggg tggtgccgcc agagtgcggg 240
tccggggaag caccggggtg gccgccgcgg ccggcctgca ccggtacctt cgggactttt 300
gcggctgtca tgtcgcttgg tccggatccc agctgcgcct cccccgaccg ctgcccgccg 360
tgcctggaga gctgaccgag gccactccga accggtacag atactatcag aacgtgtgca 420
ctcagtccta ctccttcgtg tggtgggact gggccagatg ggagcgggag attgactgga 480
tggccctgaa cggtatcaac ctcgccttgg cctggtccgg ccaggaggcc atttggcaga 540
gggtgtacct tgcactggga ctgactcaag ccgagatcaa cgagtttttc accggccccg 600
ctttccttgc ctgggggcgc atgggcaacc tccacacctg ggacgggcct ctgccgccct 660
cctggcatat caagcagctg tacctccagc acagggtgct tgaccagatg cggagctttg 720
gaatgacccc tgtgctgccc gcgttcgcgg gtcacgtgcc agaagcagtg actcgcgtgt 780
tcccccaagt gaacgtcacc aaaatgggat cgtggggaca ctttaactgc tcttattcct 840
gctccttcct cttggcgccg gaggacccga tcttcccgat tattggatcg ctgttcctgc 900
gggagctgat caaggagttc ggaaccgacc acatctacgg cgctgacacc ttcaacgaga 960
tgcagccgcc ttcctccgaa ccatcgtacc tcgcggccgc tactactgcg gtgtacgagg 1020
ccatgaccgc agtggatacc gaagccgtct ggctgctgca agggtggttg ttccagcacc 1080

```
agccgcagtt ttggggaccc gcccagattc gcgccgtgct gggcgccgtg cctaggggtc   1140
gcctgctcgt gctggacctg ttcgccgagt cccagccagt gtacactagg accgcgtcgt   1200
tccaaggaca gcccttcatt tggtgtatgc ttcacaactt cgggggcaac cacggtctgt   1260
tcggagcctt ggaagccgtg aatggcggtc ccgaggcagc gcggcttttc cccaactcaa   1320
ccatggtcgg aaccggaatg gcccctgaag gaatctccca gaacgaagtc gtgtactcgc   1380
tgatggcaga gctgggctgg cggaaggatc ctgtccctga tctcgccgcc tgggtgacat   1440
ccttcgccgc tcgccgctat ggtgtctccc atccggatgc cggagccgca tggaggctgc   1500
tgctgagatc cgtgtacaac tgctcgggag aagcgtgtcg gggacataac aggtccccac   1560
tcgtgcgcag accgagcctg cagatgaaca cctccatctg gtacaaccgg tccgacgtgt   1620
tcgaagcgtg gagactgctg ctgacttccg ccccgagcct cgcgaccagc ccggcgttcc   1680
gctacgatct cctggacctc acaagacagg cggtccaaga actggtgtcc ctgtactacg   1740
aagaggcccg ctccgcatac ctcagcaagg aactcgcatc gttgctgagg gccggcggag   1800
tgctggcata cgagctgctg ccggccctgg acgaagtgct ggccagcgac agccggttcc   1860
tgctgggctc ttggctggaa caggcccgcg ctgctgcggt gtccgaagcc gaagcggact   1920
tctacgagca gaactcacgg taccaactga ccctctgggg tccggagggc aacattctgg   1980
actacgccaa caagcaactc gccggcctgg tcgcaaatta ctatactcct cggtggaggc   2040
tgttcctgga agcgctggtc gattcagtgg ctcaggggat cccattccaa cagcaccaat   2100
tcgacaagaa cgtgttccag cttgagcagg cctttgtgtt gtcgaagcag cgctacccca   2160
gccagccacg ggagacacg gtggacctgg ccaagaagat cttcctgaaa tactacccaa   2220
gatgggtggc cggctcgtgg tagg                                          2244
```

<210> SEQ ID NO 20
<211> LENGTH: 8467
<212> TYPE: DNA
<213> ORGANISM: Artificial Sequence
<220> FEATURE:
<223> OTHER INFORMATION: pAAV-CAG-cohNaglu-version2 sequence

<400> SEQUENCE: 20

```
gggcgatcgg tgcgggcctc ttcgctatta cgccagctgc gcgctcgctc gctcactgag     60
gccgcccggg caaagcccgg gcgtcgggcg acctttggtc gcccggcctc agtgagcgag    120
cgagcgcgca gagagggagt ggccaactcc atcactaggg gttccttgta gttaatgatt    180
aacccgccat gctacttatc tactcgacat tgattattga ctagttatta atagtaatca    240
attacggggt cattagttca tagcccatat atggagttcc gcgttacata acttacggta    300
aatggcccgc ctggctgacc gcccaacgac ccccgcccat tgacgtcaat aatgacgtat    360
gttcccatag taacgccaat agggactttc cattgacgtc aatgggtgga gtatttacgg    420
taaactgccc acttggcagt acatcaagtg tatcatatgc caagtacgcc ccctattgac    480
gtcaatgacg gtaaatggcc cgcctggcat tatgcccagt acatgacctt atgggacttt    540
cctacttggc agtacatcta cgtattagtc atcgctatta ccatggtcga ggtgagcccc    600
acgttctgct tcactctccc catctccccc ccctccccac ccccaatttt gtatttattt    660
atttttaat tattttgtgc agcgatgggg gcgggggggg ggggggggcg cgcgccaggc    720
ggggcggggc ggggcgaggg gcggggcggg gcgaggcgga gaggtgcggc ggcagccaat    780
cagagcggcg cgctccgaaa gtttcctttt atggcgaggc ggcggcggcg gcggccctat    840
```

-continued

```
aaaaagcgaa gcgcgcggcg ggcgggagtc gctgcgttgc cttcgccccg tgccccgctc    900
cgccgccgcc tcgcgccgcc cgccccggct ctgactgacc gcgttactcc cacaggtgag    960
cgggcgggac ggcccttctc ctccgggctg taattagcgc ttggtttaat gacggcttgt   1020
ttcttttctg tggctgcgtg aaagccttga ggggctccgg gagggccctt tgtgcggggg   1080
gagcggctcg gggggtgcgt gcgtgtgtgt gtgcgtgggg agcgccgcgt gcggctccgc   1140
gctgcccggc ggctgtgagc gctgcgggcg cggcgcgggg ctttgtgcgc tccgcagtgt   1200
gcgcgagggg agcgcggccg gggcggtgc cccgcggtgc ggggggggct gcgaggggaa   1260
caaaggctgc gtgcggggtg tgtgcgtggg ggggtgagca gggggtgtgg gcgcgtcggt   1320
cgggctgcaa ccccccctgc acccccctcc ccgagttgct gagcacggcc cggcttcggg   1380
tgcggggctc cgtacggggc gtggcgcggg gctcgccgtg ccgggcgggg ggtggcggca   1440
ggtgggggtg ccgggcgggg cggggccgcc tcgggccggg gagggctcgg gggaggggcg   1500
cggcggcccc cggagcgccg gcggctgtcg aggcgcggcg agccgcagcc attgcctttt   1560
atggtaatcg tgcgagaggg cgcagggact tcctttgtcc caaatctgtg cggagccgaa   1620
atctgggagg cgccgccgca ccccctctag cgggcgcggg gcgaagcggt gcggcgccgg   1680
caggaaggaa atgggcgggg agggccttcg tgcgtcgccg cgccgccgtc cccttctccc   1740
tctccagcct cggggctgtc cgcgggggga cggctgcctt cggggggac ggggcagggc   1800
ggggttcggc ttctggcgtg tgaccggcgg ctctagagcc tctgctaacc atgttcatgc   1860
cttcttcttt ttcctacagc tcctgggcaa cgtgctggtt attgtgctgt ctcatcattt   1920
tggcaaagaa ttgattaatt cgagcgaacg cgtgccacca tggaagcagt cgccgtcgcc   1980
gcagcagtgg gtgtcctcct cctcgccggt gctggaggtg ccgccgggga cgaggcccgc   2040
gaggccgcag ctgtgcgggc ccttgtggcc cggcttctcg gaccgggccc tgccgccgac   2100
ttcagcgtgt cagtggaacg cgcactggct gcgaagcctg ggctcgatac ttactccctg   2160
ggcgggggtg gtgccgccag agtgcgggtc cggggaagca ccggggtggc cgccgcggcc   2220
ggcctgcacc ggtaccttcg ggacttttgc ggctgtcatg tcgcttggtc cggatcccag   2280
ctgcgcctcc cccgaccgct gcccgccgtg cctggagagc tgaccgaggc cactccgaac   2340
cggtacagat actatcagaa cgtgtgcact cagtcctact ccttcgtgtg gtgggactgg   2400
gccagatggg agcgggagat tgactggatg gccctgaacg gtatcaacct cgccttggcc   2460
tggtccggcc aggaggccat ttggcagagg gtgtaccttg cactgggact gactcaagcc   2520
gagatcaacg agtttttcac cggccccgct ttccttgcct gggggcgcat gggcaacctc   2580
cacacctggg acgggcctct gccgccctcc tggcatatca agcagctgta cctccagcac   2640
agggtgcttg accagatgcg gagctttgga atgacccctg tgctgcccgc gttcgcgggt   2700
cacgtgccag aagcagtgac tcgcgtgttc cccccaagtga acgtcaccaa aatgggatcg   2760
tggggacact ttaactgctc ttattcctgc tccttcctct tggcgccgga ggacccgatc   2820
ttcccgatta ttggatcgct gttcctgcgg gagctgatca aggagttcgg aaccgaccac   2880
atctacggcg ctgacacctt caacgagatg cagccgcctt cctccgaacc atcgtacctc   2940
gcggccgcta ctactgcggt gtacgaggcc atgaccgcag tggataccga agccgtctgg   3000
ctgctgcaag ggtggttgtt ccagcaccag ccgcagtttt ggggacccgc ccagattcgc   3060
gccgtgctgg gcgccgtgcc taggggtcgc ctgctcgtgc tggacctgtt cgccgagtcc   3120
cagccagtgt acactaggac cgcgtcgttc caaggacagc ccttcatttg gtgtatgctt   3180
cacaacttcg gggcaacca cggtctgttc ggagccttgg aagccgtgaa tggcggtccc   3240
```

```
gaggcagcgc ggcttttccc caactcaacc atggtcggaa ccggaatggc ccctgaagga   3300

atctcccaga acgaagtcgt gtactcgctg atggcagagc tgggctggcg gaaggatcct   3360

gtccctgatc tcgccgcctg ggtgacatcc ttcgccgctc gccgctatgg tgtctcccat   3420

ccggatgccg gagccgcatg gaggctgctg ctgagatccg tgtacaactg ctcgggagaa   3480

gcgtgtcggg gacataacag gtccccactc gtgcgcagac cgagcctgca gatgaacacc   3540

tccatctggt acaaccggtc cgacgtgttc gaagcgtgga gactgctgct gacttccgcc   3600

ccgagcctcg cgaccagccc ggcgttccgc tacgatctcc tggacctcac aagacaggcg   3660

gtccaagaac tggtgtccct gtactacgaa gaggcccgct ccgcatacct cagcaaggaa   3720

ctcgcatcgt tgctgagggc cggcggagtg ctggcatacg agctgctgcc ggccctggac   3780

gaagtgctgg ccagcgacag ccggttcctg ctgggctctt ggctggaaca ggcccgcgct   3840

gctgcggtgt ccgaagccga agcggacttc tacgagcaga actcacggta ccaactgacc   3900

ctctggggtc cggagggcaa cattctggac tacgccaaca agcaactcgc cggcctggtc   3960

gcaaattact atactcctcg gtggaggctg ttcctggaag cgctggtcga ttcagtggct   4020

caggggatcc cattccaaca gcaccaattc gacaagaacg tgttccagct tgagcaggcc   4080

tttgtgttgt cgaagcagcg ctaccccagc cagccacggg gagacacggt ggacctggcc   4140

aagaagatct tcctgaaata ctacccaaga tgggtggccg gctcgtggta ggaattcgag   4200

ctcggtaccc gggaatcaat tcactcctca ggtgcaggct gcctatcaga aggtggtggc   4260

tggtgtggcc aatgccctgg ctcacaaata ccactgagat ctttttccct ctgccaaaaa   4320

ttatggggac atcatgaagc cccttgagca tctgacttct ggctaataaa ggaaatttat   4380

tttcattgca atagtgtgtt ggaatttttt gtgtctctca ctcggaagga catatgggag   4440

ggcaaatcat ttaaaacatc agaatgagta tttggtttag agtttggcaa catatgccca   4500

tatgctggct gccatgaaca aaggttggct ataaagaggt catcagtata tgaaacagcc   4560

ccctgctgtc cattccttat tccatagaaa agccttgact tgaggttaga ttttttttat   4620

attttgtttt gtgttatttt tttctttaac atccctaaaa ttttccttac atgttttact   4680

agccagattt ttcctcctct cctgactact cccagtcata gctgtccctc ttctcttatg   4740

gagatccctc gacctgcagc ccaagctgta gataagtagc atggcgggtt aatcattaac   4800

tacaaggaac ccctagtgat ggagttggcc actccctctc tgcgcgctcg ctcgctcact   4860

gaggccgccc gggctttgcc cgggcggcct cagtgagcga gcgagcgcgc agctgcatta   4920

atgaatcggc caacgcgcgg ggagaggcgg tttgcgtatt gggcgctctt ccgcttcctc   4980

gctcactgac tcgctgcgct cggtcgttcg gctgcggcga gcggtatcag ctcactcaaa   5040

ggcggtaata cggttatcca cagaatcagg ggataacgca ggaaagaaca tgtgagcaaa   5100

aggccagcaa aaggccagga accgtaaaaa ggccgcgttg ctggcgtttt tccataggct   5160

ccgcccccct gacgagcatc acaaaaatcg acgctcaagt cagaggtggc gaaacccgac   5220

aggactataa agataccagg cgtttccccc tggaagctcc ctcgtgcgct ctcctgttcc   5280

gaccctgccg cttaccggat acctgtccgc ctttctccct tcgggaagcg tggcgctttc   5340

tcatagctca cgctgtaggt atctcagttc ggtgtaggtc gttcgctcca agctgggctg   5400

tgtgcacgaa ccccccgttc agcccgaccg ctgcgcctta tccggtaact atcgtcttga   5460

gtccaacccg gtaagacacg acttatcgcc actggcagca gccactggta acaggattag   5520

cagagcgagg tatgtaggcg gtgctacaga gttcttgaag tggtggccta actacggcta   5580
```

```
cactagaaga acagtatttg gtatctgcgc tctgctgaag ccagttacct tcggaaaaag   5640

agttggtagc tcttgatccg gcaaacaaac caccgctggt agcggtggtt tttttgtttg   5700

caagcagcag attacgcgca gaaaaaaagg atctcaagaa gatcctttga tcttttctac   5760

ggggtctgac gctcagtgga acgaaaactc acgttaaggg attttggtca tgagattatc   5820

aaaaaggatc ttcacctaga tccttttaaa ttaaaaatga agttttaaat caatctaaag   5880

tatatatgag taaacttggt ctgacagtta ccaatgctta atcagtgagg cacctatctc   5940

agcgatctgt ctatttcgtt catccatagt tgcctgactc cccgtcgtgt agataactac   6000

gatacgggag ggcttaccat ctggccccag tgctgcaatg ataccgcgag acccacgctc   6060

accggctcca gatttatcag caataaacca gccagccgga agggccgagc gcagaagtgg   6120

tcctgcaact ttatccgcct ccatccagtc tattaattgt tgccgggaag ctagagtaag   6180

tagttcgcca gttaatagtt tgcgcaacgt tgttgccatt gctacaggca tcgtggtgtc   6240

acgctcgtcg tttggtatgg cttcattcag ctccggttcc caacgatcaa ggcgagttac   6300

atgatccccc atgttgtgca aaaaagcggt tagctccttc ggtcctccga tcgttgtcag   6360

aagtaagttg gccgcagtgt tatcactcat ggttatggca gcactgcata attctcttac   6420

tgtcatgcca tccgtaagat gcttttctgt gactggtgag tactcaacca agtcattctg   6480

agaatagtgt atgcggcgac cgagttgctc ttgcccggcg tcaatacggg ataataccgc   6540

gccacatagc agaactttaa aagtgctcat cattggaaaa cgttcttcgg ggcgaaaact   6600

ctcaaggatc ttaccgctgt tgagatccag ttcgatgtaa cccactcgtg cacccaactg   6660

atcttcagca tcttttactt tcaccagcgt ttctgggtga gcaaaaacag gaaggcaaaa   6720

tgccgcaaaa aagggaataa gggcgacacg gaaatgttga atactcatac tcttcctttt   6780

tcaatattat tgaagcattt atcagggtta ttgtctcatg agcggataca tatttgaatg   6840

tatttagaaa aataaacaaa taggggttcc gcgcacattt ccccgaaaag tgccacctga   6900

cgtctaagaa accattatta tcatgacatt aacctataaa aataggcgta tcacgaggcc   6960

ctttcgtctc gcgcgtttcg gtgatgacgg tgaaaacctc tgacacatgc agctcccgga   7020

gacggtcaca gcttgtctgt aagcggatgc cgggagcaga caagcccgtc agggcgcgtc   7080

agcgggtgtt ggcgggtgtc ggggctggct taactatgcg gcatcagagc agattgtact   7140

gagagtgcac catatgcggt gtgaaatacc gcacagatgc gtaaggagaa aataccgcat   7200

caggcgattc caacatccaa taaatcatac aggcaaggca aagaattagc aaaattaagc   7260

aataaagcct cagagcataa agctaaatcg gttgtaccaa aaacattatg accctgtaat   7320

acttttgcgg gagaagcctt tatttcaacg caaggataaa aatttttaga accctcatat   7380

attttaaatg caatgcctga gtaatgtgta ggtaaagatt caaacgggtg agaaaggccg   7440

gagacagtca aatcaccatc aatatgatat tcaaccgttc tagctgataa attcatgccg   7500

gagagggtag ctatttttga gaggtctcta caaaggctat caggtcattg cctgagagtc   7560

tggagcaaac aagagaatcg atgaacggta atcgtaaaac tagcatgtca atcatatgta   7620

ccccggttga taatcagaaa agccccaaaa acaggaagat tgtataagca aatatttaaa   7680

ttgtaagcgt taatattttg ttaaaattcg cgttaaattt ttgttaaatc agctcatttt   7740

ttaaccaata ggccgaaatc ggcaaaatcc cttataaatc aaaagaatag accgagatag   7800

ggttgagtgt tgttccagtt tggaacaaga gtccactatt aaagaacgtg gactccaacg   7860

tcaaagggcg aaaaaccgtc tatcagggcg atggcccact acgtgaacca tcaccctaat   7920

caagtttttt ggggtcgagg tgccgtaaag cactaaatcg gaaccctaaa gggagccccc   7980
```

```
gatttagagc ttgacgggga aagccggcga acgtggcgag aaaggaaggg aagaaagcga   8040

aaggagcggg cgctagggcg ctggcaagtg tagcggtcac gctgcgcgta accaccacac   8100

ccgccgcgct taatgcgccg ctacagggcg cgtactatgg ttgctttgac gagcacgtat   8160

aacgtgcttt cctcgttaga atcagagcgg gagctaaaca ggaggccgat taaagggatt   8220

ttagacagga acggtacgcc agaatcctga gaagtgtttt tataatcagt gaggccaccg   8280

agtaaaagag tctgtccatc acgcaaatta accgttgtcg caatacttct ttgattagta   8340

ataacatcac ttgcctgagt agaagaactc aaactatcgg ccttgctggt aatatccaga   8400

acaatattac cgccagccat tgcaacggaa tcgccattcg ccattcaggc tgcgcaactg   8460

ttgggaa                                                              8467
```

<210> SEQ ID NO 21
<211> LENGTH: 4886
<212> TYPE: DNA
<213> ORGANISM: Artificial Sequence
<220> FEATURE:
<223> OTHER INFORMATION: AAV9-CAG-cohNaglu-version2 sequence

<400> SEQUENCE: 21

```
attacgccag ctgcgcgctc gctcgctcac tgaggccgcc cgggcaaagc ccgggcgtcg     60

ggcgaccttt ggtcgcccgg cctcagtgag cgagcgagcg cgcagagagg gagtggccaa    120

ctccatcact aggggttcct tgtagttaat gattaacccg ccatgctact tatctactcg    180

acattgatta ttgactagtt attaatagta atcaattacg gggtcattag ttcatagccc    240

atatatggag ttccgcgtta cataacttac ggtaaatggc ccgcctggct gaccgcccaa    300

cgacccccgc ccattgacgt caataatgac gtatgttccc atagtaacgc caatagggac    360

tttccattga cgtcaatggg tggagtattt acggtaaact gcccacttgg cagtacatca    420

agtgtatcat atgccaagta cgccccctat tgacgtcaat gacggtaaat ggcccgcctg    480

gcattatgcc cagtacatga ccttatggga ctttcctact tggcagtaca tctacgtatt    540

agtcatcgct attaccatgg tcgaggtgag ccccacgttc tgcttcactc tccccatctc    600

ccccccctcc ccacccccaa ttttgtattt atttattttt taattatttt gtgcagcgat    660

gggggcgggg gggggggggg ggcgcgcgcc aggcggggcg gggcggggcg aggggcgggg    720

cggggcgagg cggagaggtg cggcggcagc caatcagagc ggcgcgctcc gaaagtttcc    780

ttttatggcg aggcggcggc ggcggcggcc ctataaaaag cgaagcgcgc ggcgggcggg    840

agtcgctgcg ttgccttcgc cccgtgcccc gctccgccgc cgcctcgcgc cgcccgcccc    900

ggctctgact gaccgcgtta ctcccacagg tgagcgggcg ggacggccct tctcctccgg    960

gctgtaatta gcgcttggtt taatgacggc ttgtttcttt tctgtggctg cgtgaaagcc   1020

ttgaggggct ccgggagggc cctttgtgcg gggggagcgg ctcggggggt gcgtgcgtgt   1080

gtgtgtgcgt ggggagcgcc gcgtgcggct ccgcgctgcc cggcggctgt gagcgctgcg   1140

ggcgcggcgc ggggctttgt gcgctccgca gtgtgcgcga ggggagcgcg gccgggggcg   1200

gtgccccgcg gtgcgggggg ggctgcgagg ggaacaaagg ctgcgtgcgg ggtgtgtgcg   1260

tgggggggtg agcagggggt gtgggcgcgt cggtcgggct gcaacccccc ctgcaccccc   1320

ctccccgagt tgctgagcac ggcccggctt cgggtgcggg gctccgtacg gggcgtggcg   1380

cggggctcgc cgtgccgggc gggggtggc ggcaggtggg ggtgccgggc ggggcggggc   1440

cgcctcgggc cggggagggc tcgggggagg ggcgcggcgg cccccggagc gccggcggct   1500
```

-continued

```
gtcgaggcgc ggcgagccgc agccattgcc ttttatggta atcgtgcgag agggcgcagg   1560
gacttccttt gtcccaaatc tgtgcggagc cgaaatctgg gaggcgccgc cgcacccccct   1620
ctagcgggcg cggggcgaag cggtgcggcg ccggcaggaa ggaaatgggc ggggagggcc   1680
ttcgtgcgtc gccgcgccgc cgtccccttc tccctctcca gcctcggggc tgtccgcggg   1740
gggacggctg ccttcggggg ggacggggca gggcggggtt cggcttctgg cgtgtgaccg   1800
gcggctctag agcctctgct aaccatgttc atgccttctt ctttttccta cagctcctgg   1860
gcaacgtgct ggttattgtg ctgtctcatc attttggcaa agaattgatt aattcgagcg   1920
aacgcgtgcc accatggaag cagtcgccgt cgccgcagca gtgggtgtcc tcctcctcgc   1980
cggtgctgga ggtgccgccg gggacgaggc ccgcgaggcc gcagctgtgc gggcccttgt   2040
ggcccggctt ctcggaccgg gccctgccgc cgacttcagc gtgtcagtgg aacgcgcact   2100
ggctgcgaag cctgggctcg atacttactc cctgggcggg ggtggtgccg ccagagtgcg   2160
ggtccgggga agcaccgggg tggccgccgc ggccggcctg caccggtacc ttcgggactt   2220
ttgcggctgt catgtcgctt ggtccggatc ccagctgcgc ctcccccgac cgctgcccgc   2280
cgtgcctgga gagctgaccg aggccactcc gaaccggtac agatactatc agaacgtgtg   2340
cactcagtcc tactccttcg tgtggtggga ctgggccaga tgggagcggg agattgactg   2400
gatggccctg aacggtatca acctcgcctt ggcctggtcc ggccaggagg ccatttggca   2460
gagggtgtac cttgcactgg gactgactca agccgagatc aacgagtttt tcaccggccc   2520
cgctttcctt gcctgggggc gcatgggcaa cctccacacc tgggacgggc ctctgccgcc   2580
ctcctggcat atcaagcagc tgtacctcca gcacagggtg cttgaccaga tgcggagctt   2640
tggaatgacc cctgtgctgc ccgcgttcgc gggtcacgtg ccagaagcag tgactcgcgt   2700
gttcccccaa gtgaacgtca ccaaaatggg atcgtgggga cactttaact gctcttattc   2760
ctgctccttc ctcttggcgc cggaggaccc gatcttcccg attattggat cgctgttcct   2820
gcgggagctg atcaaggagt tcggaaccga ccacatctac ggcgctgaca ccttcaacga   2880
gatgcagccg ccttcctccg aaccatcgta cctcgcggcc gctactactg cggtgtacga   2940
ggccatgacc gcagtggata ccgaagccgt ctggctgctg caagggtggt tgttccagca   3000
ccagccgcag ttttggggac ccgcccagat tcgcgccgtg ctgggcgccg tgcctagggg   3060
tcgcctgctc gtgctggacc tgttcgccga gtcccagcca gtgtacacta ggaccgcgtc   3120
gttccaagga cagcccttca tttggtgtat gcttcacaac ttcgggggca accacggtct   3180
gttcggagcc ttggaagccg tgaatggcgg tcccgaggca gcgcggcttt tccccaactc   3240
aaccatggtc ggaaccggaa tggcccctga aggaatctcc cagaacgaag tcgtgtactc   3300
gctgatggca gagctgggct ggcggaagga tcctgtccct gatctcgccg cctgggtgac   3360
atccttcgcc gctcgccgct atggtgtctc ccatccggat gccggagccg catggaggct   3420
gctgctgaga tccgtgtaca actgctcggg agaagcgtgt cggggacata acaggtcccc   3480
actcgtgcgc agaccgagcc tgcagatgaa cacctccatc tggtacaacc ggtccgacgt   3540
gttcgaagcg tggagactgc tgctgacttc cgcccccgagc ctcgcgacca gcccggcgtt   3600
ccgctacgat ctcctggacc tcacaagaca ggcggtccaa gaactggtgt ccctgtacta   3660
cgaagaggcc cgctccgcat acctcagcaa ggaactcgca tcgttgctga gggccggcgg   3720
agtgctggca tacgagctgc tgccggccct ggacgaagtg ctggccagcg acagccggtt   3780
cctgctgggc tcttggctgg aacaggcccg cgctgctgcg gtgtccgaag ccgaagcgga   3840
cttctacgag cagaactcac ggtaccaact gaccctctgg ggtccggagg gcaacattct   3900
```

```
ggactacgcc aacaagcaac tcgccggcct ggtcgcaaat tactatactc ctcggtggag   3960

gctgttcctg gaagcgctgg tcgattcagt ggctcagggg atcccattcc aacagcacca   4020

attcgacaag aacgtgttcc agcttgagca ggcctttgtg ttgtcgaagc agcgctaccc   4080

cagccagcca cggggagaca cggtggacct ggccaagaag atcttcctga aatactaccc   4140

aagatgggtg gccggctcgt ggtaggaatt cgagctcggt acccgggaat caattcactc   4200

ctcaggtgca ggctgcctat cagaaggtgg tggctggtgt ggccaatgcc ctggctcaca   4260

aataccactg agatcttttt ccctctgcca aaaattatgg ggacatcatg aagccccttg   4320

agcatctgac ttctggctaa taaaggaaat ttattttcat tgcaatagtg tgttggaatt   4380

ttttgtgtct ctcactcgga aggacatatg ggagggcaaa tcatttaaaa catcagaatg   4440

agtatttggt ttagagtttg gcaacatatg cccatatgct ggctgccatg aacaaaggtt   4500

ggctataaag aggtcatcag tatatgaaac agccccctgc tgtccattcc ttattccata   4560

gaaaagcctt gacttgaggt tagatttttt ttatattttg ttttgtgtta ttttttttctt   4620

taacatccct aaaatttcc ttacatgttt tactagccag atttttcctc ctctcctgac   4680

tactcccagt catagctgtc cctcttctct tatggagatc cctcgacctg cagcccaagc   4740

tgtagataag tagcatggcg ggttaatcat taactacaag gaacccctag tgatggagtt   4800

ggccactccc tctctgcgcg ctcgctcgct cactgaggcc gcccgggctt tgcccgggcg   4860

gcctcagtga gcgagcgagc gcgcag                                        4886
```

<210> SEQ ID NO 22
<211> LENGTH: 2244
<212> TYPE: DNA
<213> ORGANISM: Artificial Sequence
<220> FEATURE:
<223> OTHER INFORMATION: cohNaglu-version3 CDS sequence

<400> SEQUENCE: 22

```
cgcgtgccac catggaggct gtcgccgtcg ccgccgctgt cggagtgctg ctgctggctg     60

gggctggagg ggctgctgga gatgaggcta gggaagctgc agctgtgcgc gcactggtcg    120

cacgactgct gggacctggg ccagcagccg acttctctgt gagtgtcgag cgagcactgg    180

ctgcaaagcc tggcctggat acctacagtc tgggaggagg aggagcagct cgagtgaggg    240

tcagagggtc aacaggagtg gcagcagctg caggactgca ccgatatctg cgagactttt    300

gcggctgtca tgtggcctgg tcaggaagcc agctgaggct gcccagacct ctgccagcag    360

tgccaggcga gctgacagaa gccactccca accggtaccg ctactatcag aatgtgtgca    420

cccagtccta ttctttcgtc tggtgggact gggctcgatg ggagcgcgaa atcgattgga    480

tggcactgaa cggaattaat ctggcactgg catggagcgg acaggaggca atctggcaga    540

gagtgtacct ggcactggga ctgactcagg ccgagattaa cgagttcttc accgggccag    600

cttttctggc atggggacgg atggggaatc tgcacacatg ggacggacca ctgccacctt    660

cttggcacat caagcagctg tatctgcagc atagggtgct ggatcagatg agaagttttg    720

gcatgactcc agtgctgccc gctttcgcag gacacgtccc tgaggccgtg accagggtgt    780

tcccacaggt gaacgtcact aagatgggca gctggggaca ttttaattgc agttactcat    840

gtagcttcct gctggcccct gaagacccaa tttttcccat cattggcagc ctgttcctgc    900

gggagctgat caaagaattt ggaaccgacc acatctacgg ggccgataca ttcaacgaga    960

tgcagccacc cagctccgaa ccttcctacc tggccgctgc aaccacagca gtgtatgagg   1020
```

```
ccatgaccgc tgtggacaca gaagccgtct ggctgctgca ggggtggctg tttcagcatc   1080

agccacagtt ctggggacct gcacagatcc gagctgtgct gggagcagtc ccacgaggaa   1140

ggctgctggt gctggatctg tttgccgagt cccagcccgt ctacactagg accgcttctt   1200

tccagggcca gccttttatt tggtgtatgc tgcacaactt tggagggaat catgggctgt   1260

tcggagcact ggaggcagtg aacggaggac cagaagcagc tagactgttt cctaattcta   1320

ctatggtggg caccggaatg gctcccgagg gcatctcaca gaatgaagtg gtctacagcc   1380

tgatggcaga gctgggatgg cgaaaggacc cagtgcctga tctggcagcc tgggtcacta   1440

gtttcgctgc aaggagatac ggggtgtcac accctgacgc tggagcagct tggcgactgc   1500

tgctgaggtc tgtgtataac tgcagtgggg aggcctgtag aggccataat cgatccccac   1560

tggtgcggcg accatcactg cagatgaaca ccagcatttg gtacaatcga tccgatgtgt   1620

ttgaagcttg gaggctgctg ctgacaagtg ccccttcact ggctacttct ccagcattca   1680

gatatgacct gctggatctg acacggcagg cagtgcagga gctggtcagc ctgtactatg   1740

aggaagctcg cagcgcatac ctgtccaaag aactggcatc cctgctgagg gcaggaggag   1800

tgctggctta tgagctgctg ccagctctgg acgaagtcct ggcatccgat tctcgctttc   1860

tgctgggaag ctggctggag caggcccgag cagccgctgt gtccgaggcc gaagctgact   1920

tctacgagca gaactctagg tatcagctga ctctgtgggg acccgaaggg aacatcctgg   1980

attacgccaa taagcagctg gccggactgg tggctaatta ctatacccct agatggcggc   2040

tgttcctgga ggcactggtg gacagcgtcg ctcaggggat tccattccag cagcaccagt   2100

ttgataagaa cgtgttccag ctggaacagg cctttgtcct gtctaaacag cggtacccta   2160

gtcagccacg cggggacaca gtggatctgg ctaagaaaat cttcctgaaa tactatccta   2220

gatgggtcgc cggcagctgg tgag                                          2244
```

```
<210> SEQ ID NO 23
<211> LENGTH: 8467
<212> TYPE: DNA
<213> ORGANISM: Artificial Sequence
<220> FEATURE:
<223> OTHER INFORMATION: pAAV-CAG-cohNaglu-version3 sequence

<400> SEQUENCE: 23

gggcgatcgg tgcgggcctc ttcgctatta cgccagctgc gcgctcgctc gctcactgag     60

gccgcccggg caaagcccgg gcgtcgggcg acctttggtc gcccggcctc agtgagcgag    120

cgagcgcgca gagagggagt ggccaactcc atcactaggg gttccttgta gttaatgatt    180

aacccgccat gctacttatc tactcgacat tgattattga ctagttatta atagtaatca    240

attacggggt cattagttca tagcccatat atggagttcc gcgttacata acttacggta    300

aatggcccgc ctggctgacc gcccaacgac ccccgcccat tgacgtcaat aatgacgtat    360

gttcccatag taacgccaat agggactttc cattgacgtc aatgggtgga gtatttacgg    420

taaactgccc acttggcagt acatcaagtg tatcatatgc caagtacgcc ccctattgac    480

gtcaatgacg gtaaatggcc cgcctggcat tatgcccagt acatgacctt atgggacttt    540

cctacttggc agtacatcta cgtattagtc atcgctatta ccatggtcga ggtgagcccc    600

acgttctgct tcactctccc catctccccc ccctccccac ccccaatttt gtatttattt    660

atttttaat tattttgtgc agcgatgggg gcgggggggg gggggggcg cgcgccaggc     720

ggggcggggc ggggcgaggg gcggggcggg gcgaggcgga gaggtgcggc ggcagccaat    780

cagagcggcg cgctccgaaa gtttcctttt atggcgaggc ggcggcggcg gcggccctat    840
```

```
aaaaagcgaa gcgcgcggcg ggcgggagtc gctgcgttgc cttcgccccg tgccccgctc    900
cgccgccgcc tcgcgccgcc cgccccggct ctgactgacc gcgttactcc cacaggtgag    960
cgggcgggac ggcccttctc ctccgggctg taattagcgc ttggtttaat gacggcttgt   1020
ttcttttctg tggctgcgtg aaagccttga ggggctccgg gagggccctt tgtgcggggg   1080
gagcggctcg gggggtgcgt gcgtgtgtgt gtgcgtgggg agcgccgcgt gcggctccgc   1140
gctgcccggc ggctgtgagc gctgcgggcg cggcgcgggg ctttgtgcgc tccgcagtgt   1200
gcgcgagggg agcgcggccg ggggcggtgc cccgcggtgc ggggggggct gcgaggggaa   1260
caaaggctgc gtgcggggtg tgtgcgtggg ggggtgagca gggggtgtgg gcgcgtcggt   1320
cgggctgcaa ccccccctgc acccccctcc ccgagttgct gagcacggcc cggcttcggg   1380
tgcggggctc cgtacggggc gtggcgcggg gctcgccgtg ccgggcgggg ggtggcggca   1440
ggtgggggtg ccgggcgggg cggggccgcc tcgggccggg gagggctcgg gggaggggcg   1500
cggcggcccc cggagcgccg gcggctgtcg aggcgcggcg agccgcagcc attgcctttt   1560
atggtaatcg tgcgagaggg cgcagggact tcctttgtcc caaatctgtg cggagccgaa   1620
atctgggagg cgccgccgca ccccctctag cgggcgcggg gcgaagcggt gcggcgccgg   1680
caggaaggaa atgggcgggg agggccttcg tgcgtcgccg cgccgccgtc cccttctccc   1740
tctccagcct cggggctgtc cgcgggggga cggctgcctt cggggggac ggggcagggc   1800
ggggttcggc ttctggcgtg tgaccggcgg ctctagagcc tctgctaacc atgttcatgc   1860
cttcttcttt ttcctacagc tcctgggcaa cgtgctggtt attgtgctgt ctcatcattt   1920
tggcaaagaa ttgattaatt cgagcgaacg cgtgccacca tggaggctgt cgccgtcgcc   1980
gccgctgtcg gagtgctgct gctggctggg gctggagggg ctgctggaga tgaggctagg   2040
gaagctgcag ctgtgcgcgc actggtcgca cgactgctgg gacctgggcc agcagccgac   2100
ttctctgtga gtgtcgagcg agcactggct gcaaagcctg gcctggatac ctacagtctg   2160
ggaggaggag gagcagctcg agtgagggtc agagggtcaa caggagtggc agcagctgca   2220
ggactgcacc gatatctgcg agacttttgc ggctgtcatg tggcctggtc aggaagccag   2280
ctgaggctgc ccagacctct gccagcagtg ccaggcgagc tgacagaagc cactcccaac   2340
cggtaccgct actatcagaa tgtgtgcacc cagtcctatt ctttcgtctg gtgggactgg   2400
gctcgatggg agcgcgaaat cgattggatg gcactgaacg gaattaatct ggcactggca   2460
tggagcggac aggaggcaat ctggcagaga gtgtacctgg cactgggact gactcaggcc   2520
gagattaacg agttcttcac cgggccagct tttctggcat ggggacggat ggggaatctg   2580
cacacatggg acggaccact gccaccttct tggcacatca agcagctgta tctgcagcat   2640
agggtgctgg atcagatgag aagttttggc atgactccag tgctgcccgc tttcgcagga   2700
cacgtccctg aggccgtgac cagggtgttc ccacaggtga acgtcactaa gatgggcagc   2760
tggggacatt ttaattgcag ttactcatgt agcttcctgc tggcccctga agacccaatt   2820
tttcccatca ttggcagcct gttcctgcgg gagctgatca aagaatttgg aaccgaccac   2880
atctacgggg ccgatacatt caacgagatg cagccaccca gctccgaacc ttcctacctg   2940
gccgctgcaa ccacagcagt gtatgaggcc atgaccgctg tggacacaga agccgtctgg   3000
ctgctgcagg ggtggctgtt tcagcatcag ccacagttct ggggacctgc acagatccga   3060
gctgtgctgg gagcagtccc acgaggaagg ctgctggtgc tggatctgtt tgccgagtcc   3120
cagcccgtct acactaggac cgcttctttc cagggccagc cttttatttg gtgtatgctg   3180
```

```
cacaactttg gagggaatca tgggctgttc ggagcactgg aggcagtgaa cggaggacca   3240
gaagcagcta gactgtttcc taattctact atggtgggca ccggaatggc tcccgagggc   3300
atctcacaga atgaagtggt ctacagcctg atggcagagc tgggatggcg aaaggaccca   3360
gtgcctgatc tggcagcctg ggtcactagt ttcgctgcaa ggagatacgg ggtgtcacac   3420
cctgacgctg gagcagcttg gcgactgctg ctgaggtctg tgtataactg cagtggggag   3480
gcctgtagag gccataatcg atccccactg gtgcggcgac catcactgca gatgaacacc   3540
agcatttggt acaatcgatc cgatgtgttt gaagcttgga ggctgctgct gacaagtgcc   3600
ccttcactgg ctacttctcc agcattcaga tatgacctgc tggatctgac acggcaggca   3660
gtgcaggagc tggtcagcct gtactatgag gaagctcgca gcgcatacct gtccaaagaa   3720
ctggcatccc tgctgagggc aggaggagtg ctggcttatg agctgctgcc agctctggac   3780
gaagtcctgg catccgattc tcgctttctg ctgggaagct ggctggagca ggcccgagca   3840
gccgctgtgt ccgaggccga agctgacttc tacgagcaga actctaggta tcagctgact   3900
ctgtggggac ccgaagggaa catcctggat tacgccaata agcagctggc cggactggtg   3960
gctaattact atacccctag atggcggctg ttcctggagg cactggtgga cagcgtcgct   4020
caggggattc cattccagca gcaccagttt gataagaacg tgttccagct ggaacaggcc   4080
tttgtcctgt ctaaacagcg gtaccctagt cagccacgcg gggacacagt ggatctggct   4140
aagaaaatct tcctgaaata ctatcctaga tgggtcgccg gcagctggtg agaattcgag   4200
ctcggtaccc gggaatcaat tcactcctca ggtgcaggct gcctatcaga aggtggtggc   4260
tggtgtggcc aatgccctgg ctcacaaata ccactgagat ctttttccct ctgccaaaaa   4320
ttatggggac atcatgaagc cccttgagca tctgacttct ggctaataaa ggaaatttat   4380
tttcattgca atagtgtgtt ggaatttttt gtgtctctca ctcggaagga catatgggag   4440
ggcaaatcat ttaaaacatc agaatgagta tttggtttag agtttggcaa catatgccca   4500
tatgctggct gccatgaaca aaggttggct ataaagaggt catcagtata tgaaacagcc   4560
ccctgctgtc cattccttat tccatagaaa agccttgact tgaggttaga ttttttttat   4620
attttgtttt gtgttatttt tttctttaac atccctaaaa ttttccttac atgttttact   4680
agccagattt ttcctcctct cctgactact cccagtcata gctgtccctc ttctcttatg   4740
gagatccctc gacctgcagc ccaagctgta gataagtagc atggcgggtt aatcattaac   4800
tacaaggaac ccctagtgat ggagttggcc actccctctc tgcgcgctcg ctcgctcact   4860
gaggccgccc gggctttgcc cgggcggcct cagtgagcga gcgagcgcgc agctgcatta   4920
atgaatcggc caacgcgcgg ggagaggcgg tttgcgtatt gggcgctctt ccgcttcctc   4980
gctcactgac tcgctgcgct cggtcgttcg gctgcggcga gcggtatcag ctcactcaaa   5040
ggcggtaata cggttatcca cagaatcagg ggataacgca ggaaagaaca tgtgagcaaa   5100
aggccagcaa aaggccagga accgtaaaaa ggccgcgttg ctggcgtttt tccataggct   5160
ccgcccccct gacgagcatc acaaaaatcg acgctcaagt cagaggtggc gaaacccgac   5220
aggactataa agataccagg cgtttccccc tggaagctcc ctcgtgcgct ctcctgttcc   5280
gaccctgccg cttaccggat acctgtccgc ctttctccct tcgggaagcg tggcgctttc   5340
tcatagctca cgctgtaggt atctcagttc ggtgtaggtc gttcgctcca agctgggctg   5400
tgtgcacgaa ccccccgttc agcccgaccg ctgcgcctta tccggtaact atcgtcttga   5460
gtccaacccg gtaagacacg acttatcgcc actggcagca gccactggta acaggattag   5520
cagagcgagg tatgtaggcg gtgctacaga gttcttgaag tggtggccta actacggcta   5580
```

```
cactagaaga acagtatttg gtatctgcgc tctgctgaag ccagttacct tcggaaaaag   5640
agttggtagc tcttgatccg gcaaacaaac caccgctggt agcggtggtt tttttgtttg   5700
caagcagcag attacgcgca gaaaaaaagg atctcaagaa gatcctttga tcttttctac   5760
ggggtctgac gctcagtgga acgaaaactc acgttaaggg attttggtca tgagattatc   5820
aaaaaggatc ttcacctaga tccttttaaa ttaaaaatga agttttaaat caatctaaag   5880
tatatatgag taaacttggt ctgacagtta ccaatgctta atcagtgagg cacctatctc   5940
agcgatctgt ctatttcgtt catccatagt tgcctgactc cccgtcgtgt agataactac   6000
gatacgggag ggcttaccat ctggccccag tgctgcaatg ataccgcgag acccacgctc   6060
accggctcca gatttatcag caataaacca gccagccgga agggccgagc gcagaagtgg   6120
tcctgcaact ttatccgcct ccatccagtc tattaattgt tgccgggaag ctagagtaag   6180
tagttcgcca gttaatagtt tgcgcaacgt tgttgccatt gctacaggca tcgtggtgtc   6240
acgctcgtcg tttggtatgg cttcattcag ctccggttcc caacgatcaa ggcgagttac   6300
atgatccccc atgttgtgca aaaaagcggt tagctccttc ggtcctccga tcgttgtcag   6360
aagtaagttg gccgcagtgt tatcactcat ggttatggca gcactgcata attctcttac   6420
tgtcatgcca tccgtaagat gcttttctgt gactggtgag tactcaacca agtcattctg   6480
agaatagtgt atgcggcgac cgagttgctc ttgcccggcg tcaatacggg ataataccgc   6540
gccacatagc agaactttaa aagtgctcat cattggaaaa cgttcttcgg ggcgaaaact   6600
ctcaaggatc ttaccgctgt tgagatccag ttcgatgtaa cccactcgtg cacccaactg   6660
atcttcagca tcttttactt tcaccagcgt ttctgggtga gcaaaaacag gaaggcaaaa   6720
tgccgcaaaa aagggaataa gggcgacacg gaaatgttga atactcatac tcttcctttt   6780
tcaatattat tgaagcattt atcagggtta ttgtctcatg agcggataca tatttgaatg   6840
tatttagaaa aataaacaaa taggggttcc gcgcacattt ccccgaaaag tgccacctga   6900
cgtctaagaa accattatta tcatgacatt aacctataaa aataggcgta tcacgaggcc   6960
ctttcgtctc gcgcgtttcg gtgatgacgg tgaaaacctc tgacacatgc agctcccgga   7020
gacggtcaca gcttgtctgt aagcggatgc cgggagcaga caagcccgtc agggcgcgtc   7080
agcgggtgtt ggcgggtgtc ggggctggct taactatgcg gcatcagagc agattgtact   7140
gagagtgcac catatgcggt gtgaaatacc gcacagatgc gtaaggagaa aataccgcat   7200
caggcgattc caacatccaa taaatcatac aggcaaggca aagaattagc aaaattaagc   7260
aataaagcct cagagcataa agctaaatcg gttgtaccaa aaacattatg accctgtaat   7320
acttttgcgg gagaagcctt tatttcaacg caaggataaa aatttttaga accctcatat   7380
attttaaatg caatgcctga gtaatgtgta ggtaaagatt caaacgggtg agaaaggccg   7440
gagacagtca aatcaccatc aatatgatat tcaaccgttc tagctgataa attcatgccg   7500
gagagggtag ctatttttga gaggtctcta caaaggctat caggtcattg cctgagagtc   7560
tggagcaaac aagagaatcg atgaacggta atcgtaaaac tagcatgtca atcatatgta   7620
ccccggttga taatcagaaa agccccaaaa acaggaagat tgtataagca aatatttaaa   7680
ttgtaagcgt taatattttg ttaaaattcg cgttaaattt ttgttaaatc agctcatttt   7740
ttaaccaata ggccgaaatc ggcaaaatcc cttataaatc aaaagaatag accgagatag   7800
ggttgagtgt tgttccagtt tggaacaaga gtccactatt aaagaacgtg gactccaacg   7860
tcaaagggcg aaaaaccgtc tatcagggcg atggcccact acgtgaacca tcaccctaat   7920
```

```
caagtttttt ggggtcgagg tgccgtaaag cactaaatcg gaaccctaaa gggagccccc   7980

gatttagagc ttgacgggga aagccggcga acgtggcgag aaaggaaggg aagaaagcga   8040

aaggagcggg cgctagggcg ctggcaagtg tagcggtcac gctgcgcgta accaccacac   8100

ccgccgcgct taatgcgccg ctacagggcg cgtactatgg ttgctttgac gagcacgtat   8160

aacgtgcttt cctcgttaga atcagagcgg gagctaaaca ggaggccgat taaagggatt   8220

ttagacagga acggtacgcc agaatcctga gaagtgtttt tataatcagt gaggccaccg   8280

agtaaaagag tctgtccatc acgcaaatta accgttgtcg caatacttct ttgattagta   8340

ataacatcac ttgcctgagt agaagaactc aaactatcgg ccttgctggt aatatccaga   8400

acaatattac cgccagccat tgcaacggaa tcgccattcg ccattcaggc tgcgcaactg   8460

ttgggaa                                                             8467
```

```
<210> SEQ ID NO 24
<211> LENGTH: 4886
<212> TYPE: DNA
<213> ORGANISM: Artificial Sequence
<220> FEATURE:
<223> OTHER INFORMATION: AAV9-CAG-cohNaglu-version3 sequence

<400> SEQUENCE: 24

attacgccag ctgcgcgctc gctcgctcac tgaggccgcc cgggcaaagc ccgggcgtcg     60

ggcgaccttt ggtcgcccgg cctcagtgag cgagcgagcg cgcagagagg gagtggccaa    120

ctccatcact aggggttcct tgtagttaat gattaacccg ccatgctact tatctactcg    180

acattgatta ttgactagtt attaatagta atcaattacg gggtcattag ttcatagccc    240

atatatggag ttccgcgtta cataacttac ggtaaatggc ccgcctggct gaccgcccaa    300

cgacccccgc ccattgacgt caataatgac gtatgttccc atagtaacgc caatagggac    360

tttccattga cgtcaatggg tggagtattt acggtaaact gcccacttgg cagtacatca    420

agtgtatcat atgccaagta cgccccctat tgacgtcaat gacggtaaat ggcccgcctg    480

gcattatgcc cagtacatga ccttatggga ctttcctact tggcagtaca tctacgtatt    540

agtcatcgct attaccatgg tcgaggtgag ccccacgttc tgcttcactc tccccatctc    600

ccccccctcc ccacccccaa ttttgtattt atttattttt taattatttt gtgcagcgat    660

gggggcgggg gggggggggg ggcgcgcgcc aggcggggcg gggcggggcg aggggcgggg    720

cggggcgagg cggagaggtg cggcggcagc caatcagagc ggcgcgctcc gaaagtttcc    780

ttttatggcg aggcggcggc ggcggcggcc ctataaaaag cgaagcgcgc ggcgggcggg    840

agtcgctgcg ttgccttcgc cccgtgcccc gctccgccgc cgcctcgcgc cgcccgcccc    900

ggctctgact gaccgcgtta ctcccacagg tgagcgggcg ggacggccct tctcctccgg    960

gctgtaatta gcgcttggtt taatgacggc ttgtttcttt tctgtggctg cgtgaaagcc   1020

ttgaggggct ccgggagggc cctttgtgcg gggggagcgg ctcggggggt gcgtgcgtgt   1080

gtgtgtgcgt ggggagcgcc gcgtgcggct ccgcgctgcc cggcggctgt gagcgctgcg   1140

ggcgcggcgc ggggctttgt gcgctccgca gtgtgcgcga ggggagcgcg gccgggggcg   1200

gtgccccgcg gtgcgggggg ggctgcgagg ggaacaaagg ctgcgtgcgg ggtgtgtgcg   1260

tgggggggtg agcagggggt gtgggcgcgt cggtcgggct gcaacccccc ctgcaccccc   1320

ctccccgagt tgctgagcac ggcccggctt cgggtgcggg gctccgtacg gggcgtggcg   1380

cggggctcgc cgtgccgggc ggggggtggc ggcaggtggg ggtgccgggc ggggcggggc   1440

cgcctcgggc cggggagggc tcgggggagg ggcgcggcgg cccccggagc gccggcggct   1500
```

```
gtcgaggcgc ggcgagccgc agccattgcc ttttatggta atcgtgcgag agggcgcagg   1560
gacttccttt gtcccaaatc tgtgcggagc cgaaatctgg gaggcgccgc cgcacccccct  1620
ctagcgggcg cggggcgaag cggtgcggcg ccggcaggaa ggaaatgggc ggggagggcc   1680
ttcgtgcgtc gccgcgccgc cgtccccttc tccctctcca gcctcggggc tgtccgcggg   1740
gggacggctg ccttcggggg ggacggggca gggcggggtt cggcttctgg cgtgtgaccg   1800
gcggctctag agcctctgct aaccatgttc atgccttctt ctttttccta cagctcctgg   1860
gcaacgtgct ggttattgtg ctgtctcatc attttggcaa agaattgatt aattcgagcg   1920
aacgcgtgcc accatggagg ctgtcgccgt cgccgccgct gtcggagtgc tgctgctggc   1980
tggggctgga ggggctgctg gagatgaggc tagggaagct gcagctgtgc gcgcactggt   2040
cgcacgactg ctgggacctg gccagcagc cgacttctct gtgagtgtcg agcgagcact    2100
ggctgcaaag cctggcctgg atacctacag tctgggagga ggaggagcag ctcgagtgag   2160
ggtcagaggg tcaacaggag tggcagcagc tgcaggactg caccgatatc tgcgagactt   2220
ttgcggctgt catgtggcct ggtcaggaag ccagctgagg ctgcccagac ctctgccagc   2280
agtgccaggc gagctgacag aagccactcc caaccggtac cgctactatc agaatgtgtg   2340
cacccagtcc tattctttcg tctggtggga ctgggctcga tgggagcgcg aaatcgattg   2400
gatggcactg aacggaatta atctggcact ggcatggagc ggacaggagg caatctggca   2460
gagagtgtac ctggcactgg gactgactca ggccgagatt aacgagttct tcaccgggcc   2520
agcttttctg gcatggggac ggatggggaa tctgcacaca tgggacggac cactgccacc   2580
ttcttggcac atcaagcagc tgtatctgca gcatagggtg ctggatcaga tgagaagttt   2640
tggcatgact ccagtgctgc ccgctttcgc aggacacgtc cctgaggccg tgaccagggt   2700
gttcccacag gtgaacgtca ctaagatggg cagctgggga cattttaatt gcagttactc   2760
atgtagcttc ctgctggccc ctgaagaccc aatttttccc atcattggca gcctgttcct   2820
gcgggagctg atcaaagaat ttggaaccga ccacatctac ggggccgata cattcaacga   2880
gatgcagcca cccagctccg aaccttccta cctggccgct gcaaccacag cagtgtatga   2940
ggccatgacc gctgtggaca cagaagccgt ctggctgctg caggggtggc tgtttcagca   3000
tcagccacag ttctggggac ctgcacagat ccgagctgtg ctgggagcag tcccacgagg   3060
aaggctgctg gtgctggatc tgtttgccga gtcccagccc gtctacacta ggaccgcttc   3120
tttccagggc cagcctttta tttggtgtat gctgcacaac tttggaggga atcatgggct   3180
gttcggagca ctggaggcag tgaacggagg accagaagca gctagactgt ttcctaattc   3240
tactatggtg ggcaccggaa tggctcccga gggcatctca cagaatgaag tggtctacag   3300
cctgatggca gagctgggat ggcgaaagga cccagtgcct gatctggcag cctgggtcac   3360
tagtttcgct gcaaggagat acggggtgtc acaccctgac gctggagcag cttggcgact   3420
gctgctgagg tctgtgtata actgcagtgg ggaggcctgt agaggccata atcgatcccc   3480
actggtgcgg cgaccatcac tgcagatgaa caccagcatt tggtacaatc gatccgatgt   3540
gtttgaagct tggaggctgc tgctgacaag tgccccttca ctggctactt ctccagcatt   3600
cagatatgac ctgctggatc tgacacggca ggcagtgcag gagctggtca gcctgtacta   3660
tgaggaagct cgcagcgcat acctgtccaa agaactggca tccctgctga gggcaggagg   3720
agtgctggct tatgagctgc tgccagctct ggacgaagtc ctggcatccg attctcgctt   3780
tctgctggga agctggctgg agcaggcccg agcagccgct gtgtccgagg ccgaagctga   3840
```

-continued

```
cttctacgag cagaactcta ggtatcagct gactctgtgg ggacccgaag ggaacatcct   3900

ggattacgcc aataagcagc tggccggact ggtggctaat tactataccc ctagatggcg   3960

gctgttcctg gaggcactgg tggacagcgt cgctcagggg attccattcc agcagcacca   4020

gtttgataag aacgtgttcc agctggaaca ggcctttgtc ctgtctaaac agcggtaccc   4080

tagtcagcca cgcggggaca cagtggatct ggctaagaaa atcttcctga aatactatcc   4140

tagatgggtc gccggcagct ggtgagaatt cgagctcggt acccgggaat caattcactc   4200

ctcaggtgca ggctgcctat cagaaggtgg tggctggtgt ggccaatgcc ctggctcaca   4260

aataccactg agatcttttt ccctctgcca aaaattatgg ggacatcatg aagccccttg   4320

agcatctgac ttctggctaa taaaggaaat ttattttcat tgcaatagtg tgttggaatt   4380

ttttgtgtct ctcactcgga aggacatatg ggagggcaaa tcatttaaaa catcagaatg   4440

agtatttggt ttagagtttg gcaacatatg cccatatgct ggctgccatg aacaaaggtt   4500

ggctataaag aggtcatcag tatatgaaac agccccctgc tgtccattcc ttattccata   4560

gaaaagcctt gacttgaggt tagatttttt ttatattttg ttttgtgtta ttttttttctt   4620

taacatccct aaaattttcc ttacatgttt tactagccag atttttcctc ctctcctgac   4680

tactcccagt catagctgtc cctcttctct tatggagatc cctcgacctg cagcccaagc   4740

tgtagataag tagcatggcg ggttaatcat taactacaag gaacccctag tgatggagtt   4800

ggccactccc tctctgcgcg ctcgctcgct cactgaggcc gcccgggctt tgcccgggcg   4860

gcctcagtga gcgagcgagc gcgcag                                         4886
```

UNITED STATES PATENT AND TRADEMARK OFFICE
CERTIFICATE OF CORRECTION

| | |
|---|---|
| PATENT NO. | : 11,149,285 B2 |
| APPLICATION NO. | : 15/310524 |
| DATED | : October 19, 2021 |
| INVENTOR(S) | : Maria-Fàtima Bosch-Tubert, Virginia A. Haurigot and Albert Ribera Sanchez |

It is certified that error appears in the above-identified patent and that said Letters Patent is hereby corrected as shown below:

On the Title Page

Item (56) "OTHER PUBLICATIONS", page 2, Column 2, Line 51, --2006-- should read 2008.

Signed and Sealed this
Twenty-eighth Day of December, 2021

Drew Hirshfeld
*Performing the Functions and Duties of the
Under Secretary of Commerce for Intellectual Property and
Director of the United States Patent and Trademark Office*